United States Patent
Black et al.

(10) Patent No.: US 11,457,582 B2
(45) Date of Patent: Oct. 4, 2022

(54) QTLS CONFERRING RESISTANCE TO FUSARIUM BASAL ROT, PINK ROOT AND COMPLEMENTARY PINKS IN ONIONS

(71) Applicant: SEMINIS VEGETABLE SEEDS, INC., St. Louis, MO (US)

(72) Inventors: Lowell Black, St. Louis, MO (US); Eva King-Fan Chan, Davis, CA (US); Jeneylyne Ferrera Colcol, St. Louis, MO (US); Richard Jones, St. Louis, MO (US); Chad Kramer, Winters, CA (US); Wenwen Xiang, St. Louis, MO (US)

(73) Assignee: Seminis Vegetable Seeds, Inc., St. Louis, MO (US)

( * ) Notice: Subject to any disclaimer, the term of this patent is extended or adjusted under 35 U.S.C. 154(b) by 280 days.

(21) Appl. No.: 14/550,705

(22) Filed: Nov. 21, 2014

(65) Prior Publication Data
US 2015/0150155 A1 May 28, 2015

Related U.S. Application Data

(60) Provisional application No. 61/909,883, filed on Nov. 27, 2013.

(51) Int. Cl.
| | | |
|---|---|---|
| A01H 1/04 | (2006.01) | |
| A01H 6/04 | (2018.01) | |
| C12Q 1/6895 | (2018.01) | |
| C12N 15/82 | (2006.01) | |

(52) U.S. Cl.
CPC .............. *A01H 1/04* (2013.01); *A01H 6/045* (2018.05); *C12N 15/8243* (2013.01); *C12Q 1/6895* (2013.01); *C12Q 2600/13* (2013.01)

(58) Field of Classification Search
None
See application file for complete search history.

(56) References Cited

FOREIGN PATENT DOCUMENTS

WO WO 2006/061256 6/2006

OTHER PUBLICATIONS

Noble, D. A look at new onion varieties. (2008) Amp Agronomy; pp. 1-9.*
Marzu, J. C. Genetic Analyses of resistances to fusarium basal rot and pink root in onion. (2015) ProQuest LLC; UMI # 3673055; pp. 1-185 (Year: 2015).*
Cramer et al., "'NuMex Crimson' onion," *Hortscience*, 38(2):306-307, 2003.
Cramer, "Onion trait heritability and response from selection," *Journal of the American Society for Horticultural Science*, 131(5):646-650, 2006.
Lacy et al., "Yields of onion allium-cepa cultivars in midwestern USA organic soils infested with fusarium-oxysporum-f-sp-cepae and pyrenochaeta-terrestris," *Plant Disease*, 66(11):1003-1006, 1982.
Thornton et al., "Response of sweet Spanish onion cultivars and numbered hybrids to basal rot and pint root," *Plant Disease*, 80(6):660-663, 1996.
Duangjit et al., "Transcriptome sequencing to produce SNP-based genetic maps of onion," *Theor Appl Genet*, 126(8):2093-2101, 2013.
Galmarini, "Genetic analysis of correlated solids, flavor, and health-enhancing traits in onion (*Allium cepa* L.)," *Molecular Genetics and Genomics*, 265:543-551, 2001.
Hou, Morphological and molecular tracking of *Allium fisulosum* L. introgressed into *A. cepa* L, Doctoral dissertation, Texas Tech University, Texas, U.S. available online Aug. 19, 1998.
McCallum et al., "Genetic mapping of sulfur assimilation genes reveals a QTL for onion bulb pungency," *Theor Appl Genet*, 114(5):815-822, 2006.
Office Action regarding European Application No. 14194682, dated Mar. 14, 2018.
Kim et al., "Development of a PCR-based marker utilizing a deletion mutation in the dihydroflavonol 4-reductase (DFR) gene responsible for the lack of anthocyanin production in yellow unions (*Allium cepa*)," *Theor. Appl. Genet.* 110:588-595, 2005.
Unknown, "The Onion That Came to Texas But Never Left the Same," History of the Sweet Texas Onions. Available online at <<https://aggie-horticulture.tamu.edu/plantanswers/publications/onions/ONIONHIS.html>>. Accessed on Sep. 9, 2019.
Marzu et al., "Genetic Analyses and Mapping of Pink-Root Resistance in Onion," J. Amer. Soc. Hort. Sci., 143(6):503-507, 2018.
Ko, et al., Storage variability among short-day onion cultivars under high temperature and high relative humidity and its relationship with disease incidence and bulb characteristics, J. Amer. Soc. Hort. Sci. 127(5):848-854, 2002.
Onion World 24(8): 15-18, 2008.

* cited by examiner

Primary Examiner — Cathy Kingdon Worley
(74) Attorney, Agent, or Firm — Dentons US LLP; Alissa Eagle

(57) ABSTRACT

The present disclosure provides for unique onion plants with QTLs conferring *Fusarium* basal rot and pink root resistance and lacking the complementary pinks trait and their progeny. Such plants may comprise an introgressed QTL associated with multiple disease resistance coupled with a desirable bulb color. In certain aspects, compositions, including distinct polymorphic molecular markers, and methods for producing, breeding, identifying, selecting, and the like of plants or germplasm with disease resistance and/or desirable bulb color are provided.

7 Claims, 1 Drawing Sheet
Specification includes a Sequence Listing.

| Linkage Group | 2 | 2 | 2 | 2 | 2 | 2 | 2 | 2 | 2 | 2 | 2 | 2 | 2 | 2 | 2 | 2 | 2 | | 6 | | FBRR Path Test |
|---|---|---|---|---|---|---|---|---|---|---|---|---|---|---|---|---|---|---|---|---|---|
| Position | 41 | 42 | 45 | 47 | 48 | 49 | 50 | 51 | 52 | 53 | 55 | 55 | 55 | 57 | 58 | 62 | 63 | | 22 | | |
| Trait Location | FBR | FBR | FBR | FBR | FBR | FBR | FBR | FBR | FBR | FBRR | FBR/PR | PR | PR | PR | PR | L gene | L gene | | R gene | | Desire overall high level of resistance to capture minor effect loci |
| Favorable Allele | Serrano | Serrano | Serrano | Serrano | Serrano | Serrano | Serrano | Serrano | Serrano | Serrano | | 1706 | 1706 | 1706 | 1706 | 1706 | & Serrano | | & 1706 | | |

QTLS CONFERRING RESISTANCE TO FUSARIUM BASAL ROT, PINK ROOT AND COMPLEMENTARY PINKS IN ONIONS

CROSS REFERENCE TO RELATED APPLICATIONS

This application claims the benefit of U.S. Provisional Application No. 61/909,883 filed Nov. 27, 2013, herein incorporated by reference in its entirety.

FIELD OF THE INVENTION

The present invention relates to the field of agriculture and, more specifically, to methods and compositions for producing onion plants with resistance to disease combined with a favorable bulb color.

INCORPORATION OF SEQUENCE LISTING

The sequence listing that is contained in the file named "SEMB012US_ST25.txt," which is 61.3 kilobytes as measured in Microsoft Windows operating system and was created on Nov. 20, 2014, is filed electronically herewith and incorporated herein by reference.

BACKGROUND OF THE INVENTION

Plant disease resistance is an important trait in plant breeding, particularly for production of food crops. Economically important diseases that affect onion plants include *Fusarium* Basal Rot (*Fusarium oxysporum* f. sp. *cepae*) and Pink Root (*Phoma terrestris*), among others. These diseases can result in loss of plants, which affects commercial onion crops. Plant breeding efforts have resulted in many onion varieties that are resistant to disease, but such efforts in many cases have been complicated by issues such as genetic linkage, inadequate phenotypic assays, and complex or poorly understood inheritance of traits.

SUMMARY OF THE INVENTION

In one aspect, the invention provides an onion plant comprising resistance to *Fusarium* basal rot and pink root, wherein the plant further comprises lack of the complementary pinks trait. In one embodiment, the onion plant comprises a cis-coupled linkage comprising resistance to *Fusarium* basal rot conferred by said onion genomic region defined by loci NQ0345038 (SEQ ID NO:3) and NQ0257326 (SEQ ID NO:23) on linkage group 2 (LG2), resistance to pink root conferred by said onion genomic region defined by loci NQ0257277 (SEQ ID NO:22) and NQ0258453 (SEQ ID NO:27) on linkage group 2 (LG2), and lack of the complimentary pinks bulb color conferred by said onion genomic region defined by loci NQ0257220 (SEQ ID NO:26) and NQ0257692 (SEQ ID NO:29) on linkage group 2 (LG2). In another embodiment, the cis-coupled linkage is introgressed into an onion variety selected from the group consisting of North American Yellow and Universal Yellow. In another embodiment, the invention provides a part of an onion plant comprising resistance to *Fusarium* basal rot and pink root, wherein the plant further comprises lack of the complementary pinks trait, wherein the part of a plant is further defined as pollen, an ovule, a leaf, an embryo, a root, a root tip, an anther, a flower, a bulb, a stem, a shoot, a seed, a protoplast, a cell, and a callus. In still other embodiments, the onion plant is an agronomically elite line, or a hybrid or an inbred.

In one aspect, the invention provides an onion plant comprising in its genome at least one introgressed allele locus, wherein said introgressed allele locus comprises: an onion genomic region defined by loci NQ0345038 (SEQ ID NO:3) and NQ0257326 (SEQ ID NO:23) on linkage group 2 (LG2), conferring resistance to *Fusarium* basal rot (FBR); an onion genomic region defined by loci NQ0257277 (SEQ ID NO:22) and NQ0258453 (SEQ ID NO:27) on linkage group 2 (LG2), conferring resistance to Pink Root (PR); an onion genomic region defined by loci NQ0257220 (SEQ ID NO:26) and NQ0257692 (SEQ ID NO:29) on linkage group 2 (LG2) conferring lack of the Complimentary Pinks bulb color; an onion genomic region defined by loci NQ0258523 (SEQ ID NO:30) and NQ0345206 (SEQ ID NO:36) on linkage group 3 (LG3), conferring resistance to *Fusarium* basal rot (FBR); an onion genomic region defined by loci NQ0345564 (SEQ ID NO:38) and NQ0257917 (SEQ ID NO:63) on linkage group 4 (LG4), conferring resistance to *Fusarium* basal rot (FBR); an onion genomic region defined by loci NQ0344978 (SEQ ID NO:49) and NQ0344766 (SEQ ID NO:55) on linkage group 4 (LG4), conferring resistance to Pink Root (PR); an onion genomic region defined by loci NQ0258361 (SEQ ID NO:37) and NQ0344778 (SEQ ID NO:61) on linkage group 4 (LG4) conferring production or inhibition of bulb color; or an onion genomic region defined by loci NQ0257378 (SEQ ID NO:64) and NQ0345734 (SEQ ID NO:74) on linkage group 6 (LG6) conferring a red pigment bulb color; or a progeny plant therefrom. In one embodiment, the onion plant comprises a cis-coupled linkage comprising resistance to *Fusarium* basal rot (FBR) conferred by said onion genomic region defined by loci NQ0345038 (SEQ ID NO:3) and NQ0257326 (SEQ ID NO:23) on linkage group 2 (LG2), resistance to Pink Root conferred by said onion genomic region defined by loci NQ0257277 (SEQ ID NO:22) and NQ0258453 (SEQ ID NO:27) on linkage group 2 (LG2), and lack of the Complimentary Pinks bulb color conferred by said onion genomic region defined by loci NQ0257220 (SEQ ID NO:26) and NQ0257692 (SEQ ID NO:29) on linkage group 2 (LG2). In another embodiment, the cis-coupled linkage is introgressed into an onion variety selected from the group consisting of North American Yellow and Universal Yellow. In another embodiment, a part of the onion plant is defined as pollen, an ovule, a leaf, an embryo, a root, a root tip, an anther, a flower, a bulb, a stem, a shoot, a seed, a protoplast, a cell, and a callus. In other embodiments, the onion plant is an agronomically elite line or a hybrid or an inbred.

In another aspect, the invention provides a method of detecting in at least one onion plant a genotype associated with disease resistance or bulb color, the method comprising the step of: (i) detecting in at least one onion plant an allele of at least one polymorphic nucleic acid that is associated with disease resistance or bulb color, wherein the polymorphic nucleic acid is in or genetically linked to: an onion genomic region defined by loci NQ0345038 (SEQ ID NO:3) and NQ0257326 (SEQ ID NO:23) on linkage group 2 (LG2), conferring resistance to *Fusarium* basal rot (FBR); an onion genomic region defined by loci NQ0257277 (SEQ ID NO:22) and NQ0258453 (SEQ ID NO:27) on linkage group 2 (LG2), conferring resistance to Pink Root (PR); an onion genomic region defined by loci NQ0257220 (SEQ ID NO:26) and NQ0257692 (SEQ ID NO:29) on linkage group 2 (LG2) conferring lack of the Complimentary Pinks bulb color; an onion genomic region defined by loci NQ0258523 (SEQ ID NO:30) and NQ0345206 (SEQ ID NO:36) on linkage group 3 (LG3), conferring resistance to *Fusarium* basal rot (FBR); an onion genomic region defined by loci NQ0345564 (SEQ ID NO:38) and NQ0257917 (SEQ ID NO:63) on linkage group 4 (LG4), conferring resistance to *Fusarium* basal rot (FBR); an onion genomic region defined by loci NQ0344978 (SEQ ID NO:49) and NQ0344766 (SEQ ID NO:55) on linkage group 4 (LG4), conferring resistance to Pink Root (PR); an onion genomic region defined by loci NQ0258361 (SEQ ID NO:37) and NQ0344778 (SEQ ID NO:61) on linkage group 4 (LG4) conferring production or inhibition of bulb color; or an onion genomic region defined by loci NQ0257378 (SEQ ID NO:64) and NQ0345734 (SEQ ID NO:74) on linkage group 6 (LG6) conferring a red pigment bulb color. In an embodiment, the method further comprises the step of: (ii) selecting at least one onion plant in which a genotype associated with disease resistance or bulb color has been detected. In other embodiments, the onion plant is an agronomically elite line or a hybrid or an inbred, or a progeny plant resulting from the cross of at least one parent plant comprising disease resistance.

In another aspect, the invention provides a method for producing an onion plant that comprises in its genome at least one locus associated with disease resistance or bulb color, the method comprising: (i) crossing a first onion plant lacking a locus associated with disease resistance or bulb color with a second onion plant comprising a locus associated with disease resistance or bulb color defined by: an onion genomic region defined by loci NQ0345038 (SEQ ID NO:3) and NQ0257326 (SEQ ID NO:23) on linkage group 2 (LG2), conferring resistance to *Fusarium* basal rot (FBR); an onion genomic region defined by loci NQ0257277 (SEQ ID NO:22) and NQ0258453 (SEQ ID NO:27) on linkage group 2 (LG2), conferring resistance to Pink Root (PR); an onion genomic region defined by loci NQ0257220 (SEQ ID NO:26) and NQ0257692 (SEQ ID NO:29) on linkage group 2 (LG2) conferring lack of the Complimentary Pinks bulb color; an onion genomic region defined by loci NQ0258523 (SEQ ID NO:30) and NQ0345206 (SEQ ID NO:36) on linkage group 3 (LG3), conferring resistance to *Fusarium* basal rot (FBR); an onion genomic region defined by loci NQ0345564 (SEQ ID NO:38) and NQ0257917 (SEQ ID NO:63) on linkage group 4 (LG4), conferring resistance to *Fusarium* basal rot (FBR); an onion genomic region defined by loci NQ0344978 (SEQ ID NO:49) and NQ0344766 (SEQ ID NO:55) on linkage group 4 (LG4), conferring resistance to Pink Root (PR); an onion genomic region defined by loci NQ0258361 (SEQ ID NO:37) and NQ0344778 (SEQ ID NO:61) on linkage group 4 (LG4) conferring production or inhibition of bulb color; or an onion genomic region defined by loci NQ0257378 (SEQ ID NO:64) and NQ0345734 (SEQ ID NO:74) on linkage group 6 (LG6) conferring a red pigment bulb color; (ii) detecting in progeny resulting from said crossing at least a first polymorphic locus in or genetically linked to said locus associated with disease resistance or bulb color; and (iii) selecting an onion plant comprising said polymorphism and said locus associated with disease resistance or bulb color. In an embodiment, the method further comprises the step of: (iv) crossing the onion plant of step (iii) with itself or another onion plant to produce a further generation. In another embodiment, steps (iii) and (iv) are repeated from about 3 times to about 10 times. In another embodiment, the onion plant comprises resistance to *Fusarium* basal rot (FBR) conferred by said onion genomic region defined by loci NQ0345038 (SEQ ID NO:3) and NQ0257326 (SEQ ID NO:23) on linkage group 2 (LG2), resistance to Pink Root conferred by said onion genomic region defined by loci NQ0257277 (SEQ ID NO:22) and NQ0258453 (SEQ ID NO:27) on linkage group 2 (LG2), and lack of the Complimentary Pinks bulb color conferred by said onion genomic region defined by loci NQ0257220 (SEQ ID NO:26) and NQ0257692 (SEQ ID NO:29) on linkage group 2 (LG2). In other embodiments, the onion plant is an agronomically elite line or a hybrid or an inbred.

Another aspect of the invention provides a method of onion plant breeding, the method comprising the steps of: (i) selecting at least a first onion plant comprising at least one allele of a polymorphic nucleic acid that is in or genetically linked to a QTL associated with disease resistance or bulb color, wherein the QTL maps to: an onion genomic region defined by loci NQ0345038 (SEQ ID NO:3) and NQ0257326 (SEQ ID NO:23) on linkage group 2 (LG2), conferring resistance to *Fusarium* basal rot (FBR); an onion genomic region defined by loci NQ0257277 (SEQ ID NO:22) and NQ0258453 (SEQ ID NO:27) on linkage group 2 (LG2), conferring resistance to Pink Root (PR); an onion genomic region defined by loci NQ0257220 (SEQ ID NO:26) and NQ0257692 (SEQ ID NO:29) on linkage group 2 (LG2) conferring lack of the Complimentary Pinks bulb color; an onion genomic region defined by loci NQ0258523 (SEQ ID NO:30) and NQ0345206 (SEQ ID NO:36) on linkage group 3 (LG3), conferring resistance to *Fusarium* basal rot (FBR); an onion genomic region defined by loci NQ0345564 (SEQ ID NO:38) and NQ0257917 (SEQ ID NO:63) on linkage group 4 (LG4), conferring resistance to *Fusarium* basal rot (FBR); an onion genomic region defined by loci NQ0344978 (SEQ ID NO:49) and NQ0344766 (SEQ ID NO:55) on linkage group 4 (LG4), conferring resistance to Pink Root (PR); an onion genomic region defined by loci NQ0258361 (SEQ ID NO:37) and NQ0344778 (SEQ ID NO:61) on linkage group 4 (LG4) conferring production or inhibition of bulb color; or an onion genomic region defined by loci NQ0257378 (SEQ ID NO:64) and NQ0345734 (SEQ ID NO:74) on linkage group 6 (LG6) conferring a red pigment bulb color; (ii) crossing the first onion plant with itself or a second onion plant to produce progeny onion plants comprising the QTL associated with disease resistance or bulb color. In one embodiment, at least one polymorphic nucleic acid that is genetically linked to said QTL associated with disease resistance or bulb color maps within 40 cM, 20 cM, 15 cM, 10 cM, 5 cM, or 1 cM of said QTL associated with disease resistance or bulb color.

In another aspect, the invention provides a method of introgressing an allele into an onion plant, the method comprising: (i) genotyping at least one onion plant in a population with respect to at least one polymorphic nucleic acid located in or genetically linked to: an onion genomic region defined by loci NQ0345038 (SEQ ID NO:3) and NQ0257326 (SEQ ID NO:23) on linkage group 2 (LG2), conferring resistance to *Fusarium* basal rot (FBR); an onion genomic region defined by loci NQ0257277 (SEQ ID NO:22) and NQ0258453 (SEQ ID NO:27) on linkage group 2 (LG2), conferring resistance to Pink Root (PR); an onion genomic region defined by loci NQ0257220 (SEQ ID NO:26) and NQ0257692 (SEQ ID NO:29) on linkage group 2 (LG2) conferring lack of the Complimentary Pinks bulb color; an onion genomic region defined by loci NQ0258523 (SEQ ID NO:30) and NQ0345206 (SEQ ID NO:36) on linkage group 3 (LG3), conferring resistance to *Fusarium* basal rot (FBR); an onion genomic region defined by loci NQ0345564 (SEQ ID NO:38) and NQ0257917 (SEQ ID NO:63) on linkage group 4 (LG4), conferring resistance to *Fusarium* basal rot (FBR); an onion genomic region defined by loci NQ0344978 (SEQ ID NO:49) and NQ0344766 (SEQ ID NO:55) on linkage group 4 (LG4), conferring resistance to Pink Root (PR); an onion genomic region defined by loci NQ0258361 (SEQ ID NO:37) and NQ0344778 (SEQ ID NO:61) on linkage group 4 (LG4) conferring production or inhibition of bulb color; or an onion genomic region defined by loci NQ0257378 (SEQ ID NO:64) and NQ0345734 (SEQ ID NO:74) on linkage group 6 (LG6) conferring a red pigment bulb color; (ii) selecting from the population at least one onion plant comprising at least one allele associated with disease resistance or bulb color. In some embodiments, the onion plant is an agronomically elite line or a hybrid or an inbred. In another embodiment, the invention provides an onion plant obtained by such methods.

In another aspect, the invention provides an onion plant comprising resistance to *Fusarium* basal rot and pink root, wherein the plant further comprises lack of the complementary pinks trait.

BRIEF DESCRIPTION OF THE DRAWINGS

FIG. 1: Shows a desired haplotype configuration for Universal Yellow onion donor germplasm that is resistant to both *Fusarium* Basal Rot (FBR) and Pink Root (PR). A 1706 parental allele on chromosome 2 (position 62-63) results in North American Yellow onion germplasm that is resistant to both *Fusarium* Basal Rot (FBR) and Pink Root (PR).

BRIEF DESCRIPTION OF THE SEQUENCE LISTING

SEQ ID NOs:1-74—Marker sequences used for marker-assisted selection (MAS) of disease resistance and bulb color phenotypes in onion.

SEQ ID NOs:75-115—Sequences of VIC-labeled probes used for Taqman® assays.

SEQ ID NOs:116-156—Sequences of FAM-labeled probes used for Taqman® assays.

SEQ ID NOs:157-197 and 239-240—Sequences of forward primers used for Taqman® assays.

SEQ ID NOs:198-238—Sequences of reverse primers used for Taqman® assays.

DETAILED DESCRIPTION OF THE INVENTION

The present invention provides methods and compositions for producing disease resistant onion plants exhibiting resistance to *Fusarium* Basal Rot (FBR), caused by the fungal pathogen *Fusarium oxysporum* f. sp. *cepae* and/or Pink Root (PR), caused by the fungal pathogen *Phoma terrestris*; while also exhibiting an agronomically desirable bulb color (e.g. yellow), conferred by the lack of a trait called complementary pinks (CP) and/or a bulb color locus identified herein. Methods of breeding and selecting disease resistant onion lines are further provided, as well as plants and plant parts of such disease resistant onions. Also disclosed herein are molecular markers that are linked to quantitative trait loci ("QTL") contributing to such plant disease resistance. These markers facilitate the use of these loci singly or in any desired loci combination.

Surprisingly, the inventors have been able to develop methods and compositions that allow, for the first time, efficient production of onion plants with specific disease resistance, while avoiding or minimizing the undesirable CP bulb color trait, which had previously been associated with such disease resistance loci. Such traits have previously been unavailable for combination into a single onion plant without the deleterious linkage of disease resistance loci and the undesirable CP trait. The present invention permits production of an onion plant possessing a desired disease resistance trait as described herein without a genetically linked allele causing the CP trait. The ability to combine these traits into a single onion plant is the result of breaking of the linkage between the disease resistance trait and the presence of CP. In an embodiment of the present invention, breaking linkage between two traits may be accomplished by repeated meiotic events (i.e., recombination) to produce plants with both desired traits. Thus, one embodiment of the current invention provides an onion plant comprising disease resistance and a desired bulb color, wherein the desired bulb color is the result of the absence of an allele conferring CP.

The invention represents a significant advance in the art in that it provides, in certain embodiments, methods and compositions permitting introgression or resistance to selected diseases and combinations of diseases into a commercially desirable genetic background. In specific embodiments of the invention, a QTL conferring resistance to at least one disease including, but not limited to FBR and PR, and lacking CP and/or providing a desirable bulb color, is identified and defined by the map interval bounded by positions in the onion genome that correspond to NQ0345038 (SEQ ID NO:3) and NQ0257326 (SEQ ID NO:23) on linkage group 2 (LG 2); NQ0257277 (SEQ ID NO:22) and NQ0258453 (SEQ ID NO:27) on linkage group 2 (LG 2); NQ0257220 (SEQ ID NO:26) and NQ0257692 (SEQ ID NO:29) on linkage group 2 (LG 2); NQ0258523 (SEQ ID NO:30) and NQ0345206 (SEQ ID NO:36) on linkage group 3 (LG 3); NQ0345564 (SEQ ID NO:38) and NQ0257917 (SEQ ID NO:63) on linkage group 4 (LG 4); NQ0344978 (SEQ ID NO:49) and NQ0344766 (SEQ ID NO:55) on linkage group 4 (LG 4); NQ0258361 (SEQ ID NO:37) and NQ0344778 (SEQ ID NO:61) on linkage group 4 (LG 4); or NQ0257378 (SEQ ID NO:64) and NQ0345734 (SEQ ID NO:74) on linkage group 6 (LG6). The invention further provides an onion plant comprising one or more QTL conferring disease resistance, along with a desirable bulb color, wherein the desirable bulb color may be conferred by lack of CP or by another bulb color locus described herein. In one embodiment, the desirable bulb color in accordance with the invention may be conferred by a lack of the CP locus, a gene in the anthocyanin biosynthesis pathway, a dihydroflavanol 4-reductase (DFR) gene, or other genes or loci known in the art which confer a desired bulb color. In accordance with the present invention, markers within the QTL intervals defined herein may be used to identify disease resistant plants. In a specific embodiment, novel cis-coupling events as described herein may be combined together into a single haplotype of a linkage group, for example on LG2, in order to produce plants with disease resistance together with additional desired traits.

Through use of the corresponding markers provided herein and/or other markers that may be linked thereto, one of skill in the art may use genetic markers to introgress and combine ("stack") disease resistance traits or other desirable traits in commercially relevant onion lines. In a specific embodiment, onion plants according to the invention may be crossed to produce hybrid onion plants or varieties that comprise the desired traits.

In accordance with the invention, identified disease resistance QTL may be introgressed into any onion genetic background. In an embodiment, onion lines comprising a commercially favorable bulb color, such as a yellow bulb, including North American yellow or Universal Yellow for example, may be used for introgression of QTL conferring disease resistance combined with any additional desirable trait such as bulb color and/or lack of CP. Thus, using the methods of the invention and starting from any genetic sources identified herein or available in the art, an onion plant of any genotype may be produced that further comprises the desired disease resistance, including FBR and PR, coupled with any additional traits. In addition, such plants may be prepared to comprise other desired traits, for example elite agronomic traits.

Certain embodiments further provide methods of detecting in an onion plant a genotype associated with disease resistance, which may be coupled with a desired bulb color. Certain embodiments also provide methods of identifying and selecting an onion plant comprising in its genome a genotype associated with disease resistance coupled with a desired bulb color. Further embodiments provide methods of producing an onion plant that comprises in its genome at least one introgressed locus associated with disease resistance coupled with a desired bulb color and methods for introgressing such alleles into a given onion variety. Onion plants and parts thereof made by any of said methods are also provided for, as well as polymorphic nucleic acid sequences that may be used in the production and identification of such plants. In an embodiment, the invention provides a food product comprising such an onion plant or a bulb or other plant part of such a plant.

By providing markers to obtain a phenotype of interest, such as disease resistance, or disease resistance coupled with a desired bulb color, the invention results in significant economization by allowing replacement of costly, time-intensive, and potentially unreliable phenotyping assays. Further, breeding programs can be designed to explicitly drive the frequency of specific favorable phenotypes by targeting particular genotypes. Fidelity of these associations may be monitored continuously to ensure maintained predictive ability and informed breeding decisions.

In accordance with the invention, one of skill in the art may identify a candidate germplasm source possessing a desirable disease resistance phenotype coupled with a desired bulb color phenotype as described herein. The techniques of the present invention may be used to identify desirable disease-resistant phenotypes coupled with a desired bulb color by identifying genetic markers associated with such a phenotype or phenotypes, or such techniques may employ phenotypic assays to identify desired plants either alone or in combination with genetic assays, thereby also identifying a marker genotype associated with the trait that may be used for production of new varieties with the methods described herein.

The invention provides for the introgression of at least a first locus conferring disease resistance coupled with a desired bulb color into a given genetic background. Successful onion production depends on attention to various horticultural practices. These include soil management with special attention to proper fertilization, crop establishment with appropriate spacing, weed control, and the introduction of bees or other insects for pollination, irrigation, and pest management. Onion crops can be established from seed or from starter bulbs, among other methods known in the art. Starter bulbs can result in an earlier crop compared with a crop produced from direct seeding.

Development of Onion Plants with Disease Resistance Coupled with a Desired Bulb Color The present disclosure identifies quantitative trait loci (QTL) with major influence on disease resistance of onion plants and QTL with major influence on bulb color, as well as markers genetically linked to and predictive of such loci that can be used for the tracking and introgression of the QTL into desirable germplasm, such as by marker-assisted selection (MAS) and/or marker-assisted backcrossing. The invention also provides for introgression of a single locus conferring disease resistance coupled with a desirable bulb color. Such desirable bulb color may be conferred by a bulb color locus as described herein or known in the art or by a lack of a locus for CP. An onion plant of the present invention may also be produced by introgressing one or more QTL conferring disease resistance into an onion plant comprising a desired bulb color to produce an onion plant with both disease resistance and desired bulb color.

As described in the Examples, five QTL were identified for disease resistance to FBR and PR, along with three loci controlling bulb color and/or CP. One of these color loci was found to colocalize with a marker in a candidate gene from the anthocyanin biosynthesis pathway. The main effect QTL for both FBR and PR localized to a similar region on LG2, where one of the loci for complementary pinks has also been localized. These mapping results verify a linkage of FBR, PR, and the CP trait, and why it has been difficult to combine resistance of these diseases without CP during onion breeding. QTL intervals and markers for these disease traits may now be used to develop new onion lines and varieties. In an embodiment, novel cis-coupling linkages, for example on LG2 as described herein, allows the combination of disease resistance in donor onion lines such as North American yellow and Universal Yellow, among others.

The present invention contemplates the tracking and introduction of such QTL and any combinations thereof into a given genetic background. One of ordinary skill will understand that resistance to one or more diseases conferred by this QTL may be introgressed from one genotype to another using a locus described herein via MAS. Accordingly, an onion germplasm source can be selected that has resistance to one or more diseases. Using this QTL, a breeder may select an onion plant with resistance to disease or with resistance to disease coupled with a desirable bulb color, or track such phenotypes during breeding using MAS for the region described herein. Provided with the present disclosure, one of ordinary skill can introduce resistance to one or more diseases coupled with desired bulb color into any genetic background.

QTL identified herein may be used for MAS for resistance to one or more diseases coupled with a desired bulb color in onion. This discovery of a QTL associated with disease resistance coupled with a desired bulb color may facilitate the development of commercially valuable onion plants or varieties thereof having resistance to multiple diseases.

For most breeding objectives, commercial breeders may work within germplasm that is often referred to as the "cultivated type" or "elite." This germplasm is easier to use in plant breeding because it generally performs well when evaluated for horticultural performance. The performance advantage a cultivated type provides is sometimes offset by a lack of allelic diversity. This is the tradeoff a breeder accepts when working with cultivated germplasm-better overall performance, but a lack of allelic diversity. Breeders generally accept this tradeoff because progress is faster when working with cultivated material than when breeding with genetically diverse sources.

In contrast, when a breeder makes either intra-specific crosses, or inter-specific crosses, a converse trade off occurs. In these examples, a breeder typically crosses cultivated germplasm with a non-cultivated type. In such crosses, the breeder may gain access to novel alleles from the non-cultivated type, but may have to overcome the genetic drag associated with the donor parent. Because of the difficulty with this breeding strategy, this approach often fails because of fertility and fecundity problems. The difficulty with this breeding approach extends to many crops, and is exemplified with an important disease-resistant phenotype that was first described in tomato in 1944 (Smith, *Proc. Am. Soc. Hort. Sci.* 44:413-16). In this cross, nematode disease resistance was transferred from *L. peruvianum* (PI128657) into a cultivated tomato. Despite intensive breeding, it was not until the mid-1970's before breeders could overcome the genetic drag and release successful lines carrying this trait. Indeed, even today, tomato breeders deliver this disease resistance gene to a hybrid variety from only one parent.

To date, the process of introgressing novel resistance genes into acceptable commercial types is a long and often arduous process and can be difficult because the trait may be polygenic, or have low heritability, or have linkage drag or some combination thereof. While some phenotypes are determined by the genotype at one locus, most variation observed in nature is continuous. Unlike simply inherited traits, continuous variation can be the result of polygenic inheritance, and may be difficult to track. Loci that affect continuous variation are referred to as QTL. Variation in the phenotype of a quantitative trait is the result of the allelic composition at the QTL and the environmental effect. The heritability of a trait is the proportion of the phenotypic variation attributed to the genetic variance, which varies between 0 and 1.0. Thus, a trait with heritability near 1.0 is not greatly affected by the environment. Those skilled in the art recognize the importance of creating commercial lines with high heritability horticultural traits because these cultivars will allow growers to produce a crop with uniform market specifications.

Genomic Region, QTL, Polymorphic Nucleic Acids, and Alleles Associated with Disease Resistance and Favorable Bulb Color in Onion Markers useful for the present invention can be designed from the onion genome. Duangjit et al. published the most recent publicly available genetic map of the onion genome (*Theor Appl Genet* 126(8):2093-2101, 2013). Applicants have discovered genomic regions, QTL, alleles, polymorphic nucleic acids, linked markers, and the like that when present in certain allelic forms are associated with disease resistance and favorable bulb color in onion. Using the methods outlined herein, QTL were identified in onion for resistance to *Fusarium* Basal Rot (FBR) and Pink Root (PR), while also exhibiting a favorable bulb color. Genomic regions associated with such traits were located at onion linkage group 2 (LG2) defined by loci NQ0345038 (SEQ ID NO:3) and NQ0257326 (SEQ ID NO:23); at LG2 defined by loci NQ0257277 (SEQ ID NO:22) and NQ0258453 (SEQ ID NO:27); at LG2 defined by loci NQ0257220 (SEQ ID NO:26) and NQ0257692 (SEQ ID NO:29); at LG3 defined by loci NQ0258523 SEQ ID NO:30) and NQ0345206 SEQ ID NO:36); at LG4 defined by loci NQ0345564 SEQ ID NO:38) and NQ0257917 SEQ ID NO:63); at LG4 defined by loci NQ0344978 SEQ ID NO:49) and NQ0344766 SEQ ID NO:55); at LG 4 defined by loci NQ0258361 SEQ ID NO:37) and NQ0344778 SEQ ID NO:61); or at LG6 defined by loci NQ0257378 SEQ ID NO:64) and NQ0345734 SEQ ID NO:74).

Certain of the various embodiments of the present disclosure utilize a QTL or polymorphic nucleic acid marker or allele located at or within such genomic regions. Flanking markers on LG2 that identify a genomic region associated with resistance to multiple diseases or favorable bulb color include NQ0345038 (SEQ ID NO:3) and NQ0257692 (SEQ ID NO:29). Intervening markers on LG2 that identify a genomic region associated with resistance to multiple diseases or favorable bulb color may include at least any of SEQ ID NOs:4-28. Flanking markers on LG3 that identify a genomic region associated with resistance to disease or favorable bulb color include NQ0258523 (SEQ ID NO:30) and NQ0345206 (SEQ ID NO:36). Intervening markers on LG3 that identify a genomic region associated with resistance to disease or favorable bulb color may include at least any of SEQ ID NOs:31-35. Flanking markers on LG4 that identify a genomic region associated with resistance to multiple diseases or favorable bulb color include NQ0258361 (SEQ ID NO:37) and NQ0257917 (SEQ ID NO:63). Intervening markers on LG4 that identify a genomic region associated with resistance to multiple diseases or favorable bulb color may include at least any of SEQ ID NOs:38-62. Flanking markers on LG6 that identify a genomic region associated with resistance to disease or favorable bulb color include NQ0257378 (SEQ ID NO:64) and NQ0345734 (SEQ ID NO:74). Intervening markers on LG6 that identify a genomic region associated with resistance to disease or favorable bulb color may include at least any of SEQ ID NOs:65-73. These genomic regions, or subregions thereof, associated with disease resistance and/or favorable bulb color can be described as being flanked by or defined by any of the markers described herein, although one of skill will recognize that additional markers may be used, as well.

The above markers and allelic states are exemplary. One of skill in the art would recognize how to identify onion plants with other polymorphic nucleic acid markers and allelic states thereof related to disease resistance or desirable bulb color in onion consistent with the present disclosure. One of skill in the art would also know how to identify the allelic state of other polymorphic nucleic acid markers located in the genomic region(s) or linked to the QTL or other markers identified herein, to determine their association with disease resistance or desirable bulb color in onion.

One of skill in the art would understand that polymorphic nucleic acids that are located in the genomic region(s) identified may be used in certain embodiments of the methods of the invention. Given the provisions herein of a genomic region, QTL, and polymorphic markers identified herein, additional markers located either within or near a genomic region described herein that are associated with the phenotype may be obtained by typing new markers in various germplasm. The genomic region, QTL, and polymorphic markers identified herein can also be mapped relative to any publicly available physical or genetic map to place the region described herein on such map. One of skill in the art would also understand that additional polymorphic nucleic acids that are genetically linked to the QTL associated with disease resistance or desirable bulb color in onion and that map within about 40 cM, 20 cM, 10 cM, 5 cM, or 1 cM of the QTL or the markers associated with disease resistance or desirable bulb color in onion may also be used.

Introgression of a Genomic Locus Associated with Disease Resistance and/or Desirable Bulb Color in Onion Provided herein are onion plants comprising one or more introgressed genomic regions associated with disease resistance and/or desirable bulb color and methods of obtaining the same. Marker-assisted introgression involves the transfer of a chromosomal region, defined by one or more markers, from one germplasm to a second germplasm. Offspring of a cross that contain the introgressed genomic region can be identified by the combination of markers characteristic of the desired introgressed genomic region from a first germplasm (e.g., germplasm with disease resistance or desirable bulb color in onion) and both linked and unlinked markers characteristic of the desired genetic background of a second germplasm.

Flanking markers that fall on both the telomere proximal end and the centromere proximal end of any of these genomic intervals may be useful in a variety of breeding efforts that include, but are not limited to, introgression of genomic regions associated with disease resistance coupled with a desirable bulb color in onion into a genetic background comprising markers associated with germplasm that ordinarily contains a genotype associated with another phenotype.

Markers that are linked and either immediately adjacent or adjacent to the identified disease resistance and/or desirable bulb color QTL that permit introgression of the QTL in the absence of extraneous linked DNA from the source germplasm containing the QTL are provided herewith. Those of skill in the art will appreciate that when seeking to introgress a smaller genomic region comprising a QTL associated with disease resistance and/or desirable bulb color in onion described herein, that any of the telomere proximal or centromere proximal markers that are immediately adjacent to a larger genomic region comprising the QTL can be used to introgress that smaller genomic region.

A marker within about 40 cM of a marker of a disease resistance QTL or desirable bulb color QTL described herein, for example, may be useful in a variety of breeding efforts that include, but are not limited to, introgression of genomic regions associated with disease resistance coupled with a desirable bulb color in onion into a genetic background comprising markers associated with germplasm that ordinarily contains a genotype associated with another phenotype. For example, a marker within 40 cM, 20 cM, 15 cM, 10 cM, 5 cM, 2 cM, or 1 cM or less of a disease resistance QTL or desirable bulb color QTL or marker described herein can be used for marker-assisted introgression of disease resistance coupled with a desirable bulb color in onion.

A marker in linkage disequilibrium with a disease resistance or desirable bulb color phenotype QTL marker on LG2, LG3, LG4, and/or LG6 described herein can thus be used for marker-assisted introgression of disease resistance or desirable bulb color in onion. For example, a marker within 40 cM, 20 cM, 15 cM, 10 cM, 5 cM, 2 cM, or 1 cM of a disease resistance or desirable bulb color QTL marker on LG2, LG3, LG4, and/or LG6 as described herein can be used for marker-assisted introgression of disease resistance or desirable bulb color. As described above, a disease resistance or desirable bulb color QTL marker on LG2, LG3, LG4, and/or LG6 may include one or more of SEQ ID NO:1-74 or any loci or sub-regions described herein, as well as other known markers in those same regions and that are genetically linked thereto.

Molecular Assisted Breeding Techniques

Genetic markers that can be used in the practice of the present invention include, but are not limited to, Restriction Fragment Length Polymorphisms (RFLP), Amplified Fragment Length Polymorphisms (AFLP), Simple Sequence Repeats (SSR), simple sequence length polymorphisms (SSLPs), Single Nucleotide Polymorphisms (SNP), Insertion/Deletion Polymorphisms (Indels), Variable Number Tandem Repeats (VNTR), and Random Amplified Polymorphic DNA (RAPD), isozymes, and others known to those skilled in the art. Marker discovery and development in crops provides the initial framework for applications to marker-assisted breeding activities (U.S. Patent Pub. Nos.: 2005/0204780, 2005/0216545, 2005/0218305, and 2006/0050438). The resulting "genetic map" is the representation of the relative position of characterized loci (polymorphic nucleic acid markers or any other locus for which alleles can be identified) to each other.

Polymorphisms comprising as little as a single nucleotide change can be assayed in a number of ways. For example, detection can be made by electrophoretic techniques including a single strand conformational polymorphism (Orita et al., Genomics 8(2):271-278, 1989), denaturing gradient gel electrophoresis (Myers, EPO 0273085, 1985), or cleavage fragment length polymorphisms (Life Technologies, Inc., Gathersberg, Md. 20877), but the widespread availability of DNA sequencing machines often makes it easier to just sequence amplified products directly. Once the polymorphic sequence difference is known, rapid assays can be designed for progeny testing, typically involving some version of PCR amplification of specific alleles (PASA, Sommer, et al., Biotechniques 12(1):82-87, 1992), or PCR amplification of multiple specific alleles (PAMSA, Dutton and Sommer, Biotechniques, 11(6):700-7002, 1991).

As a set, polymorphic markers serve as a useful tool for fingerprinting plants to inform the degree of identity of lines or varieties (U.S. Pat. No. 6,207,367). These markers form the basis for determining associations with phenotypes and can be used to drive genetic gain. In certain embodiments of methods of the invention, polymorphic nucleic acids can be used to detect in an onion plant a genotype associated with disease resistance coupled with a desirable bulb color, identify an onion plant with a genotype associated with disease resistance coupled with a desirable bulb color, and to select an onion plant with a genotype associated with disease resistance coupled with a desirable bulb color. In certain embodiments of methods of the invention, polymorphic nucleic acids can be used to produce an onion plant that comprises in its genome an introgressed locus associated with disease resistance coupled with a desirable bulb color. In certain embodiments of the invention, polymorphic nucleic acids can be used to breed progeny onion plants comprising a locus associated with disease resistance coupled with a desirable bulb color.

Certain genetic markers may include "dominant" or "codominant" markers. "Codominant" markers reveal the presence of two or more alleles (two per diploid individual). "Dominant" markers reveal the presence of only a single allele. Markers are preferably inherited in codominant fashion so that the presence of both alleles at a diploid locus, or multiple alleles in triploid or tetraploid loci, are readily detectable, and they are free of environmental variation, i.e., their heritability is 1. A marker genotype typically comprises two marker alleles at each locus in a diploid organism. The marker allelic composition of each locus can be either homozygous or heterozygous. Homozygosity is a condition where both alleles at a locus are characterized by the same nucleotide sequence. Heterozygosity refers to different conditions of the allele at a locus.

Nucleic acid-based analyses for determining the presence or absence of the genetic polymorphism (i.e. for genotyping) can be used in breeding programs for identification, selection, introgression, and the like. A wide variety of genetic markers for the analysis of genetic polymorphisms are available and known to those of skill in the art. The analysis may be used to select for genes, portions of genes, QTL, alleles, or genomic regions that comprise or are linked to a genetic marker that is linked to or associated with a disease resistance or desirable bulb color phenotype.

As used herein, nucleic acid analysis methods include, but are not limited to, PCR-based detection methods (for example, TaqMan assays), microarray methods, mass spectrometry-based methods and/or nucleic acid sequencing methods, including whole genome sequencing. In certain embodiments, the detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means.

The use of TaqMan® probes in PCR is known in the art (see, for example, Holland et al., *PNAS* 88:7276-7280, 1991) and allows for increased specificity of PCR assays by fluorophore-based detection. In an embodiment of the invention, TaqMan® probes such as those set forth in Table 3 can be used to detect SNPs conferring disease resistance. TaqMan® assays use two specific primers that target a region flanking a SNP site and two fluorescent probes, each labeled with a different fluorophore (VIC or 6-FAM) covalently linked to the 5' end of the probe. A non-fluorescent quencher near the 3' end prevents liberation of the fluorescence if the probe is not degraded. During PCR, probes that hybridize specifically to DNA fragments are destroyed and the fluorescence of corresponding fluorophore is liberated.

One method of achieving such amplification employs the polymerase chain reaction (PCR) (Mullis et al. 1986 Cold Spring Harbor Symp. Quant. Biol. 51:263-273; European Patent 50,424; European Patent 84,796; European Patent 258,017; European Patent 237,362; European Patent 201, 184; U.S. Pat. Nos. 4,683,202; 4,582,788; and 4,683,194), using primer pairs that are capable of hybridizing to the proximal sequences that define a polymorphism in its double-stranded form. Methods for typing DNA based on mass spectrometry can also be used. Such methods are disclosed in U.S. Pat. Nos. 6,613,509 and 6,503,710, and references found therein.

Polymorphisms in DNA sequences can be detected or typed by a variety of effective methods well known in the art including, but not limited to, those disclosed in U.S. Pat. Nos. 5,468,613; 5,217,863; 5,210,015; 5,876,930; 6,030, 787; 6,004,744; 6,013,431; 5,595,890; 5,762,876; 5,945, 283; 5,468,613; 6,090,558; 5,800,944; 5,616,464; 7,312, 039; 7,238,476; 7,297,485; 7,282,355; 7,270,981 and 7,250, 252 all of which are incorporated herein by reference in their entireties. However, the compositions and methods of the present invention can be used in conjunction with any polymorphism typing method to type polymorphisms in genomic DNA samples. These genomic DNA samples used include but are not limited to genomic DNA isolated directly from a plant, cloned genomic DNA, or amplified genomic DNA.

For instance, polymorphisms in DNA sequences can be detected by hybridization to allele-specific oligonucleotide (ASO) probes as disclosed in U.S. Pat. Nos. 5,468,613 and 5,217,863. U.S. Pat. No. 5,468,613 discloses allele specific oligonucleotide hybridizations where single or multiple nucleotide variations in nucleic acid sequence can be detected in nucleic acids by a process in which the sequence containing the nucleotide variation is amplified, spotted on a membrane and treated with a labeled sequence-specific oligonucleotide probe.

Target nucleic acid sequence can also be detected by probe ligation methods as disclosed in U.S. Pat. No. 5,800, 944 where sequence of interest is amplified and hybridized to probes followed by ligation to detect a labeled part of the probe.

Microarrays can also be used for polymorphism detection, wherein oligonucleotide probe sets are assembled in an overlapping fashion to represent a single sequence such that a difference in the target sequence at one point would result in partial probe hybridization (Borevitz et al., *Genome Res.* 13:513-523, 2003; Cui et al., *Bioinformatics* 21:3852-3858, 2005). On any one microarray, it is expected there will be a plurality of target sequences, which may represent genes and/or noncoding regions wherein each target sequence is represented by a series of overlapping oligonucleotides, rather than by a single probe. This platform provides for high throughput screening of a plurality of polymorphisms. Typing of target sequences by microarray-based methods is disclosed in U.S. Pat. Nos. 6,799,122; 6,913,879; and 6,996, 476.

Target nucleic acid sequence can also be detected by probe linking methods as disclosed in U.S. Pat. No. 5,616, 464, employing at least one pair of probes having sequences homologous to adjacent portions of the target nucleic acid sequence and having side chains which non-covalently bind to form a stem upon base pairing of the probes to the target nucleic acid sequence. At least one of the side chains has a photoactivatable group which can form a covalent cross-link with the other side chain member of the stem.

Other methods for detecting SNPs and Indels include single base extension (SBE) methods. Examples of SBE methods include, but are not limited, to those disclosed in U.S. Pat. Nos. 6,004,744; 6,013,431; 5,595,890; 5,762,876; and 5,945,283. SBE methods are based on extension of a nucleotide primer that is adjacent to a polymorphism to incorporate a detectable nucleotide residue upon extension of the primer. In certain embodiments, the SBE method uses three synthetic oligonucleotides. Two of the oligonucleotides serve as PCR primers and are complementary to sequence of the locus of genomic DNA which flanks a region containing the polymorphism to be assayed. Following amplification of the region of the genome containing the polymorphism, the PCR product is mixed with the third oligonucleotide (called an extension primer) which is designed to hybridize to the amplified DNA adjacent to the polymorphism in the presence of DNA polymerase and two differentially labeled dideoxynucleosidetriphosphates. If the polymorphism is present on the template, one of the labeled dideoxynucleosidetriphosphates can be added to the primer in a single base chain extension. The allele present is then inferred by determining which of the two differential labels was added to the extension primer. Homozygous samples will result in only one of the two labeled bases being incorporated and thus only one of the two labels will be detected. Heterozygous samples have both alleles present, and will thus direct incorporation of both labels (into different molecules of the extension primer) and thus both labels will be detected.

In another method for detecting polymorphisms, SNPs and Indels can be detected by methods disclosed in U.S. Pat. Nos. 5,210,015; 5,876,930; and 6,030,787 in which an oligonucleotide probe having a 5' fluorescent reporter dye and a 3' quencher dye covalently linked to the 5' and 3' ends of the probe. When the probe is intact, the proximity of the reporter dye to the quencher dye results in the suppression of the reporter dye fluorescence, e.g. by Forster-type energy transfer. During PCR, forward and reverse primers hybridize to a specific sequence of the target DNA flanking a polymorphism while the hybridization probe hybridizes to polymorphism-containing sequence within the amplified PCR product. In the subsequent PCR cycle DNA polymerase with 5'→3' exonuclease activity cleaves the probe and separates the reporter dye from the quencher dye resulting in increased fluorescence of the reporter.

In another embodiment, the locus or loci of interest can be directly sequenced using nucleic acid sequencing technologies. Methods for nucleic acid sequencing are known in the art and include technologies provided by 454 Life Sciences (Branford, Conn.), Agencourt Bioscience (Beverly, Mass.), Applied Biosystems (Foster City, Calif.), LI-COR Biosciences (Lincoln, Nebr.), NimbleGen Systems (Madison, Wis.), Illumina (San Diego, Calif.), and VisiGen Biotechnologies (Houston, Tex.). Such nucleic acid sequencing technologies comprise formats such as parallel bead arrays, sequencing by ligation, capillary electrophoresis, electronic microchips, "biochips," microarrays, parallel microchips, and single-molecule arrays, as reviewed by R. F. Service Science 2006 311:1544-1546.

The markers to be used in the methods of the present invention should preferably be diagnostic of origin in order for inferences to be made about subsequent populations. Experience to date suggests that SNP markers may be ideal for mapping because the likelihood that a particular SNP allele is derived from independent origins in the extant populations of a particular species is very low. As such, SNP markers appear to be useful for tracking and assisting introgression of QTLs.

Definitions

The following definitions are provided to better define the present invention and to guide those of ordinary skill in the art in the practice of the present invention. Unless otherwise noted, terms are to be understood according to conventional usage by those of ordinary skill in the relevant art.

As used herein, a "desired bulb color" or "desirable bulb color" or "favorable bulb color" refers to an onion bulb that exhibits a commercially acceptable color such as yellow, and/or that lacks a deleterious or undesirable color, such as that conferred by complementary pinks (CP).

As used herein, the term "plant" includes plant cells, plant protoplasts, plant cells of tissue culture from which onion plants can be regenerated, plant calli, plant clumps and plant cells that are intact in plants or parts of plants such as pollen, flowers, seeds, leaves, stems, and the like.

As used herein, the term "population" means a genetically heterogeneous collection of plants that share a common parental derivation.

As used herein, the terms "variety" and "cultivar" mean a group of similar plants that by their genetic pedigrees and performance can be identified from other varieties within the same species.

As used herein, an "allele" refers to one of two or more alternative forms of a genomic sequence at a given locus on a chromosome.

A "Quantitative Trait Locus (QTL)" is a chromosomal location that encodes for at least a first allele that affects the expressivity of a phenotype.

As used herein, "repulsion" or "repulsion phase" refers to the inheritance of alleles from two genes, where the desired allele at each of the two genetic loci are found on different homologous chromosomes. This may also be referred to as a "trans" configuration of alleles.

As used herein, a "marker" means a detectable characteristic that can be used to discriminate between organisms. Examples of such characteristics include, but are not limited to, genetic markers, biochemical markers, metabolites, morphological characteristics, and agronomic characteristics.

As used herein, the term "phenotype" means the detectable characteristics of a cell or organism that can be influenced by gene expression.

As used herein, the term "genotype" means the specific allelic makeup of a plant.

As used herein, the term "introgressed," when used in reference to a genetic locus, refers to a genetic locus that has been introduced into a new genetic background, such as through backcrossing. Introgression of a genetic locus can thus be achieved through plant breeding methods and/or by molecular genetic methods. Such molecular genetic methods include, but are not limited to, various plant transformation techniques and/or methods that provide for homologous recombination, non-homologous recombination, site-specific recombination, and/or genomic modifications that provide for locus substitution or locus conversion.

As used herein, the term "linked," when used in the context of nucleic acid markers and/or genomic regions, means that the markers and/or genomic regions are located on the same linkage group or chromosome such that they tend to segregate together at meiosis.

As used herein, the term "denoting" when used in reference to a plant genotype refers to any method whereby a plant is indicated to have a certain genotype. This includes any means of identification of a plant having a certain genotype. Indication of a certain genotype may include, but is not limited to, any entry into any type of written or electronic medium or database whereby the plant's genotype is provided. Indications of a certain genotype may also include, but are not limited to, any method where a plant is physically marked or tagged. Illustrative examples of physical marking or tags useful in the invention include, but are not limited to, a barcode, a radio-frequency identification (RFID), a label, or the like.

Deposit Information

A deposit of onion line SYG-75-1706 has been made with the Provasoli-Guillard National Center for Marine Algae and Microbiota (NCMA), 60 Bigelow Drive, East Boothbay, Me. 04544, USA. The date of deposit for onion line SYG-75-1706 was Dec. 21, 2021. The accession number for the deposited seeds of onion line SYG-75-1706 is NCMA Accession Number 202112015. Upon issuance of a patent, all restrictions upon the deposit will be removed, and the deposit is intended to meet all of the requirements of 37 C.F.R. §§ 1.801-1.809. The deposit has been accepted under the Budapest Treaty will be maintained in the depository for a period of 30 years, 5 years after the last request, or the effective life of the patent, whichever is longer, and will be replaced if necessary during that period.

EXAMPLES

The following disclosed embodiments are merely representative of the invention which may be embodied in various forms. Thus, specific structural, functional, and procedural details disclosed in the following examples are not to be interpreted as limiting.

Example 1

Disease Mapping in Onion

A large F2:3 mapping population (approximately 620 families, selectively phenotyped across diseases) from the origin onion line SYG-75-1706/Serrana was created and phenotyped for various traits. This resulted in the identification of QTL for two important diseases in Onion:

*Fusarium* Basal Rot (FBR) and Pink Root (PR). Several major QTL for these traits were identified (Table 1), based on phenotyping conducted in Deforest, Wis. (inoculated seedling growth chamber test for FBR and PR) and Donna, Tex. (mature plant/bulb field evaluation for PR). Most notably, FBR and PR resistance mapped in repulsion phase to a similar region on linkage group 2 (LG2), in a genetic location where a third detrimental trait for complementary pinks (mapping to position 62.5 on LG2) has also been mapped in this population. This repulsion linkage with complementary pinks was considered as a reason FBR resistance from the landrace donor Serrana has been very difficult to breed into elite onion germplasm. An effort was thus undertaken to link FBR resistance, PR resistance, and a bulb color locus in the correct phase for simultaneous introgression into breeding programs. Identified QTL from this effort are given in Table 1 below.

maps to the same region on LG6 and is suspected to be the R locus controlling bulb color.

In a second, elite×elite F2 mapping population (SWL-74-14197-DH/HRL-77-5225B) segregating for bulb color (segregating for yellow, white, red, pink bulbs), two QTL were identified for bulb color. Parent SWL-74-14197 is white-bulbed, and HRL-77-5225B is red-bulbed. A QTL on LG4 at ~53 cM appears to control the production/inhibition of color pigments, while the QTL on LG6 at ~22.4 cM gene appears to control red pigment production.

The LG6 loci for color of both CP and bulb color appears to be the same in both populations/traits, and is likely the R locus or DFR gene on which a marker from this candidate gene for the anthocyanin biosynthesis pathway maps (NACEP009089369 and NACEP009090969, mapping to LG6: 22.3 cM and 22.6 cM, respectively).

TABLE 1

Summary of Significant QTL Detected for Onion Disease and Color Traits.

| Trait | Resistance donor parent allele | QTL Linkage Group (LG) location & position | LOD | 1-LOD interval (cM) | 2-LOD interval (cM) | Most significant marker/s | Additive effect (%) |
|---|---|---|---|---|---|---|---|
| FBR | Serrana | LG 2: 46.9 cM | 14.7 | 41.9-54.9 | 40.9-61.9 | NQ0258383 | 6.8 |
| FBR | Serrana | LG 3: 52.1 cM | 4.6 | 38.1-60.9 | 34.1-86.1 | NQ0257455 | 2.3 |
| FBR | Serrana | LG 4: 44.8 cM | 2.8 | 22.7-92.7 | 21.7-101.7 | NQ0257799 | 3.3 |
| PR | SYG-75-1706 | LG 2: 57.9 cM | 17.7 | 53.9-60.9 | 53.5-61.9 | NQ0257570 | 32.4 |
| PR | Serrana | LG 4: 51.7 cM | 5.8 | 46.7-56.3 | 38.7-60.7 | NQ0345680 | 10.8 |
| Bulb Color LG6 | | LG 6: 22 cM | | 4.6-33.6* | | NACEP009089369*, NQ0258009*, NQ0344415*, NACEP009090969* | |
| Bulb Color LG4 | | LG 4: 52.0-53.6 cM | | 17.0-82.8* | | NQ0344496*, NQ0345333* | |
| Bulb Color LG2 | | LG 2: 62.5-63.1 cM | | | | NQ0258453*, NACEP009407370/NQ0257461* | |

*denotes significance at p-value <0.05

In addition to the above QTL study, PR resistance was mapped as a binary trait in the same population (SYG-75-1706/Serrana), as it behaves as expected for a single gene under incomplete dominant control. Binary mapping confirmed the position of PR resistance on LG2 at 56.3 cM.

Example 2

Bulb Color Mapping in Onion

Three loci controlling color in onion were mapped to LG2, LG4, and LG6. Complementary Pinks (CP), which has been reported to be controlled by two epistatic loci, was mapped to LG6 and LG2 in the same SYG-75-1706/Serrana population as described in Example 1. Complementary Pinks is a bulb color phenomenon that manifests itself in wide crosses involving elite onion lines and certain more exotic germplasm. This traditionally has created a barrier to accessing certain disease resistances, such as FBR, which is present in Brazilian onion landraces such as Serrana. The CP loci were mapped as a binary trait (yellow vs. pink bulb phenotype) to the positions of LG6: ~22.4 cM and LG2: ~62.5 cM. A candidate gene marker based off of the dihydroflavonol 4-reductase (DFR) gene was developed and Example 3

Cis-Coupling Linkage of FBR, PR, and Color

Within the SYG-75-1706/Serrana F2:3 population, the opportunity exists to combine FBR resistance with PR resistance, in both a North American yellow and Universal yellow onion line. With the identification of the major QTL/genes underlying color and disease resistance, phenotype and genotype information can be used to identify those recombinant families that can be used to couple the traits. Novel cis-coupling events have been identified, that have combined multiple disease resistances together onto a continuous haplotype stretch of linkage group 2. Based on the QTL information, the following haplotype is considered the most desirable configuration for obtaining a high level of FBR and PR resistance in a universal yellow bulb (i.e. a single onion line with resistance to FBR, PR, and a lack of CP). A universal yellow bulb is beneficial because it can be crossed with both North American and South American germplasm, and not produce (complementary) pink bulbs. A double recombination event on LG2 is required to obtain this phenotype (FIG. 1). A North American yellow donor is also desirable, as this germplasm will not produce CP when crossed to North American germplasm. A North America yellow is defined by a 1706 allele on LG2 (position 62-63), and only requires a single recombination on linkage group 2.

Thus, five QTL for disease resistance to FBR and PR, along with three loci controlling bulb color and/or CP were identified. One of these color loci was found to colocalize with a marker in a candidate gene from the anthocyanin biosynthesis pathway. The main effect QTL for both FBR and PR localized to a similar region on LG2, where one of the loci for complementary pinks has also been placed. These mapping results verify the suspected linkage of FBR, PR and complementary pinks, and thus why it has been difficult to combine all traits in breeding. Overall, this information provides insight into genetic control of these key onion traits, and now allows a more controlled approach to combining all traits into elite onion lines. QTL intervals and markers for these disease traits have been enabled for use in new developmental crosses and resulting segregating populations in a HAPQTL MAS approach. Further, event creation may enable the creation of novel cis-coupling linkages on LG2 to combine FBR and PR resistance in both a North American yellow and Universal Yellow bulbed donor. Recombination events combining FBR and PR in a North American yellow have also been accomplished.

Example 4

Marker Details for Marker-Assisted Selection

Based on the QTL results and intervals, markers have been provided herein for important disease resistance loci for a HAP QTL approach in new developmental crosses. As outlined in FIG. 2, onion breeding is amenable to a HAP QTL approach. Since developmental cross cages are composed of a single plant×single plant crossing pattern, parental marker genotypes for each plant going into a respective developmental cross can be obtained. Parental genotypes can be obtained using a core set of markers that are in trait regions that are considered potential targets for marker-assisted selection (MAS) (identified as "Master Loci" in FIG. 2). Therefore, per cage, a select number of the same polymorphic markers (identified on a bi-parental basis) can be used for both true F1 identification in fertile×fertile (F×F) crosses, as well as for subsequent trait MAS in segregating populations that are segregating for the trait of interest. This enables mainstream breeding workflow. Table 2 provides an example list of markers that can be used for MAS and F×F workflow. These marker sequences were used to develop Taqman® assays for use in a high throughput laboratory set up (Table 3). These markers are intended to serve as markers in the "Master Loci," which can be used for parental genotyping in new developmental crosses, with subsequent polymorphic markers identified that can be used to identify respective F1's in F×F screening and also MAS selection in the resulting segregating generations (typically F1M1).

TABLE 2

List of markers for MAS and FxF workflow.

| SEQ ID NO | Marker | LG | Position | Allele of SYG-75-1706 | Allele of SERRANA | DNA Sequence |
|---|---|---|---|---|---|---|
| 1 | NQ0257512 | 2 | 40.84 | C | G | AAGGTTTGTAACCAAACTCTGACCTTAGATGTTATGATTGTGTGCACAAGCTCTACTCTT[C/G]CAGCAAAnGATAGCAATTTGGATCTCCAACCnTCCAACTTCTCTCTAATATATATAnAA |
| 2 | NQ0345493 | 2 | 41.00 | C | T | GCCTTCTCTTCGATTTTTCATTGACGAAGGTGATGATGCTTTGCCGAATGATCCAATGCT[T/C]TTCCATACTAAAAGAACCTACCAGCCTAGCACTATCAAACGCAAGAGGACTCATGGTTAT |
| 3 | NQ0345038 | 2 | 41.33 | G | A | GCGGAAGGTCGCGATCCTCGGGGCCGCTGGGGnATTGGGCAGCCTTTGTCACTTCTGAT[A/G]AAGCTTAATCCTCTTGTTACCAAGCTAGCTCTTTATGATATTGCTGGTACTCCTGGCGTG |
| 4 | NQ0345495 | 2 | 42.36 | — | — | TTTCTTGACATTGGACGATGCGATCAAGACTACAAATAGGAGGGTTAATGCCTTGGAGAG[T/C]GTTGTCAAACCAAGGTTGGAGAATACCATTACCTATATCAAGGGAGAGCTGGATGAGTTG |
| 5 | NQ0345022 | 2 | 42.53 | C | T | CTCAAAACCACCACCGGTCGCATTAAGCAATGCTAGAGAAAGTATTCTGTTAGGTGCAAT[t/c]GCTGCCAACTTGCAAGCAATCATTGCTCCCATGGAGTGACCAAAAnCATGAGCTTTAGTC |
| 6 | NQ0257948 | 2 | 45.63 | T | C | TTCCCAAGAGATTATGTACCGTGGTCCTCTAGCTCTTTTCGGTGTAGGGCTTGATGATTA[T/C]TTCCCAATGATTAATATATATTATTAATTAACTCAGACTTTGACTGCACTATAGTGTCAC |
| 7 | NQ0258383 | 2 | 47.42 | C | A | ATCAAATAACTTGATGGTTTCTGAGGAATCCCATGATGTCAAATCCGTTTTATTAGCTAA[A/C]GCAAATGACCAGTGCAATTTAGCCATnTCAAAATGTTGCTGTCCAAGTGCAAGTAACCCT |
| 8 | NQ0257610 | 2 | 47.47 | T | A | TGAATCAGAAGGTTCTCTTTGTGCAATTTGTATCCCTGGCATACTATAATATACGAAATG[A/T]AATCATCTCTTATAACCTGGTAGGACATAGGTAGAAAATCTAACTGGATGATTAGCCAAT |

TABLE 2-continued

List of markers for MAS and FxF workflow.

| SEQ ID NO | Marker | LG | Position | Allele of SYG-75-1706 | Allele of SERRANA | DNA Sequence |
|---|---|---|---|---|---|---|
| 9 | NQ0258102 | 2 | 48.51 | — | — | GCTTGAAAACATAGTTAAGCAACTTTTTCCTCAAGCTGG TTGTCAATCTTGGTCACCTAG[A/G]ATGGTACAGCCGATT TGGAAAACAnTATGGGAAACTAAAAnTGCACAATTGAG AGAAGGT |
| 10 | NQ0257924 | 2 | 48.51 | C | C | TTCCATTGCTTCTCTGCCTTTGATCTCCTTCCATTCTTCA GCCCTACTTTGTCACGATT[C/G]TCAAAGCTAGGGTTAGT TTTACTTTTGAATTCGATTTTGAATTCTTAATTCTTATGA TTT |
| 11 | NQ0257757 | 2 | 49.32 | T | C | TCTGGATTGAAAnTTAATGGCAGCAAGGTTGAGAAAGCT GAAGAGAAGGTGGAAAAGATG[t/c]CTGCTTTGACGCTG AAACCAGAGAAGGTTAAAGATGCATCGAAGGCTGAGGC TGTTGTCA |
| 12 | NQ0258031 | 2 | 49.79 | T | C | AATGACAGTAAAATGGAAAATTGTTCAGGTTTGAGCCT GCGGCATCATGCCCTCCAAATA[T/C]GGAGTCCATTTTA ACAATCCTTATTTAGAATTACTTTGGTAAAnnAAGCAGA GAGATTAA |
| 13 | NQ0257938 | 2 | 50.08 | C | T | TTTGGAATTTATAATAGGTAGTGAAAAGAAATGTCTGA ATTCAGAGCTCTGGCATGCATG[T/C]GCTGGACCTCTTGT ATGTTTGCCAACAATCGGGACTCGAGTAGTTTACTTCCC TCAAGGC |
| 14 | NQ0258282 | 2 | 50.08 | C | T | TTCATGCAnGCATAnATTGATGTATGTTGTATGTAAACA ATAACAGTAAGTTTTGTGTTG[T/C]TATTGTAGGTGGAGG GAGAATGCGAAAGAAGCnGTTGAAGAACTGGGAGTTGC TTTGAAA |
| 15 | NQ0258343 | 2 | 50.53 | C | T | CAATCCCACCTACACACATTTCCACACGTTGCATTTT GTGAGTTTATATACTTTCTGT[T/C]GTTATCTTCATAGTC AACCTTGCTTATTTnAACAATAATATAAAAGTGCTTTTG GTAAAA |
| 16 | NQ0258609 | 2 | 51.49 | — | — | TCTTTCGAATGTGTATTCTGAAGTGAACAGATGGGATGA TGCAGAGACGACGAGGATTAG[T/C]ATGAAGAATTGTAA TGTAGATAAATTGCCTGGATGGAGTTGTATAGAGGTTAA TGGAAAG |
| 17 | NQ0257954 | 2 | 51.64 | A | G | CAAAnCATAGCCAACCTCTGCCAGTAAGTTCAACTACCC TCCAAGCACTACCTTTCACCT[a/g]CACTACAGCTACTTC ACCTTCTTCTACCTTCTGCCCGCAAATnCCATCACTACnC CAACC |
| 18 | NQ0257684 | 2 | 52.02 | C | G | GGCTTATGACCAGGCAGCTTTTGCCATGAGGGGGTCGCT GGCAATTTTGAACTTCTCAGT[C/G]GAAACAGTTGTTGA ATCTTTGAGAGAAGTCAAGTGCCTAAAAGCTGGAGGAG AGTCCCCT |
| 19 | NQ0258062 | 2 | 52.07 | G | C | GCTTCAGAAAnCCTTAAGTTTTATTTCTTCTGCATCATCA CCCCCTCTTCCCTATAGTTC[C/G]GATTACTATATTCCCG CCGTACAATTTCCGAAAnCACCTCCAAATCTTACCGTTT CTCAA |
| 20 | NQ0258384 | 2 | 52.07 | C | G | GGCTTATGACCAGGCAGCTTTTGCCATGAGGGGnTCGCT GGCAATTTTGAACTTCTCAGT[C/G]GAAACAGTTGTTGA ATCTTTGAGAGAAGTCAAGTGCCTAAAAGCTGGAGGAG AGTCCCCT |
| 21 | NQ0257410 | 2 | 53.32 | G | C | AGAAAnGAAGAAGAAAAACAATCGAATCCCCTACCTCT TATCAGAACATCGACCCGAACC[C/G]CACAAACCACCCA ATATTCCATTGCCTCATCAAAAATTGCCTCGCCGCCTTC ACCCAGAA |
| 22 | NQ0257277 | 2 | 53.48 | T | C | AATTAAAAnTAAATGGATCACAGACATTAGTATGAAAG CAAGCAATATATAATTAGAATT[T/C]AGGGCTGTTTTGCT AGAAATTTGAGTTTTGCATCTTGCATTTTCAATATGCAT GTTAAAA |

TABLE 2-continued

List of markers for MAS and FxF workflow.

| SEQ ID NO | Marker | LG | Position | Allele of SYG-75-1706 | Allele of SERRANA | DNA Sequence |
|---|---|---|---|---|---|---|
| 23 | NQ0257326 | 2 | 55.14 | C | T | CCTAACCATGGnATTTGTCCAGCTAAGATCCCCTTCAAG AGCAAGATTCTCAATATTTAG[T/C]ATTAGCGGTTTCCCA AACTACACTCAAGATCAGGGCAGGCCCTGTATACTGGG TTGCTCT |
| 24 | NQ0257570 | 2 | 55.59 | C | T | TTAATAAACTGAAAAGGAGGATTCATTCATTCATGTTAA AGTGCATAAAATAATAGATGA[T/C]GATGACGATGATGA TTTGGTTTTCGATTTTCTTACCCTTGCAAAAGCTCGAGA AGCTGTG |
| 25 | NQ0257962 | 2 | 57.17 | C | T | AAAnGAGAAGAGAAAAAAnCATGCCCCTTATCTTGCTAT TTATCTCATTTAATCTCTTAA[T/C]TACTGCATCCGCATCT GATGCAGAGGAATCCCTTCTTAACTGGAGATCGTCTCTT ATAAA |
| 26 | NQ0257220 | 2 | 58.38 | C | C | ATTTCGTTCTAAGGATGGGGAGTGGCACTGTTATGTGGA TAATGCTGTCTGGTACTATGC[t/c]ATGTTATTAGTTGGTG ACAGTTATATTATCATACACTACAAAAATTGCATGGGTT AATTG |
| 27 | NQ0258453 | 2 | 62.51 | G | A | AATTCCTCGGAGATGGATATTCTTCTCTGTAAATAGCCT CGAGATTAAATGGCCTAAATC[A/G]AAACCCATTAACAT ATGATATCCAACAAACAAAGTAGGACCCACAGATGGAA TTCCTTCA |
| 28 | NQ0257461 = NACEP009407370 | 2 | 63.08 | G | A | GTATTCAAGTTGGCCCACGTTTCCTCAACTTTATATTGAT GGGGAGTTTTATGGAGGGTGTGATATTACTGTTGAAGCA TACCAGAGTGGGGAACTGCAGGAAGCAATAGAAAAAG CAATGTGTTCTTAATAATGTCTCAGTTATA[A/G]CCTTCT ATGCTCCATTCATGCAAAGTTACACTTATTTATTAATTAT GTTATTATATAATATATATCTGCAATTTTCATATTTCAGA TCTGTGGATGACACTTACCATTTAGTTGCTTCTGGTGTTT ATATTTATTCTACAAAGACCATTTACTGAGTTTTCAAAT GCT |
| 29 | NQ0257692 | 2 | 69.89 | G | A | CATCTTATAAGTAATATACTTTnAACTTTTAAGGATCTTC AAATATTCTCTTATAAATTA[a/g]AGGCCCCAAGATTAAT CCAAACTGAATTCATAAACAAnTAAAnTATCTATTTnAGT TTCT |
| 30 | NQ0258523 | 3 | 37.78 | T | C | AAGCTGTGATTTGTGCACACTGGTGTGCAGGTGCACTGT GGATAGTAGCAGTTGTTTnAT[t/c]GGGTGATGGCTAGTTT GGACTGTGGTCATTAATGTTTAGAGGCTAAAGCAGCTG GTTGAA |
| 31 | NQ0258354 | 3 | 43.03 | G | A | AAATTAnTTACTGTAAATTCATCAAACCCTAAnTCAATC ATGCAAGTGTGCAATTACACC[A/G]CTCAAGTCCCACCA TCATACAATACTTATCGATTTnGATGACTTTCAAAGTTTA GTGCTA |
| 32 | NQ0257455 | 3 | 45.08 | G | T | TTTGAAGCGGAAAGATATGTCTGTTGTGGTGTCAATGCG CATAATAAAGAAAGCATCAAA[t/g]GGGTAACTACTATTT CAAAATTCATGTATTCAATCATATTGTTTATGGGCTTTC GTCGTG |
| 33 | NQ0257354 | 3 | 50.20 | A | A | TTACTATTAATATCATCCATnTAAACTGTTACGTCATTTC GAAATTTTCATCTCACTAAA[a/c]GGTGCAAATTGATATG ATCCATCGAAAATATTTATTTAACCATCnATTTCAAACG TAGTT |
| 34 | NQ0344514 | 3 | 58.45 | — | — | TTGTCCTAACCCCTAnATCATATAGTATCTGTGCTCCAAT GCCATATTCTCGTGAATCAA[T/C]AGGTAACCCCAAATC TTCGTTGGCTTCCACAGTGTCACGGCCAGCATCTTGCAG ATTATA |
| 35 | NQ0258512 | 3 | 60.87 | — | — | CACTAAAGGATCTGAGCAAACAGCTGTAGAAGTTAATG ATAGTGAAAGTGATTTGAACCG[a/g]ACAATTTTCATAAA CAATATTCCATTTGATGCTGACAGTGAAGAGGTGAAAA AGAGATTC |

TABLE 2-continued

List of markers for MAS and FxF workflow.

| SEQ ID NO | Marker | LG | Position | Allele of SYG-75-1706 | Allele of SERRANA | DNA Sequence |
|---|---|---|---|---|---|---|
| 36 | NQ0345206 | 3 | 62.16 | T | C | TGCAGATCCAAGTAAnTATGGTATTTTTAAATTGATAGC TATCGATTATTTTGGACCTTT[t/c]CTCTTTTCTGCATTTGA TGATTGCAAATGTGTTCTGATATTATTATTTTCATATTT TTA |
| 37 | NQ0258361 | 4 | 17.04021 | — | — | TTTGATGCGCCTAGGACCCCAACTTAAAGAAAGCCACTT TGAACGTGAGAATGATTCTGC[a/g]TATAGTTCATCATTT AGCATCCCnTTCACAAATAATGCAAAACTTCATTCTCA GATTGC |
| 38 | NQ0345564 | 4 | 21.73 | C | T | CGCTTGGCATCAGTACAGTAGTTGTAAATCATGAACTTC CTCTGCACCCACCTCATTCTC[t/c]TGTAACTCACCGAATC CAACTCGTGGTTATACCAATCTGCTGGCGAAGCCGTTGA CAACA |
| 39 | NQ0257741 | 4 | 25.93 | A | G | AnTTAAGGGAGTTTGTGTAAATATCAACAAGGATACGTA GTCCATCACTACTGTCATGGn[a/g]GTTAGACGCTCCGGC TTTGGTCAGTGAAGTTACAGGTTGAATCATGGTAGTGTC ATTCAA |
| 40 | NQ0258022 | 4 | 30.38 | A | A | ATAAAATTGGGATCAGCCAGAAAATGCTGAAACACACCT ATCAACAATTTATACCAGAATC[a/g]CTATTTACAGCCAA CATGCTAGAGGCACTTCAATAAAATGTTTAGACAGATC AGTCATTT |
| 41 | NQ0257641 | 4 | 30.56 | A | G | AAGAATTCACTTGTTGATAGCTTCATTGTCTTGCTGGTTT TCAACTAATCTCATATTCTA[A/G]GTTGCCCTGAAATTAA ATGTAAATGGGAAAAATGTGAAAAGGCAGGTTAGAATC TTATAC |
| 42 | NQ0345175 | 4 | 32.83 | A | G | CTCAATAGGCTTTCTTGGTGAGGCAGAGTAATCGGCATG TCTTCTTGGTGAAGCAGAGTG[A/G]TCAGTTTGCCTTCTT GGTGCAGGAGAGTACGACCTTGATGTATGGCGAGCTCT TGAAGAT |
| 43 | NQ0257421 | 4 | 35.05 | A | C | TAGGTAAAAnTTAAAGAGAAAAGCATCGTAAATAATTA AGTCACAAAGCAGCAGGTGTGT[a/c]GAGTCTACACTAA ACCAATCCTTTAAGAAGTGTACCACTTATATACGATTAA ATGTATTA |
| 44 | NQ0257536 | 4 | 35.60 | C | T | CCTAATTTTTCTCCTCAAATATCCCATTTGTTTCTAACTA AATCTCAAAGGAAAAGCTTT[T/C]ATTGCACGATAACGG TTAATTTAATCATTCTTCAAGCTACACAATCAGTCAATC AGTCGT |
| 45 | NQ0258247 | 4 | 37.98 | G | A | AATTTCGCGATGCATTTGAGATTGTTGTGGAAAnTATGG TGCGTATGGTCACCAAATGAG[A/G]TATACACGATTCCT TTGTAACGATAAATGTTTGGATGACATTCAATTGTAGAA CCACTGA |
| 46 | NQ0257556 | 4 | 40.61 | C | T | AATCTTCCAAATGGTCTAAGTTATACAACCTTAAAGAGC AGCCATATGATTCATGTATAT[t/c]GACTGAGATAAAATG GAAAGGTGCAAGTGGTGGTGGAAATTATAAACATTGCA ACCnTCA |
| 47 | NQ0257799 | 4 | 44.79 | C | T | TTCTATTATTAATAAAAAGAATACTATTATCCTTAAATC AACAATCTTGGAATCCTTTAG[T/C]GAGGCAAAGTTACC GAGTTTCGTTTCTCTTGAACTTGTTACAATAATTACAAA ACCATAC |
| 48 | NQ0344630 | 4 | 45.78 | C | T | CATTTTTAAATATTGGTAATATGCAAACATATTTTAAGA AAATGCCAAGTAGATGAGCCA[t/c]AGAAGATACATTCA ATGTCTCCAATGTAGATTTATTTATTTTTTTTAAAACAAG AGAATA |
| 49 | NQ0344978 | 4 | 46.32 | — | — | ATGTGTTGTTAGATCTGCTTTCTAATTCTCAGGATCGAA AGTCCAATTTCTTGCTACCTT[a/t]TAAAAGAGCTACCAAC GACAGCATTCAAGCTGTTAATGAAGAAGATGACACATC ACGTCC |

TABLE 2-continued

List of markers for MAS and FxF workflow.

| SEQ ID NO | Marker | LG | Position | Allele of SYG-75-1706 | Allele of SERRANA | DNA Sequence |
|---|---|---|---|---|---|---|
| 50 | NQ0345680 | 4 | 49.45 | T | G | GTCTCTGTATAACCAGCCTGGTGCCGCTGGAGCTCCTGG TGGGGCTGACTCAGCTGGACC[T/G]GTGCCTGGTTCGGA ACCTTCTGGAACTTCGGGTGGTAAGGGGCTGAAGATGG TGATGTTA |
| 51 | NQ0345468 | 4 | 50.90 | — | — | AGGAGTTTTGGGCGACGGGAGTGAGATTGCCGTGAAGA AAGTACTGGAATCAGATCTCCA[T/C]GATGATGAATTCA AGAATGAGGTTGAGATAATCAGCAAGTTAAGGCATAGA AATCTTGTT |
| 52 | NQ0345333 | 4 | 52.02 | A | T | AGCCACAACAATAGACCAAAATGnATTTGCTTCTTTTGC ATGACAATATAAAGATGATGC[A/T]TGCTTCTTCAACCA GGCAGCACAAGGATGACCTGTTCCATCGAAGTTATTTTT ACCACTT |
| 53 | NQ0344496 | 4 | 53.59 | A | G | TTCATTCAGGTATTTATCATCTCTGTGGAGTGCTAGCGC ATGACCGATAAAGTCAATTGT[A/G]TTGTCATCCAATCC ATATTTTGATATGAGCTCTTTAGTAGTCACCCTTGTAAG GTCCAAT |
| 54 | NQ0344746 | 4 | 54.31 | C | T | CCTCTGAAATTAAGATACTTTCTGGAGTAGAAACAAGTG AAGCTGCTACTGTTTCAGGTA[T/C]TGGCAGCAGATTCTTC TTCGTCAGAACTATTACCTTCGGATTCTTCTTCTATTGGG TTTTC |
| 55 | NQ0344766 | 4 | 56.31 | T | C | GAAAAGACGACGAATCTGCATTTTCGTCCTGAAAGTT AACGATCGCCAGCCGCCTATCA[T/C]CCTCAGCTTCTTCG ACGTCGCCAAGGGAAGGTGAAGAATCGAACTCGACGTC GGAGTCTG |
| 56 | NQ0258314 | 4 | 61.48 | A | T | TATTGGTAAAAnTAAGTACAAAATATAAGAAGATTAAG TTTAATAATCCTGGTTCCTTTA[a/t]ATTGTCCAGACTCTC CCAAGCAAAACAAGTGAGAAATTAGCATTGGCTTCAAA GTTCAAA |
| 57 | NQ0257998 | 4 | 67.55 | C | C | GATTAGATTTCGAGAATGGAGAAAAnGGGAGTGTTGGA AGAAACAGTAAAAnGGAATAAG[t/c]GTAGGTGACCGTTG GAGATTTTnGTTTATAAAATGCTGATTTACGATTAAGCTT TAGCCA |
| 58 | NQ0257822 | 4 | 71.66 | A | G | TGGTATACAAATACAGCTCGATATTGGTTACTAATTGCT TGATATTGGTATGGTAATACC[a/g]TAATAGCCCTAACTA GCTCTAGGTCTAAAATTTATCTTTTCATGGAAAATGACA TAGTTT |
| 59 | NQ0345700 | 4 | 76.67 | G | T | AGATTGTGTGTTTCCTAGGATTCCTCAGTTAGCAGTTAT TGGTTTTTCGGGTAGTCTTGC[t/g]AATCTTTACACGTTTG AGATAAGGTCAATGTGGGTGGCTCATTTTCTTGATGGAG GGTTT |
| 60 | NQ0258259 | 4 | 81.48 | G | A | GCCCTGCTCCAGAGCTTATTCTCACGACTGGACGGAGTG CCCTTTCGTGCATCCAGGCGA[A/G]AACGCGCGTCGAAG AGACTTGAAAAnGTnCGTCTACAGCTGCGTTCCGTGTCC TGAGTTC |
| 61 | NQ0344778 | 4 | 83.34 | G | A | TATTAAAGTTTnGTCCAAAAGAAGGCGATAGTGGATCAA CTGAATATCCAACAAGTCCAT[a/g]GTTATTGTTGTTATTA CGATAATTGGATGGAGAGCTTCCACCTGGACTGCCAATT AAAGA |
| 62 | NQ0344946 | 4 | 88.52 | C | C | TGCCTTCCAGCATAAACACCCCTGCACAAAATGCTACAT TTGTTAGGACGTGTCTTGCTA[t/c]TGAGCAAAAATACCC AAATTGGTTGACTCAGTTGCCTCCAAATGATAATAATAA TAAAAC |
| 63 | NQ0257917 | 4 | 92.84 | C | T | AACTGTAGTACAGAAATAAACTAGTCTGAACCCATGCTT CGCACATGGAATCGCACAACA[t/c]GATTAAATAAAATTT GCATAGTACATTTCAGGTTTGCGATGTTTGACAAATACA TCAGAT |

TABLE 2-continued

List of markers for MAS and FxF workflow.

| SEQ ID NO | Marker | LG | Position | Allele of SYG-75-1706 | Allele of SERRANA | DNA Sequence |
|---|---|---|---|---|---|---|
| 64 | NQ0257378 | 6 | 4.61 | G | A | CTATAGTGCAGAGCTTGAACTTGAACCAAAGCAGTATC ATGTAATTGCATTTGAA[a/g]nTCCAGCAGATTCTAAAAnT TTCTGTTATATTGTGCAAGCACATATGGAGATGTTAGGA A |
| 65 | NQ0344375 | 6 | 8.04 | T | C | TCAGGTTGGAGCGGACCCGGAAAGTGCAGCCGCCTACA ATGGAGGTTTGGTTAGGAAGTT[t/c]AATGGTGGAGGAGG GACGCCGTTGATGCCGAAGAGGAAGTTTGAGACGTACA TTTTTGCG |
| 66 | NQ0344545 | 6 | 13.68 | C | C | CAATGAGACATAGCCAATTGGCATTTCGCAGCACTGAC CTAAAATGGATTCATAATCAAA[t/c]CCTTCTAAAGGCAA ACCATTCAAACTTCTATTAGTGATTCTCTTTACGGCCTCA CGTCGA |
| 67 | NQ0345400 | 6 | 17.69 | C | T | ACAATTGCTATCTTCGTTTTTACATnACCGTTTGGTGGTC GATAACATAGATGAATGAAA[t/c]GAGGAGGATTTGATG AAGCAGCAGCAACACCTAAATATGAACCCATCTTCAAT TCCGTGC |
| 68 | NACEP009089369 | 6 | 22.28 | — | — | TGTGGATTAGCTACTAAAAATTATACATGATTTCAGGAA ATGAAGCACATTATTCAATCATAAAGCAAGCTCAGCTG GTTCACCTGGAT[TAGGCCTGTCAAAATTCACTAAACCC ATTTAACCCTACCCTCTTAACCTTATTTTAGACAGGCCG GGCCTTCTCTGAATTCTTTCCTTCGCAACCCGTTTAACCT CTTACTCTTCATACGACCCGTTTAACGTTGTTGC/GACTT GTGTGAAGCACACATTCTGCTGCTGAACCATCCTAAAGC GGAAGGGCGATACATATGCTCTTCTCATGACGTGACAAT TTACGATATGGCTAAAATGATTAGGCAGAACTACCCTCA ATATTACATTCCTCAAC]GACTC |
| 69 | NQ0258009 | 6 | 22.44 | T | C | AGATATAACTACTTTTGGATTATGGGCTTATGATGCTGC TTTTGCCTTAGCAATGGCTAC[T/C]GAGTCAGCTCAGCCA GCTTATAACTATAGTAATGAnGTTGCTAACGGTAATTTA ATGAAG |
| 70 | NQ0344415 | 6 | 22.44 | C | T | AGAAATTACAGTTGATAAAGTAGCCGATGAAGGCAATC TTACACTAGCACAAAGTTTTAG[T/C]GATAACCACAGTG ATAGGGATTCAAGAAAAnCACTGGCTCACTTAACAATG AGCAAATCT |
| 71 | NACEP009090969 | 6 | 22.65 | — | — | GCATTCCATAACCACCATTCAACATGCACTCCACTGGCA TGCAATATGTTATTAnATTTTATGATCAAG[C/T]ACTTTC ATCAGCTGTTACAAGTTGTGACTGTTCGCTGCTAATAAC TTAATAATTCTGTCACTACAACAAAT |
| 72 | NQ0344386 | 6 | 26.52 | — | — | TGGTGTTTCTGGAGCTGAAGCATTTGGAGAAGTATTCAC ATTGAAGGAAnTAGGCATTTG[A/C]ACAGTGCCATAGCA ATTTGGCTCAGAACCAGnCGCACAGATCAAAGGATTTCC TACAATG |
| 73 | NQ0345529 | 6 | 31.49 | — | — | TGACTCTATACTAGATGATGAGTTCTCCTTCTCCAACCT CAACTTATCACATCTGCTATT[t/c]TGACTAACATTCATTG CATCACTTCTGCTTCTTTGAACTCTTTGTTGCAATCCAAC ATTC |
| 74 | NQ0345734 | 6 | 33.62 | — | — | ATGGCTTGAAnGGTCGCTCATCAnCCCCCAGCGGTCCGA CCACTCTATATCCAATCTCCT[c/g]CGCCTCGATTATCTTC TCCTCTTTACTCTTCCCACTCACTTTAAACTTCCTCACGG ATCC |

TABLE 3

List of markers for Taqman® assays.

| Marker | LG | Position | Trait | Probe VIC Sequence | Probe FAM Sequence | Primer F Sequence | Primer R Sequence |
|---|---|---|---|---|---|---|---|
| NQ0257512 | 2 | 40.8 | FBR | AGCTCTACTCTTCCAGCAAA (SEQ ID NO: 75) | CTCTACTCTTGCAGCAAA (SEQ ID NO: 116) | TTTGTAACCAAACTCTGACCTTAGATGTT (SEQ ID NO: 157) | GGTTGGAGATCCAAATTGCTATC (SEQ ID NO: 198) |
| NQ0345493 | 2 | 41 | FBR | ATGATCCAATGCTTTTCCAT (SEQ ID NO: 76) | TGATCCAATGCTCTTCCAT (SEQ ID NO: 117) | GACGAAGGTGATGATGCTTTGC (SEQ ID NO: 158) | GCTAGGCTGGTAGGTTCTTTTAGT (SEQ ID NO: 199) |
| NQ0345038 | 2 | 41.3 | FBR | TCACTTCTGATAAAGCTT (SEQ ID NO: 77) | ACTTCTGATGAAGCTT (SEQ ID NO: 118) | CGGAAGGTCGCGATCCTC (SEQ ID NO: 159) | GAGCTAGCTTGGTAACAAGAGGATT (SEQ ID NO: 200) |
| NQ0345495 | 2 | 42.4 | FBR | CCTTGGAGAGTGTTGTC (SEQ ID NO: 78) | TTGGAGAGCGTTGTC (SEQ ID NO: 119) | GGACGATGCGATCAAGACTACAAAT (SEQ ID NO: 160) | GGTAATGGTATTCTCCAACCTTGGT (SEQ ID NO: 201) |
| NQ0257948 | 2 | 45.6 | FBR | ATCATTGGGAAATAATCAT (SEQ ID NO: 79) | CATTGGGAAGTAATCAT (SEQ ID NO: 120) | GTCCTCTAGCTCTTTTCGGTGTAG (SEQ ID NO: 161) | CACTATAGTGCAGTCAAAGTCTGAGT (SEQ ID NO: 202) |
| NQ0258383 | 2 | 47.4 | FBR | CTGGTCATTTGCTTTAGCT (SEQ ID NO: 80) | TGGTCATTTGCGTTAGCT (SEQ ID NO: 121) | GAATCCCATGATGTCAAATCCGTTT (SEQ ID NO: 162) | GCACTTGGACAGCAACATTTTGA (SEQ ID NO: 203) |
| NQ0257610 | 2 | 47.5 | FBR | ATACGAAATGAAATCATC (SEQ ID NO: 81) | ATACGAAATGTAATCATC (SEQ ID NO: 122) | TGTGCAATTTGTATCCCTGGCATA (SEQ ID NO: 163) | TTAGATTTTCTACCTATGTCCTACCAGGTT (SEQ ID NO: 204) |
| NQ0258102 | 2 | 48.5 | FBR | TTGGTCACCTAGAATGGTA (SEQ ID NO: 82) | TGGTCACCTAGGATGGTA (SEQ ID NO: 123) | CTTTTTCCTCAAGCTGGTTGTCAAT (SEQ ID NO: 164) | ACCTTCTCTCAATTGTGCA (SEQ ID NO: 205) |
| NQ0257924 | 2 | 48.5 | FBR | CTAGCTTTGAGAATCGT (SEQ ID NO: 83) | CTAGCTTTGACAATCGT (SEQ ID NO: 124) | TCCATTTCTTCAGCCCTACTTTGTC (SEQ ID NO: 165) | AAATCATAAGAATTAAGAATTCAAAATCGAATTCAAAAG (SEQ ID NO: 206) |
| NQ0258031 | 2 | 49.8 | FBR | ATGGACTCCATATTTG (SEQ ID NO: 84) | ATGGACTCCGTATTTG (SEQ ID NO: 125) | GAGCCTGCGGCATCATG (SEQ ID NO: 166) | TTTACCAAAGTAATTCTAAATAAGGATTGTT (SEQ ID NO: 207) |
| NQ0257938 | 2 | 50.1 | FBR | TCCAGCACATGCATG (SEQ ID NO: 85) | CAGCGCATGCATG (SEQID NO: 126) | AGAAATGTCTGAATTCAGAGCTCTGG (SEQ ID NO: 167) | GAGTCCCGATTGTTGGCAAAC (SEQ ID NO: 208) |
| NQ0258282 | 2 | 50.1 | FBR | CCACCTACAATAACAACAC (SEQ ID NO: 86) | CACCTACAATAGCAACAC (SEQ ID NO: 127) | ATTGATGTATGTTGTATGTAAACAATAACAGTAAGT (SEQ ID NO: 168) | CAAAGCAACTCCCAGTTCTTCAAC (SEQ ID NO: 209) |
| NQ0258343 | 2 | 50.5 | FBR | ACTTTCTGTTGTTATCTTC (SEQ ID NO: 87) | TTCTGTCGTTATCTTC (SEQ ID NO: 128) | ACATTTCCACACGTTGCATTTTGT (SEQ ID NO: 169) | TTTTACCAAAAGCACTTTTATATTATTGTT (SEQ ID NO: 210) |
| NQ0258609 | 2 | 51.5 | FBR | ACAATTCTTCATACTAATCC (SEQ ID NO: 88) | AATTCTTCATGCTAATCC (SEQ ID NO: 129) | GAACAGATGGGATGATGCAGAGA (SEQ ID NO: 170) | CTCTATACAACTCCATCCAGGCAAT (SEQ ID NO: 211) |
| NQ0257684 | 2 | 52 | FBR | CTTCTCAGTCGAAACAG (SEQ ID NO: 89) | TTCTCAGTGGAAACAG (SEQ ID NO: 130) | GGGTCGCTGGCAATTTTGAA (SEQ ID NO: 171) | GCTTTTAGGCACTTGACTTCTCTCA (SEQ ID NO: 212) |

TABLE 3-continued

List of markers for Taqman® assays.

| Marker | LG | Position | Trait | Probe VIC Sequence | Probe FAM Sequence | Primer F Sequence | Primer R Sequence |
|---|---|---|---|---|---|---|---|
| NQ0258062 | 2 | 52.1 | FBR | CCCTATAGTTCCGATTACT (SEQ ID NO: 90) | CCTATAGTTCGGATTACT (SEQ ID NO: 131) | CTGCATCATCACCCCCTCTT (SEQ ID NO: 172) | CGGAAATTGTACGGCGGGAATAT (SEQ ID NO: 213) |
| NQ0258384 | 2 | 52.1 | FBR | CTTCTCAGTCGAAACAG (SEQ ID NO: 91) | TTCTCAGTGGAAACAG (SEQ ID NO: 132) | CTTATGACCAGGCAGCTTTTGC (SEQ ID NO: 173) | GCTTTTAGGCACTTGACTTCTCA (SEQ ID NO: 214) |
| NQ0257410 | 2 | 53.3 | FBR | CCGAACCCCACAAAC (SEQ ID NO: 92) | CGAACCGCACAAAC (SEQ ID NO: 133) | CCCCTACCTCTTATCAGAACATCGA (SEQ ID NO: 174) | GGCAATTTTTGATGAGGCATGGAA (SEQ ID NO: 215) |
| NQ0257277 | 2 | 53.5 | FBR | ACAGCCCTAAATTCTA (SEQ ID NO: 93) | AGCCCTGAATTCTA (SEQ ID NO: 134) | TCACAGACATTAGTATGAAAGCAAGCA (SEQ ID NO: 175) | GCAAGATGCAAAACTCAAATTTCTAGCA (SEQ ID NO: 216) |
| NQ0257326 | 2 | 55.1 | PR | ACCGCTAATACTAAATAT (SEQ ID NO: 94) | CGCTAATGCTAAATAT (SEQ ID NO: 135) | CCCCTTCAAGAGCAAGATTCTCA (SEQ ID NO: 176) | GCCCTGATCTTGAGTGTAGTTTGG (SEQ ID NO: 217) |
| NQ0257570 | 2 | 55.6 | PR | CATCGTCATCATCATCT (SEQ ID NO: 95) | CATCGTCATCGTCATCT (SEQ ID NO: 136) | GAGGATTCATTCATTCATGTTAAAGTGCAT (SEQ ID NO: 177) | GCAAGGGTAAGAAAATCGAAAACCA (SEQ ID NO: 218) |
| NQ0257962 | 2 | 57.2 | PR | CGGATGCAGTAATTAAGA (SEQ ID NO: 96) | CGGATGCAGTAGTTAAGA (SEQ ID NO: 137) | CATGCCCCTTATCTTGCTATTTATCTCA (SEQ ID NO: 178) | CAGTTAAGAAGGGATTCCTCTGCAT (SEQ ID NO: 219) |
| NQ0258453 | 2 | 62.5 | Color | TGTTAATGGGTTTTGATTTAG (SEQ ID NO: 97) | AATGGGTTTCGATTTAG (SEQ ID NO: 138) | GATATTCTTCTCTGTAAATAGCCTCGAGATT (SEQ ID NO: 179) | TGGGTCCTACTTTGTTTGTTGGAT (SEQ ID NO: 220) |
| NACEP009407370/ NQ0257461 | 2 | 63.1 | Color | AGCATAGAAGGTTATAACTG (SEQ ID NO: 98) | CATAGAAGGCTATAACTG (SEQ ID NO: 139) | CTGCAGGAAGCAATAGAAAAAGCAA (SEQ ID NO: 180) | AACATAATTAATAAATAAGTGTAACTTTGCATGAA (SEQ ID NO: 221) |
| NQ0257641 | 4 | 30.6 | PNBR | ATTTCAGGGCAACTTAGAAT (SEQ ID NO: 99) | TCAGGGCAACCTAGAAT (SEQ ID NO: 140) | GCTTCATTGTCTTGCTGGTTTTCAA (SEQ ID NO: 181) | CCTGCCTTTTCACATTTTTCCCATT (SEQ ID NO: 222) |
| NQ0345175 | 4 | 32.8 | PNBR | TGAAGCAGAGTGATCAGTT (SEQ ID NO: 100) | AAGCAGAGTGGTCAGTT (SEQ ID NO: 141) | GCAGAGTAATCGGCATGTCTTCTT (SEQ ID NO: 182) | GTCGTACTCTCCTGCACCAA (SEQ ID NO: 223) |
| NQ0257536 | 4 | 35.6 | PNBR | TCGTGCAATAAAAGC (SEQ ID NO: 101) | TCGTGCAATGAAAGC (SEQ ID NO: 142) | CCCATTTGTTTCTAACTAAATCTCAAAGGAAAA (SEQ ID NO: 183) | TGATTGACTGATTGTGTAGCTTGAAGA (SEQ ID NO: 224) |
| NQ0258247 | 4 | 38 | PNBR | CACCAAATGAGATATACAC (SEQ ID NO: 102) | CACCAAATGAGGTATACAC (SEQ ID NO: 143) | CGATGCATTTGAGATTGTTGTGGAA (SEQ ID NO: 184) | GTCATCCAAACATTTATCGTTACAAGGAA (SEQ ID NO: 225) |
| NQ0257799 | 4 | 44.8 | PNBR | CTTTGCCTCACTAAAGG (SEQ ID NO: 103) | TTTGCCTCGCTAAAGG (SEQ ID NO: 144) | TAAAAGAATACTATTATCCTTAAATCAACATCT (SEQ ID NO: 185) | AGTTCAAGAGAAACGAAACTCGGTAA (SEQ ID NO: 226) |
| NQ0345680 | 4 | 49.4 | Color | CAGGCACAGGTCCAG (SEQ ID NO: 104) | AGGCACCGGTCCAG (SEQ ID NO: 145) | CGCTGGAGCTCCTGGTG (SEQ ID NO: 186) | CACCCGAAGTTCCAGAAGGTT (SEQ ID NO: 227) |

TABLE 3-continued

List of markers for Taqman® assays.

| Marker | LG | Position | Trait | Probe VIC Sequence | Probe FAM Sequence | Primer F Sequence | Primer R Sequence |
|---|---|---|---|---|---|---|---|
| NQ0345468 | 4 | 50.9 | Color | TCAGATCTCCATGATGATG (SEQ ID NO: 105) | AGATCTCCACGATGATG (SEQ ID NO: 146) | ATTGCCGTGAAGAAAGTACTGGAA (SEQ ID NO: 187) | GCCTTAACTTGCTGATTATCTCAACCT (SEQ ID NO: 228) |
| NQ0345333 | 4 | 52 | Color | AAGATGATGCATGCTTC (SEQ ID NO: 106) | AAAGATGATGCTTGCTTC (SEQ ID NO: 147) | AGCCACAACAATAGACCAAAATG (SEQ ID NO: 188) | CCTTGTGCTGCCTGGTTGA (SEQ ID NO: 229) |
| NQ0344746 | 4 | 54.3 | Color | TCGCTGCCAATACCTGA (SEQ ID NO: 107) | CGCTGCCAGTACCTGA (SEQ ID NO: 148) | GGAGTAGAAACAAGTGAAGCTGCTA (SEQ ID NO: 189) | TCCGAAGGTAATAGTTCTGACGAAGA (SEQ ID NO: 230) |
| NQ0345071 | 5 | 7.1 | PNBR | CAAGAAATGAGCAGTAATAT (SEQ ID NO: 108) | AAGAAATGAGCGGTAATAT (SEQ ID NO: 149) | AGGAAGTTGAAAAGGCCATTAACGA (SEQ ID NO: 190) | CTTTTTGAACCATTTCTTTTCTCCTGTCT (SEQ ID NO: 231) |
| NQ0345144 | 5 | 11 | PNBR | CCGCCATAGCTCTAA (SEQ ID NO: 109) | CGCCATGGCTCTAA (SEQ ID NO: 150) | CGAGTGCTCCCTCATGTATTTGG (SEQ ID NO: 191) | CCTACCAAAACGCCAAAGAATTACA (SEQ ID NO: 232) |
| NQ0258331 | 5 | 19 | PNBR | TGAAAGTGTGTCATCAATTA (SEQ ID NO: 110) | AAAGTGTGTCGTCAATTA (SEQ ID NO: 151) | CCTTGAGTACCTAGGTGACTATCGT (SEQ ID NO: 192) | TCTTGAATCTCTCTGTTAATAGTTCAAATCGTG (SEQ ID NO: 233) |
| NACEP009089369 | 6 | 22.3 | R locus; color | CCTGGATTAGGCCTG (SEQ ID NO: 111) | CCTGGATGACTTGTGT (SEQ ID NO: 152) | AAGAGTAAGAGGTTAAACGGGTTGC (SEQ ID NO: 193), ATCATTTTAGCCATATCGTAAATTGTCA (SEQ ID NO: 239US) | AATTATACATGATTTCAGGAAATGAAGCAC (SEQ ID NO: 234) |
| NQ0258009 | 6 | 22.4 | R locus | CAATGGCTACTGAGTCAG (SEQ ID NO: 112) | AATGGCTACCGAGTCAG (SEQ ID NO: 153) | GCTTATGATGCTGCTTTTGCCTTAG (SEQ ID NO: 194) | TCATTACTATAGTTATAAGCTGGCTGAG (SEQ ID NO: 235) |
| NQ0344415 | 6 | 22.4 | R locus | ACTGTGGTTATCACTAAAA (SEQ ID NO: 113) | CTGTGGTTATCGCTAAAA (SEQ ID NO: 154) | CGATGAAGGCAATCTTACACTAGCA (SEQ ID NO: 195) | GCTCATTGTTAAGTAGCCAGTG (SEQ ID NO: 236) |
| NACEP009090969 | 6 | 22.6 | R locus; color | CTGATGAAAGTGCTTGATC (SEQ ID NO: 114) | CTGATGAAAGTACTTGATC (SEQ ID NO: 155) | ACTCCACTGGCATGCAATATGTTAT (SEQ ID NO: 196) | AGCGAACAGTCACAACTTGTAACA (SEQ ID NO: 237) |
| NACEP009112570 | — | — | ANS color | GAGTTACCTCTTAGCT (SEQ ID NO: 115) | TTGGAGCATACCCTA (SEQ ID NO: 156) | AGTAGAAATAAGTGAAGAATATTGATGTG (SEQ ID NO: 197), TACAATATGATACAGAAAATCAGAG (SEQ ID NO: 240US) | TGGTTTGAGCTTGTTGGTTTGGAG (SEQ ID NO: 238) |

Example 5

Onion *Fusarium* Basal Rot (FBR) LG2 QTL Fine Mapping

F3 bulbs were obtained from the original SYG-75-1706/Serrana-FBR mapping population described in Example 1. Segregating F2:3 families were chosen based on desired genotype data in the QTL region for FBR on LG2, on order to narrow the major effect FBR QTL region from >12 cM to less than 5 cM. The F2 genotype in the LG2 QTL region of the selected F3 families is depicted in Table 4. As seen in Table 4, the F2:3 segpop families were chosen to have a recombination in the FBR QTL LG2 region, and heterozygous (shaded) for a "stair-stepped" section of the QTL region in the F2 generation. The heterozygous region in the F2 individuals was chosen such that F3 individuals (bulbs) homozygous for the favorable allele and homozygous for the unfavorable allele could be selected for further experimentation in the F3 generation to enable fine mapping.

TABLE 4

Genotype depiction of the six F2 plants selected for FBR LG2 QTL fine mapping. F3 bulbs from each of these families were genotyped with markers in the LG2 QTL region as subsequently described.

| Pedigree Source | NQ-0345038 LG2 Pos 41.3 FBRR | NQ-0257827 42.4 FBRR | NQ-0257948 45.6 FBRR | NQ-0258383 47.4 FBRR | NQ-0258005 49.2 FBRR | NQ-0257848 49.8 FBRR | NQ-0258031 49.8 FBRR | NQ-0258609 51.5 FBRR | NQ-0257954 51.6 FBRR | NQ-0257684 52 FBRR | NQ-0258384 52.1 FBRR | NQ-0257410 53.3 FBRR | NQ-0257277 53.5 FBRR | NQ-0257326 55.1 PRR | NQ-0257570 55.6 PRR | NQ-0258453 62.5 color | NQ-0257461 63.1 color |
|---|---|---|---|---|---|---|---|---|---|---|---|---|---|---|---|---|---|
| SYG-75-1706 HCH0351-S1 | GG | CC | TT | CC | GG | CC | TT | CC | AA | CC | CC | GT | TT | CC | CC | GG | GG |
| RV_SYG-75-1706/SERRANA-FBR:01.0032 HCS0063 | AG | CT | CT | AC | CG | CT | CT | CT | AG | CC | CG | GG | TT | CC | CC | GG | GG |
| RV_SYG-75-1706/SERRANA-FBR:01.0167 HCS0333 | AA | TT | CC | AC | AC | CT | CT | CT | AG | CC | CC | GG | TT | CC | CC | GG | AG |
| RV_SYG-75-1706/SERRANA-FBR:01.0001 HCS0367 | AG | CT | CT | — | CG | CT | CT | CT | AG | CG | CG | GG | TT | | | GG | GG |
| RV_SYG-75-1706/SERRANA-FBR:01.0147 HCS0293 | AG | CT | CT | AC | CG | CT | CT | CT | AG | CG | CG | GG | CT | CC | CC | GG | GG |
| RV_SYG-75-1706/SERRANA-FBR:01.0113 HCS0591 | AG | CT | CT | AC | CG | CT | CT | CC | AA | CC | CC | GG | TT | CC | CC | GG | GG |
| RV_SYG-75-1706/SERRANA-FBR:01.0167 HCS0659 | AG | CT | TT | CC | GG | CC | TT | CC | AA | CC | CC | GG | TT | CC | CC | GG | GG |

Based on the genotypes in the LG2 QTL of the F3 bulbs from each of the six families in Table 4, bulb selections for the homozygous favorable and unfavorable alleles were made. For example, for the segregating population RV_SYG-75-1706/SERRANA-FBR: 01.0113. cross, ten F3 bulbs that were fixed homozygous for the Serrana allele at and to the left of position 49.8 on LG2 and ten F3 bulbs that were fixed homozygous for the SYG-75-1706 allele across the whole FBR QTL region were selected (see Table 5). The selected bulbs (one separate cage for each allele "group") for each of the 6 segregating populations were transplanted into 16 head cages in a cage field north of Woodland in December. The F3 bulb selections for favorable and unfavorable alleles at each "stair step" are separately massed to produce seed fixed for only the recombinant QTL region of interest, while keeping the rest of the genome heterogeneous (reducing the chance of inbreeding depression and background QTL effects).

The massed seed is harvested and tested for FBR. For each of the 6 families, a statistical difference between the two entries that represent the two massed allele "groups" of that family allows determination of whether the FBR resistance is located with the respective genetic interval for which that F3 family is segregating.

TABLE 5

Example of F3 bulbs selected for massing (family RV_SYG-75-1706/SERRANA-FBR:01.0113.).

| | | NQ0345038 | NQ0257948 | NQ0258383 | NQ0258031 | NQ0258609 | NQ0257684 | NQ0258384 | NQ0257410 | NQ0257277 | NQ0257570 | NACEP009407370 |
|---|---|---|---|---|---|---|---|---|---|---|---|---|
| | Chr | 2 | 2 | 2 | 2 | 2 | 2 | 2 | 2 | 2 | 2 | 2 |
| | Pos | 41 | 46 | 47 | 50 | 51 | 52 | 52 | 53 | 53 | 56 | 63 |
| | Trait QTL: | FBRR | FBRR | FBRR | FBRR | FBRR | FBRR | FBRR | FBRR | FBRR | PRR | color |
| | F3 plant ID | | | | | | | | | | | |
| SYG-75-1706 (HCH0351-S1) | | GG | 7 | CC | TT | CC | CC | CC | GG | TT | CC | GG |
| RV_SYG-75-1706/SERRANA-FBR01.0113. | 353 | AA | CC | AA | CC | CC | CC | CC | GG | TT | CC | GG |
| RV_SYG-75-1706/SERRANA-FBR01.0113. | 358 | AA | CC | AA | CC | CC | CC | CC | GG | TT | CC | GG |
| RV_SYG-75-1706/SERRANA-FBR01.0113. | 359 | AA | CC | AA | CC | CC | CC | CC | GG | TT | CC | GG |
| RV_SYG-75-1706/SERRANA-FBR01.0113. | 375 | AA | CC | AA | CC | CC | CC | CC | GG | TT | CC | GG |
| RV_SYG-75-1706/SERRANA-FBR01.0113. | 395 | AA | CC | AA | CC | CC | CC | CC | GG | TT | CC | GG |
| RV_SYG-75-1706/SERRANA-FBR01.0113. | 397 | AA | CC | AA | CC | CC | CC | CC | GG | TT | CC | GG |
| RV_SYG-75-1706/SERRANA-FBR01.0113. | 402 | AA | CC | AA | CC | CC | CC | CC | GG | TT | CC | GG |
| RV_SYG-75-1706/SERRANA-FBR01.0113. | 408 | AA | CC | AA | CC | CC | CC | CC | GG | TT | CC | GG |
| RV_SYG-75-1706/SERRANA-FBR01.0113. | 413 | AA | CC | AA | CC | CC | CC | CC | GG | TT | CC | GG |
| RV_SYG-75-1706/SERRANA-FBR01.0113. | 415 | AA | CC | AA | CC | CC | CC | CC | GG | TT | CC | GG |
| RV_SYG-75-1706/SERRANA-FBR01.0113. | 351 | GG | TT | CC | TT | CC | CC | CC | GG | TT | CC | GG |
| RV_SYG-75-1706/SERRANA-FBR01.0113. | 389 | GG | TT | CC | TT | CC | CC | CC | GG | TT | CC | GG |

TABLE 5-continued

Example of F3 bulbs selected for massing (family RV_SYG-75-1706/SERRANA-FBR:01.0113.).

| | NQ0345038 | NQ0257948 | NQ0258383 | NQ0258031 | NQ0258609 | NQ0257684 | NQ0258384 | NQ0257410 | NQ0257277 | NQ0257570 | NACEP0094O7370 |
|---|---|---|---|---|---|---|---|---|---|---|---|
| RV_SYG-75-1706/SERRANA-FBR:01.0113. 390 | GG | TT | CC | TT | CC | CC | CC | GG | TT | CC | GG |
| RV_SYG-75-1706/SERRANA-FBR:01.0113. 405 | GG | TT | CC | TT | CC | CC | CC | GG | TT | CC | GG |
| RV_SYG-75-1706/SERRANA-FBR:01.0113. 425 | GG | TT | CC | TT | CC | CC | CC | GG | TT | CC | GG |
| RV_SYG-75-1706/SERRANA-FBR:01.0113. 440 | GG | TT | CC | TT | CC | CC | CC | GG | TT | CC | GG |
| RV_SYG-75-1706/SERRANA-FBR:01.0113. 445 | GG | TT | CC | TT | CC | CC | CC | GG | TT | CC | GG |
| RV_SYG-75-1706/SERRANA-FBR:01.0113. 448 | GG | TT | CC | TT | CC | CC | CC | GG | TT | CC | GG |
| RV_SYG-75-1706/SERRANA-FBR:01.0113. 451 | GG | TT | CC | TT | CC | CC | CC | GG | TT | CC | GG |
| RV_SYG-75-1706/SERRANA-FBR:01.0113. 496 | GG | TT | CC | TT | CC | CC | CC | GG | TT | CC | GG |

Subsequently, 29 additional F2:3 families have been chosen from the SYG-75-1706/Serrana population for further fine mapping of the FBR QTL on LG2, as well as validation of the QTLs for FBR on LG3 and LG4.

The F3 families for the FBR QTL fine mapping project represent more coverage of the FBR QTL region on LG2, to produce individuals that allow further narrowing of the FBR QTL region on LG2.

The F3 families for the FBR QTL validation are represented by families that are fixed for the Serrana favorable alleles in the major FBR QTL region on LG2, but are heterozygous for the minor QTL regions on LG3 and LG4. Similar selection for individuals homozygous for various combinations of both alleles for the minor QTL (given that LG2 QTL is fixed), as described above, produce massed seed entries that can be trialed to determine if the minor QTL provide significant additional resistance to FBR.

Example 6

Onion FBR-PR Resistance Trait Coupling Project

Similar to the fine mapping project, coupling of FBR and PR resistance could be accomplished through a 2-tier approach using available F3 bulbs, as well as planting F3 seed sources of genetic material from the SYG-75-1706/Serrana population. Bulbs are sampled to identify individuals that combine the favorable alleles for FBR QTL from Serrana on LG2 with the favorable alleles for PR from SYG-75-1706 on LG2, in a North American yellow bulb (or Universal Yellow).

For the steckling/seed source approach, seven F3 families were selected based on F2 plant marker data to have a favorable combination of alleles in the LG2 trait region and LG6 color QTL region, as well as a favorable phenotypic disease score. The F3 seed was planted and resulting F3 plants genotyped with Taqman markers that encompassed the main QTL for FBR on LG2, minor QTL for FBR on LG3 & LG4, PR QTL region on LG2, plus color QTL regions on LG2 and LG6. Recombinant individuals from each F3 family were identified to contain as much of the full complement of traits as possible in either a fixed or heterozygous state, and "like" individuals were placed together in a head cage for future massing.

Table 6 presents representative genotypes of the F2 families that were initially selected for follow-up, and the selections of the resulting F3 plants that were selected to have desirable recombination for combining the traits. Markers to indicate the favorable alleles for FBR resistance (FBRR) on LG2 were used as the main criteria, followed by favorable alleles for PR resistance (PRR) on LG2 and lastly the favorable color alleles, ideally the Universal Yellow, which combines the Serrana color allele on LG2 and the SYG-75-1706 color allele on LG6; however, obtaining a North American yellow was also an objective, which requires a SYG-75-1706 color allele for both LG2 and LG6 color regions/QTL. The massed seed from these cages is harvested and trialed to verify the traits have been coupled. In the cases of Universal Yellow FBR+PR combinations, this involves a double recombination on LG2 and therefore these require one additional generation of MAS to fix all traits.

TABLE 6

Genotypic and phenotypic information for a majority of the F2 families selected for trait coupling in subsequent F3 (and beyond) generations.

| | NQ 0345038 | NQ 0257948 | NQ 0253383 | NQ 0258031 | NQ 0258609 | NQ 0257684 | NQ 0258384 | NQ 0257410 | NQ 0257277 | NQ 0257326 | NQ 0257570 | NQ 0258453 | NQ 0258009 | NQ 0344415 | PR Score | FBR score |
|---|---|---|---|---|---|---|---|---|---|---|---|---|---|---|---|---|
| LG | 2 | 2 | 2 | 2 | 2 | 2 | 2 | 2 | 2 | 2 | 2 | 2 | 6 | 6 | | |
| Pos | 41.3 | 45.6 | 47.4 | 49.8 | 51.5 | 52 | 52.1 | 53.3 | 53.5 | 55.1 | 55.6 | 62.5 | 22.4 | 22.4 | | Donna, Deforest, WI & mortality |
| Desired Haplotype - Universal | FBRR | FBRR | FBRR | FBRR | FBRR | FBRR | FBRR | FBRR | FBR-PR | PRR | PRR | COLOR | color | color | | |
| Desired Haplotype - NA Yellow: | FBRR | FBRR | FBRR | FBRR | FBRR | FBRR | FBRR | FBRR | FBR-PR | PRR | PRR | COLOR | color | color | | |
| Parent: SYG-75-1706 (HCH0351-) | GG | TT | CC | TT | TT | CC | CC | GG | TT | CC | CC | GG | TT | CC | PRR | 94.8 |
| F2 progenitor plant, HCS0103 | AG | CT | AA | CC | CC | GG | GG | CC | CC | CC | CC | AG | TT | CC | seg | 75.8 |
| Cage F3 1: selections, FBR-PR- NA Yellow | AA | CC | AA | CC | TT | GG | GG | CC | CC | CC | CC | GG | TT | CC | | |
| Cage F3 2: selections, FBR-PR-seg Univ Yellow | AA | CC | AA | CT | CT | CG | CG | CC | CC | CC | CC | AG | TT | CC | | |
| F2 progenitor plant, HCS0149 | AG | CT | AC | CT | CT | CG | CG | CC | CT | — | CT | AA | — | CC | seg | 69.2 |

TABLE 6-continued

Genotypic and phenotypic information for a majority of the F2 families selected for trait coupling in subsequent F3 (and beyond) generations.

| | NQ 0345038 | NQ 0257948 | NQ 0258383 | NQ 0258031 | NQ 0258609 | NQ 0257684 | NQ 0258384 | NQ 0257410 | NQ 0257277 | NQ 0257326 | NQ 0257570 | NQ 0258453 | NQ 0258009 | NQ 0344415 | PR Score | FBR score |
|---|---|---|---|---|---|---|---|---|---|---|---|---|---|---|---|---|
| Cage 3: F3 selections, FBR-seg PRR-Univ Yellow | AA | CC | AA | CC | TT | GG | GG | CC | CC | CT | AA | TT | CC | CC | | |
| Cage 4: F3 selections, seg FBR PRR-Univ Yellow | AG | CT | AC | CT | CT | CG | CG | CG | CT | CC | AA | TT | CC | CC | | |
| F2 progenitor plant, HCS0537 | AA | CC | AA | CC | TT | CG | CG | GG | TT | CC | GG | CT | CT | CT | PRR | 73.9 |
| Cage 5: F3 selections, FBR-PRR-NA Yellow | AA | CC | AA | CC | TT | GG | GG | GG | TT | CC | GG | TT | TT | CC | | |
| F2 progenitor plant, HCS0189 | AG | CT | AC | CT | CT | CG | CG | CG | CT | CT | AA | CC | CC | CT | seg | 70.6 |
| Cage 6: F3 selections, seg FBR PRR-seg Univ Yellow | AG | CT | AC | CT | CT | CG | CG | CG | CT | CC | AA | CC | CC | CT | | |

TABLE 6-continued

Genotypic and phenotypic information for a majority of the F2 families selected for trait coupling in subsequent F3 (and beyond) generations.

| | NQ 0345038 | NQ 0257948 | NQ 0258383 | NQ 0258031 | NQ 0258609 | NQ 0257684 | NQ 0258384 | NQ 0257410 | NQ 0257277 | NQ 0257326 | NQ 0257570 | NQ 0258453 | NQ 0258009 | NQ 0344415 | PR Score | FBR score |
|---|---|---|---|---|---|---|---|---|---|---|---|---|---|---|---|---|
| Cage 6: F3 selections, FBR-seg PRR-Univ Yellow | AA | CC | AA | CC | TT | GG | GG | CC | CC | ** | CT | AA | CC | CC | seg | 87.4 |
| F2 progenitor plant, HCS0275 | AG | CT | AC | CT | CT | CG | CG | CG | CT | CT | CT | AA | TT | CC | | |
| Cage 7: F3 selections, FBR-seg PRR-Univ Yellow | AA | CC | AA | CC | TT | GG | GG | CC | CC | CT | CT | AA | TT | CC | | |
| Cage 8: F3 selections, seg FBR PRR-Univ Yellow | AG | CT | AC | CT | CT | CG | CG | CG | CT | CT | CC | AA | TT | CC | | |
| F2 progenitor plant, HCS0723 | AG | CT | AC | CT | TT | GG | GG | CC | CC | CT | CT | AG | CT | CT | seg | 73.9 |
| Cage 9: F3 selections, FBR trunc-PRR-NA yellow | GG | TT | CC | CC | TT | GG | GG | CC | CC | TT | CC | GG | TT | CC | | |

TABLE 6-continued

Genotypic and phenotypic information for a majority of the F2 families selected for trait coupling in subsequent F3 (and beyond) generations.

| | NQ 0345038 | NQ 0257948 | NQ 0258383 | NQ 0258031 | NQ 0258609 | NQ 0257684 | NQ 0258384 | NQ 0257410 | NQ 0257277 | NQ 0257326 | NQ 0257570 | NQ 0258453 | NQ 0258009 | NQ 0344415 | PR Score | FBR score |
|---|---|---|---|---|---|---|---|---|---|---|---|---|---|---|---|---|
| Cage 10: F3 selections, FBR-seg PRR-seg color | AA | CC | AA | CC | TT | GG | GG | CC | CC | TT | CT | AG | CT | ** | | |
| Cage 11: F3 selections, FBR trunc-PRR-seg color | GG | TT | CC | CC | TT | GG | GG | CC | CC | TT | CC | AG | ** | CT | | |

Shown are the F2 genotypes for the QTL regions of interest, and below each F2 progenitor is a representative genotype of the (several) F3 progeny that were selected to mass in cages for creation of a trait donor. The desired haplotype was a North American or Universal Yellow with FBR+PR resistance. Several cages provide a North America yellow FBR+PR donor and several cages provide a Universal Yellow FBR+PR donor (requiring 1 round of additional MAS).

Example 7

Leading germplasm event donors possessing necessary gene combinations to attain both Universal Yellow and North American Yellow donors that all have combined FBR and PR resistance, made possible through recombination in the target region of Linkage Group 02 have been made (Table 7). The event donors in this table are a subset of selections as depicted in Table 4 and Table 6 previously described. The derivation from the Table 4 & 6 families can be identified in the current table through the Progenitor Source ID (prefixes "HCS"). Pathology tests indicate that all of the 2 Universal donors and 3 North American Yellow donors possess high levels of FBR resistance, significantly equivalent to the resistant parent Serrana. Similarly, bulb color and/or pink root resistance have been phenotypically confirmed from previous generation data to be fixed favorable for several of these donors, as indicated by "YELLOW" or "RESIST" in the respective table columns. In all cases, the desired recombination events (single or double recombination events as required for the LG02 region in the North American or Universal yellow donors, respectively) have been generated, and FBR resistance has been fixed and phenotypically confirmed. Two of the North American Yellow donor events are fixed for the desired LG02 and LG06 configuration. Genotypic regions segregating in this data set (denoted as "SEG" in table) are being fixed in one more breeding cycle, with molecular markers indicated, to obtain fixed color loci configuration or PR resistance.

TABLE 7

Genotypic and phenotypic information for leading germplasm event donors.

| Identifier | Cage Designation (Progenitor Source ID) | Target: Current Status | Previous Generation Phenotype Bulb Color | Previous Generation Pink Root Resistance Field Test - Donna, Texas | Current Generation FBR Path % Mortality Avg (February 2014) | NQ0345038 | NQ0257948 | NQ0258383 | NQ0258031 | NQ0258609 | NQ0257684 |
|---|---|---|---|---|---|---|---|---|---|---|---|
| | | LG: | | | | 2 | 2 | 2 | 2 | 2 | 2 |
| | | Position: | | | | 41.3 | 45.6 | 47.4 | 49.8 | 51.5 | 52.0 |
| | | QTL/Trait Regions: | | | | FBRR | FBRR | FBRR | FBRR | FBRR | FBRR |
| | | Target Haplotype- Universal Yellow: | | | | Serrana | Serrana | Serrana | Serrana | Serrana | Serrana |
| | | Target Haplotype- North American Yellow: | | | | Serrana | Serrana | Serrana | Serrana | Serrana | Serrana |
| Serrana | REH0001 | Parent 1 (Serrana) | YELLOW | SUSC | 49 | AA | CC | AA | CC | TT | GG |
| SYG-75-1706 | | Parent 2 (SYG-75-1706) | YELLOW | RESIST | 74 | GG | TT | CC | TT | CC | CC |
| Universal Yellow: IR/HR FBR with QTL recombinant A | 660-01-13 (HCS0103) | Universal Yellow: FBRR + PRP + seg LG02 Universal Yellow | YELLOW | SEG | 52 | AA | CC | AA | CC | TT | GG |
| Universal Yellow: IR/HR FBR with QTL recombinant B | 665-01-13 (HCS0275) | Universal Yellow: FBRR + sea PRR + Universal Yellow | YELLOW | SEG | 46 | AA | CC | AA | CC | TT | GG |

TABLE 7-continued

Genotypic and phenotypic information for leading germplasm event donors.

| | | | | | | | | | | | | |
|---|---|---|---|---|---|---|---|---|---|---|---|---|
| NA yellow: IR/HR FBR with QTL recombinant | C | 659-01-13 (HCS0103) | FBRR + PRR + NA yellow | YELLOW | SEG | 47 | ** | CC | AA | CC | TT | GG |
| NA yellow: HR FBR, confirm HR PR In Texas test | D | 668-01-13 (HCS0723) | FBRR + PRR + seg LG06 NA yellow | SEG | SEG | 44 | AA | CC | AA | CC | TT | GG |
| NA yellow: HR FBR, HR = PR | E | 686-01-13 (HCS0333) | FBRR + PRR + NA yellow | YELLOW | RESIST | 50 | AA | CC | AA | CC | TT | CC |
| | | | LSD(0.05) | | | 14.2 | | | | | | |

| Identifier | Cage Designation (Progenitor Source ID) | Target: Current Status | | | | | | | | | | |
|---|---|---|---|---|---|---|---|---|---|---|---|---|
| | | LG: | | | NQ0258384 | NQ0257410 | NQ0257277 | NQ0257326 | NQ0257570 | NQ0258453 | NQ0257461 = NACEP009407370 | NQ0258009 | NQ0344415 |
| | | Position: | | | 2 | 2 | 2 | 1 | 2 | 2 | 2 | 6 | 6 |
| | | QTL/Trait Regions: | | | 52.1 | 53.3 | 53.5 | 55.1 | 55.6 | 62.5 | 63.1 | 22.4 | 22.4 |
| | | Target Haplotype-Universal Yellow: | | | FBRR | FBRR | FBRR-PRR | PRR | PRR | PRR-COLOR | COLOR | COLOR | COLOR |
| | | Target Haplotype- North American Yellow: | | | Serrana | Serrana | | 1706 | 1706 | Serrana | Serrana | 1706 | 1706 |
| | | | | | Serrana | Serrana | | 1706 | 1706 | Serrana | 1706 | 1706 | 1706 |
| Serrana | REH0001 | Parent 1 (Serrana) | | | GG | CC | CC | TT | TT | AA | AA | CC | TT |
| SYG-75-1706 | | Parent 2 (SYG-75-1706) | | | CC | GG | TT | CC | CC | GG | GG | TT | CC |

TABLE 7-continued

Genotypic and phenotypic information for leading germplasm event donors.

| | | | | | | | | | | | |
|---|---|---|---|---|---|---|---|---|---|---|---|
| A | Universal Yellow: IR/HR FBR with QTL recombinant | 660-01-13 (HCS0103) | Universal Yellow: FBRR + PRP + seg LG02 Universal Yellow | GG | CC | CC | CC | SEG | SEG | TT | CC |
| B | Universal Yellow: IR/HR FBR with QTL recombinant | 665-01-13 (HCS0275) | Universal Yellow: FBRR + sea PRR + Universal Yellow | GG | CC | SEG | SEG | AA | AA | TT | CC |
| C | NA yellow: IR/HR FBR with QTL recombinant | 659-01-13 (HCS0103) | NA Yellow: FBRR + PRR + NA yellow | GG | CC | CC | CC | GG | GG | TT | CC |
| D | NA yellow: HR FBR, confirm HR PR In Texas test | 668-01-13 (HCS0723) | NA Yellow: FBRR + PRR + seg LG06 NA yellow | GG | CC | TT | SEG | SEG | SEG | SEG | SEG |
| E | NA yellow: HR FBR, HR = PR | 686-01-13 (HCS0333) | NA Yellow: FBRR + PRR + NA yellow | CC | TT | TT | CC | GG | GG | TT | CC |
| | | | LSD(0.05) | | | | | | | | |

What is claimed is:

1. An onion plant comprising a cis-coupled linkage comprising resistance to *Fusarium* basal rot (FBR) and pink root (PR), wherein said resistance to FBR is conferred by an onion genomic region on LG2 found in *Serrana* onion that comprises an "A" at position 61 of SEQ ID NO:7 and a "G" at position 61 of SEQ ID NO:17; wherein said resistance to PR is conferred by an onion genomic region on LG2 that comprises a "C" at position 61 of SEQ ID NO:24 and a "G" at position 61 of SEQ ID NO:27; and wherein the plant further lacks linkage of the complementary pinks trait to said cis-coupled linkage, and wherein said genomic region on LG2 comprising said resistance to PR is found in onion line SYG-75-1706, a sample of seed of said line having been deposited under NCMA Accession No. 202112015.

2. The onion plant of claim 1, wherein said plant comprises a cis-coupled linkage comprising resistance to *Fusarium* basal rot conferred by an onion genomic region defined by loci NQ0345038 (SEQ ID NO:3) and NQ0257326 (SEQ ID NO:23) on linkage group 2 (LG2), resistance to pink root conferred by an onion genomic region defined by loci NQ0257277 (SEQ ID NO:22) and NQ0258453 (SEQ ID NO:27) on linkage group 2 (LG2), and lack of the complimentary pinks bulb color conferred by an onion genomic region defined by loci NQ0257220 (SEQ ID NO:26) and NQ0257692 (SEQ ID NO:29) on linkage group 2 (LG2).

3. The onion plant of claim 2, wherein said onion plant is of an onion variety selected from the group consisting of North American Yellow and Universal Yellow.

4. A part of the onion plant of claim 1, further defined as pollen, an ovule, a leaf, an embryo, a root, a root tip, an anther, a flower, a bulb, a stem, a shoot, a seed, a protoplast, a cell, and a callus.

5. The onion plant of claim 1, wherein the onion plant is an agronomically elite line.

6. The onion plant of claim 1, wherein the onion plant is a hybrid.

7. The onion plant of claim 1, wherein the onion plant is an inbred.

* * * * *

SEQUENCE LISTING

<160> NUMBER OF SEQ ID NOS: 240

<210> SEQ ID NO 1
<211> LENGTH: 121
<212> TYPE: DNA
<213> ORGANISM: Artificial sequence
<220> FEATURE:
<223> OTHER INFORMATION: Marker sequence
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (93)..(93)
<223> OTHER INFORMATION: n is a, c, g, or t
<220> FEATURE:
<221> NAME/KEY: misc_feature
<222> LOCATION: (119)..(119)
<223> OTHER INFORMATION: n is a, c, g, or t

<400> SEQUENCE: 1
aaggtttgta accaaactct gaccttagat gttatgattg tgtgcacaag ctctactctt    60
scagcaaang atagcaattt ggatctccaa ccntccaact tctctctaat atatatatna   120
a                                                                   121

<210> SEQ ID NO 2
<211> LENGTH: 121
<212> TYPE: DNA
<213> ORGANISM: Artificial sequence
<220> FEATURE:
<223> OTHER INFORMATION: Marker sequence

<400> SEQUENCE: 2
gccttctctt cgattttca ttgacgaagg tgatgatgct ttgccgaatg atccaatgct    60
yttccatact aaaagaacct accagcctag cactatcaaa cgcaagagga ctcatggtta   120
t                                                                   121

<210> SEQ ID NO 3
<211> LENGTH: 121
<212> TYPE: DNA
<213> ORGANISM: Artificial sequence
<220> FEATURE:
<223> OTHER INFORMATION: Marker sequence
<220> FEATURE:
<221> NAME/KEY: misc_feature
<222> LOCATION: (34)..(34)
<223> OTHER INFORMATION: n is a, c, g, or t

<400> SEQUENCE: 3
gcggaaggtc gcgatcctcg gggccgctgg gggnattggg cagcctttgt cacttctgat    60
raagcttaat cctcttgtta ccaagctagc tctttatgat attgctggta ctcctggcgt   120
g                                                                   121

<210> SEQ ID NO 4
<211> LENGTH: 121
<212> TYPE: DNA
<213> ORGANISM: Artificial sequence
<220> FEATURE:
<223> OTHER INFORMATION: Marker sequence

<400> SEQUENCE: 4
tttcttgaca ttggacgatg cgatcaagac tacaaatagg agggttaatg ccttggagag    60
ygttgtcaaa ccaaggttgg agaataccat tacctatatc aagggagagc tggatgagtt   120

```
                                                               g                                                         121

<210> SEQ ID NO 5
<211> LENGTH: 121
<212> TYPE: DNA
<213> ORGANISM: Artificial sequence
<220> FEATURE:
<223> OTHER INFORMATION: Marker sequence
<220> FEATURE:
<221> NAME/KEY: misc_feature
<222> LOCATION: (107)..(107)
<223> OTHER INFORMATION: n is a, c, g, or t

<400> SEQUENCE: 5
ctcaaaacca ccaccggtcg cattaagcaa tgctagagaa agtattctgt taggtgcaat        60
ygctgccaac ttgcaagcaa tcattgctcc catggagtga ccaaaancat gagctttagt       120
c                                                                       121

<210> SEQ ID NO 6
<211> LENGTH: 121
<212> TYPE: DNA
<213> ORGANISM: Artificial sequence
<220> FEATURE:
<223> OTHER INFORMATION: Marker sequence

<400> SEQUENCE: 6
ttcccaagag attatgtacc gtggtcctct agctcttttc ggtgtagggc ttgatgatta        60
yttcccaatg attaatatat attattaatt aactcagact ttgactgcac tatagtgtca       120
c                                                                       121

<210> SEQ ID NO 7
<211> LENGTH: 121
<212> TYPE: DNA
<213> ORGANISM: Artificial sequence
<220> FEATURE:
<223> OTHER INFORMATION: Marker sequence
<220> FEATURE:
<221> NAME/KEY: misc_feature
<222> LOCATION: (88)..(88)
<223> OTHER INFORMATION: n is a, c, g, or t

<400> SEQUENCE: 7
atcaaataac ttgatggttt ctgaggaatc ccatgatgtc aaatccgttt tattagctaa        60
mgcaaatgac cagtgcaatt tagccatntc aaaatgttgc tgtccaagtg caagtaaccc       120
t                                                                       121

<210> SEQ ID NO 8
<211> LENGTH: 121
<212> TYPE: DNA
<213> ORGANISM: Artificial sequence
<220> FEATURE:
<223> OTHER INFORMATION: Marker sequence

<400> SEQUENCE: 8
tgaatcagaa ggttctcttt gtgcaatttg tatccctggc atactataat atacgaaatg        60
waatcatctc ttataacctg gtaggacata ggtagaaaat ctaactggat gattagccaa       120
t                                                                       121

<210> SEQ ID NO 9
<211> LENGTH: 121
<212> TYPE: DNA
```

```
<213> ORGANISM: Artificial sequence
<220> FEATURE:
<223> OTHER INFORMATION: Marker sequence
<220> FEATURE:
<221> NAME/KEY: misc_feature
<222> LOCATION: (86)..(86)
<223> OTHER INFORMATION: n is a, c, g, or t
<220> FEATURE:
<221> NAME/KEY: misc_feature
<222> LOCATION: (102)..(102)
<223> OTHER INFORMATION: n is a, c, g, or t

<400> SEQUENCE: 9
gcttgaaaac atagttaagc aacttttcc tcaagctggt tgtcaatctt ggtcacctag    60
ratggtacag ccgatttgga aaacantatg ggaaactaaa antgcacaat tgagagaagg   120
t                                                                  121

<210> SEQ ID NO 10
<211> LENGTH: 121
<212> TYPE: DNA
<213> ORGANISM: Artificial sequence
<220> FEATURE:
<223> OTHER INFORMATION: Marker sequence

<400> SEQUENCE: 10
ttccattgct tctctgcctt tgatctcctt ccatttcttc agccctactt tgtcacgatt    60
stcaaagcta gggttagttt tactttgaa ttcgattttg aattcttaat tcttatgatt   120
t                                                                  121

<210> SEQ ID NO 11
<211> LENGTH: 121
<212> TYPE: DNA
<213> ORGANISM: Artificial sequence
<220> FEATURE:
<223> OTHER INFORMATION: Marker sequence
<220> FEATURE:
<221> NAME/KEY: misc_feature
<222> LOCATION: (13)..(13)
<223> OTHER INFORMATION: n is a, c, g, or t

<400> SEQUENCE: 11
tctggattga aanttaatgg cagcaaggtt gagaaagctg aagagaaggt ggaaaagatg    60
yctgctttga cgctgaaacc agagaaggtt aaagatgcat cgaaggctga ggctgttgtc   120
a                                                                  121

<210> SEQ ID NO 12
<211> LENGTH: 121
<212> TYPE: DNA
<213> ORGANISM: Artificial sequence
<220> FEATURE:
<223> OTHER INFORMATION: Marker sequence
<220> FEATURE:
<221> NAME/KEY: misc_feature
<222> LOCATION: (105)..(106)
<223> OTHER INFORMATION: n is a, c, g, or t

<400> SEQUENCE: 12
aatgacagta aaatggaaaa ttgttcaggt ttgagcctgc ggcatcatgc cctccaaata    60
yggagtccat tttaacaatc cttatttaga attactttgg taaannaagc agagagatta   120
a                                                                  121

<210> SEQ ID NO 13
<211> LENGTH: 121
```

```
<212> TYPE: DNA
<213> ORGANISM: Artificial sequence
<220> FEATURE:
<223> OTHER INFORMATION: Marker sequence

<400> SEQUENCE: 13
tttggaattt ataataggta gtgaaaagaa atgtctgaat tcagagctct ggcatgcatg     60
ygctggacct cttgtatgtt tgccaacaat cgggactcga gtagtttact tccctcaagg    120
c                                                                    121

<210> SEQ ID NO 14
<211> LENGTH: 121
<212> TYPE: DNA
<213> ORGANISM: Artificial sequence
<220> FEATURE:
<223> OTHER INFORMATION: Marker sequence
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (94)..(94)
<223> OTHER INFORMATION: n is a, c, g, or t

<400> SEQUENCE: 14
ttcatgcang catanattga tgtatgttgt atgtaaacaa taacagtaag ttttgtgttg     60
ytattgtagg tggagggaga atgcgaaaga agcngttgaa gaactgggag ttgctttgaa    120
a                                                                    121

<210> SEQ ID NO 15
<211> LENGTH: 121
<212> TYPE: DNA
<213> ORGANISM: Artificial sequence
<220> FEATURE:
<223> OTHER INFORMATION: Marker sequence
<220> FEATURE:
<221> NAME/KEY: misc_feature
<222> LOCATION: (91)..(91)
<223> OTHER INFORMATION: n is a, c, g, or t

<400> SEQUENCE: 15
caatcccacc tacacacaca tttccacacg ttgcattttg tgagtttata tactttctgt     60
ygttatcttc atagtcaacc ttgcttattt naacaataat ataaaagtgc ttttggtaaa    120
a                                                                    121

<210> SEQ ID NO 16
<211> LENGTH: 121
<212> TYPE: DNA
<213> ORGANISM: Artificial sequence
<220> FEATURE:
<223> OTHER INFORMATION: Marker sequence

<400> SEQUENCE: 16
tctttcgaat gtgtattctg aagtgaacag atgggatgat gcagagacga cgaggattag     60
yatgaagaat tgtaatgtag ataaattgcc tggatggagt tgtatagagg ttaatggaaa    120
g                                                                    121

<210> SEQ ID NO 17
```

```
<211> LENGTH: 121
<212> TYPE: DNA
<213> ORGANISM: Artificial sequence
<220> FEATURE:
<223> OTHER INFORMATION: Marker sequence
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (104)..(104)
<223> OTHER INFORMATION: n is a, c, g, or t
<220> FEATURE:
<221> NAME/KEY: misc_feature
<222> LOCATION: (115)..(115)
<223> OTHER INFORMATION: n is a, c, g, or t

<400> SEQUENCE: 17
caaancatag ccaacctctg ccagtaagtt caactaccct ccaagcacta cctttcacct      60
rcactacagc tacttcacct tcttctacct tctgcccgca aatnccatca ctacnccaac     120
c                                                                    121

<210> SEQ ID NO 18
<211> LENGTH: 121
<212> TYPE: DNA
<213> ORGANISM: Artificial sequence
<220> FEATURE:
<223> OTHER INFORMATION: Marker sequence

<400> SEQUENCE: 18
ggcttatgac caggcagctt ttgccatgag ggggtcgctg gcaattttga acttctcagt      60
sgaaacagtt gttgaatctt tgagagaagt caagtgccta aaagctggag gagagtcccc    120
t                                                                    121

<210> SEQ ID NO 19
<211> LENGTH: 121
<212> TYPE: DNA
<213> ORGANISM: Artificial sequence
<220> FEATURE:
<223> OTHER INFORMATION: Marker sequence
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (95)..(95)
<223> OTHER INFORMATION: n is a, c, g, or t

<400> SEQUENCE: 19
gcttcagaaa nccttaagtt ttatttcttc tgcatcatca cccctcttc cctatagttc      60 sgattactat attcccgccg tacaatttcc gaaancacct ccaaatctta ccgtttctca    120
a                                                                    121

<210> SEQ ID NO 20
<211> LENGTH: 121
<212> TYPE: DNA
<213> ORGANISM: Artificial sequence
<220> FEATURE:
<223> OTHER INFORMATION: Marker sequence
<220> FEATURE:
<221> NAME/KEY: misc_feature
<222> LOCATION: (34)..(34)
<223> OTHER INFORMATION: n is a, c, g, or t

<400> SEQUENCE: 20
```

```
ggcttatgac caggcagctt ttgccatgag gggntcgctg gcaattttga acttctcagt    60
sgaaacagtt gttgaatctt tgagagaagt caagtgccta aaagctggag gagagtcccc   120
t                                                                  121

<210> SEQ ID NO 21
<211> LENGTH: 121
<212> TYPE: DNA
<213> ORGANISM: Artificial sequence
<220> FEATURE:
<223> OTHER INFORMATION: Marker sequence
<220> FEATURE:
<221> NAME/KEY: misc_feature
<222> LOCATION: (6)..(6)
<223> OTHER INFORMATION: n is a, c, g, or t

<400> SEQUENCE: 21
agaaangaag aagaaaaaca atcgaatccc ctacctctta tcagaacatc gacccgaacc    60
scacaaacca cccaatattc cattgcctca tcaaaaattg cctcgccgcc ttcacccaga   120
a                                                                  121

<210> SEQ ID NO 22
<211> LENGTH: 121
<212> TYPE: DNA
<213> ORGANISM: Artificial sequence
<220> FEATURE:
<223> OTHER INFORMATION: Marker sequence
<220> FEATURE:
<221> NAME/KEY: misc_feature
<222> LOCATION: (9)..(9)
<223> OTHER INFORMATION: n is a, c, g, or t

<400> SEQUENCE: 22
aattaaaant aaatggatca cagacattag tatgaaagca agcaatatat aattagaatt    60
yagggctgtt ttgctagaaa tttgagtttt gcatcttgca ttttcaatat gcatgttaaa   120
a                                                                  121

<210> SEQ ID NO 23
<211> LENGTH: 121
<212> TYPE: DNA
<213> ORGANISM: Artificial sequence
<220> FEATURE:
<223> OTHER INFORMATION: Marker sequence
<220> FEATURE:
<221> NAME/KEY: misc_feature
<222> LOCATION: (12)..(12)
<223> OTHER INFORMATION: n is a, c, g, or t

<400> SEQUENCE: 23
cctaaccatg gnatttgtcc agctaagatc cccttcaaga gcaagattct caatatttag    60
yattagcggt ttcccaaact acactcaaga tcagggcagg ccctgtatac tgggttgctc   120
t                                                                  121

<210> SEQ ID NO 24
<211> LENGTH: 121
<212> TYPE: DNA
<213> ORGANISM: Artificial sequence
<220> FEATURE:
<223> OTHER INFORMATION: Marker sequence

<400> SEQUENCE: 24
ttaataaact gaaaaggagg attcattcat tcatgttaaa gtgcataaaa taatagatga    60
```

```
ygatgacgat gatgatttgg ttttcgattt tcttacccct gcaaaagctc gagaagctgt    120
g                                                                   121

<210> SEQ ID NO 25
<211> LENGTH: 121
<212> TYPE: DNA
<213> ORGANISM: Artificial sequence
<220> FEATURE:
<223> OTHER INFORMATION: Marker sequence
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t

<400> SEQUENCE: 25
aaangagaag agaaaaaanc atgccccttg tcttgctatt tatctcattt aatctcttaa    60
ytactgcatc cgcatctgat gcagaggaat cccttcttaa ctggagatcg tctcttataa    120
a                                                                   121

<210> SEQ ID NO 26
<211> LENGTH: 121
<212> TYPE: DNA
<213> ORGANISM: Artificial sequence
<220> FEATURE:
<223> OTHER INFORMATION: Marker sequence

<400> SEQUENCE: 26
atttcgttct aaggatgggg agtggcactg ttatgtggat aatgctgtct ggtactatgc    60
yatgttatta gttggtgaca gttatattat catacactac aaaaattgca tgggttaatt    120
g                                                                   121

<210> SEQ ID NO 27
<211> LENGTH: 121
<212> TYPE: DNA
<213> ORGANISM: Artificial sequence
<220> FEATURE:
<223> OTHER INFORMATION: Marker sequence

<400> SEQUENCE: 27
aattcctcgg agatggatat tcttctctgt aaatagcctc gagattaaat ggcctaaatc    60
raaacccatt aacatatgat atccaacaaa caaagtagga cccacagatg gaattccttc    120
a                                                                   121

<210> SEQ ID NO 28
<211> LENGTH: 315
<212> TYPE: DNA
<213> ORGANISM: Artificial sequence
<220> FEATURE:
<223> OTHER INFORMATION: Marker sequence

<400> SEQUENCE: 28
gtattcaagt tggcccacgt ttcctcaact ttatattgat ggggagtttt atggagggtg    60
tgatattact gttgaagcat accagagtgg ggaactgcag gaagcaatag aaaaagcaat    120
gtgttcttaa taatgtctca gttatarcct tctatgctcc attcatgcaa agttacactt    180
atttattaat tatgttatta tataatatat atctgcaatt tcatatttc agatctgtgg    240 atgacactta ccatttagtt gcttctggtg tttatattta ttctacaaag accatttact    300
```
gagttttcaa atgct 315

<210> SEQ ID NO 29
<211> LENGTH: 121
<212> TYPE: DNA
<213> ORGANISM: Artificial sequence
<220> FEATURE:
<223> OTHER INFORMATION: Marker sequence
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (99)..(99)
<223> OTHER INFORMATION: n is a, c, g, or t
<220> FEATURE:
<221> NAME/KEY: misc_feature
<222> LOCATION: (104)..(104)
<223> OTHER INFORMATION: n is a, c, g, or t
<220> FEATURE:
<221> NAME/KEY: misc_feature
<222> LOCATION: (114)..(114)
<223> OTHER INFORMATION: n is a, c, g, or t

<400> SEQUENCE: 29
catcttataa gtaatatact ttnaactttt aaggatcttc aaatattctc ttataaatta    60
raggccccaa gattaatcca aactgaattc ataaacaant aaantatcta tttnagtttc   120
t                                                                  121

<210> SEQ ID NO 30
<211> LENGTH: 121
<212> TYPE: DNA
<213> ORGANISM: Artificial sequence
<220> FEATURE:
<223> OTHER INFORMATION: Marker sequence
<220> FEATURE:
<221> NAME/KEY: misc_feature
<222> LOCATION: (58)..(58)
<223> OTHER INFORMATION: n is a, c, g, or t

<400> SEQUENCE: 30
aagctgtgat ttgtgcacac tggtgtgcag gtgcactgtg gatagtagca gttgtttnat    60
ygggtgatgg ctagtttgga ctgtggtcat taatgtttag aggctaaagc agctggttga   120
a                                                                  121

<210> SEQ ID NO 31
<211> LENGTH: 121
<212> TYPE: DNA
<213> ORGANISM: Artificial sequence
<220> FEATURE:
<223> OTHER INFORMATION: Marker sequence
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (97)..(97)
<223> OTHER INFORMATION: n is a, c, g, or t

<400> SEQUENCE: 31
aaattantta ctgtaaattc atcaaaccct aantcaatca tgcaagtgtg caattacacc    60
rctcaagtcc caccatcata caatacttat cgatttngat gactttcaaa gtttagtgct    120
a    121

<210> SEQ ID NO 32
<211> LENGTH: 121
<212> TYPE: DNA
<213> ORGANISM: Artificial sequence
<220> FEATURE:
<223> OTHER INFORMATION: Marker sequence

<400> SEQUENCE: 32
tttgaagcgg aaagatatgt ctgttgtggt gtcaatgcgc ataataaaga aagcatcaaa    60
kgggtaacta ctatttcaaa attcatgtat tcaatcatat tgtttatggg ctttcgtcgt    120
g    121

<210> SEQ ID NO 33
<211> LENGTH: 121
<212> TYPE: DNA
<213> ORGANISM: Artificial sequence
<220> FEATURE:
<223> OTHER INFORMATION: Marker sequence
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (106)..(106)
<223> OTHER INFORMATION: n is a, c, g, or t

<400> SEQUENCE: 33
ttactattaa tatcatccat ntaaactgtt acgtcatttc gaaattttca tctcactaaa    60
mggtgcaaat tgatatgatc catcgaaaat atttatttaa ccatcnattt caaacgtagt    120
t    121

<210> SEQ ID NO 34
<211> LENGTH: 121
<212> TYPE: DNA
<213> ORGANISM: Artificial sequence
<220> FEATURE:
<223> OTHER INFORMATION: Marker sequence
<220> FEATURE:
<221> NAME/KEY: misc_feature
<222> LOCATION: (16)..(16)
<223> OTHER INFORMATION: n is a, c, g, or t

<400> SEQUENCE: 34
ttgtcctaac ccctanatca tatagtatct gtgctccaat gccatattct cgtgaatcaa    60
yaggtaaccc caaatcttcg ttggcttcca cagtgtcacg gccagcatct tgcagattat    120
a    121

<210> SEQ ID NO 35
<211> LENGTH: 121
<212> TYPE: DNA
<213> ORGANISM: Artificial sequence
<220> FEATURE:
<223> OTHER INFORMATION: Marker sequence

<400> SEQUENCE: 35
cactaaagga tctgagcaaa cagctgtaga agttaatgat agtgaaagtg atttgaaccg    60
racaattttc ataaacaata ttccatttga tgctgacagt gaagaggtga aaaagagatt    120
c    121

<210> SEQ ID NO 36
<211> LENGTH: 121
<212> TYPE: DNA
<213> ORGANISM: Artificial sequence
<220> FEATURE:
<223> OTHER INFORMATION: Marker sequence
<220> FEATURE:
<221> NAME/KEY: misc_feature
<222> LOCATION: (16)..(16)
<223> OTHER INFORMATION: n is a, c, g, or t

<400> SEQUENCE: 36
tgcagatcca agtaantatg gtattttaa attgatagct atcgattatt ttggaccttt     60
yctcttttct gcatttgatg attgcaaatg tgttctgata ttattatttt tcatattttt    120
a                                                                    121

<210> SEQ ID NO 37
<211> LENGTH: 121
<212> TYPE: DNA
<213> ORGANISM: Artificial sequence
<220> FEATURE:
<223> OTHER INFORMATION: Marker sequence
<220> FEATURE:
<221> NAME/KEY: misc_feature
<222> LOCATION: (86)..(86)
<223> OTHER INFORMATION: n is a, c, g, or t

<400> SEQUENCE: 37
tttgatgcgc ctaggacccc aacttaaaga aagccacttt gaacgtgaga atgattctgc     60
rtatagttca tcatttagca tccccnttca caaataatgc aaaacttcat tctcagattg    120
c                                                                    121

<210> SEQ ID NO 38
<211> LENGTH: 121
<212> TYPE: DNA
<213> ORGANISM: Artificial sequence
<220> FEATURE:
<223> OTHER INFORMATION: Marker sequence

<400> SEQUENCE: 38
cgcttggcat cagtacagta gttgtaaatc atgaacttcc tctgcaccca cctcattctc     60
ytgtaactca ccgaatccaa ctcgtggtta taccaatctg ctggcgaagc cgttgacaac    120
a                                                                    121

<210> SEQ ID NO 39
<211> LENGTH: 121
<212> TYPE: DNA
<213> ORGANISM: Artificial sequence
<220> FEATURE:
<223> OTHER INFORMATION: Marker sequence
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t

<400> SEQUENCE: 39
anttaaggga gtttgtgtaa atatcaacaa ggatacgtag tccatcacta ctgtcatggn     60
rgttagacgc tccggctttg gtcagtgaag ttacaggttg aatcatggta gtgtcattca    120
a                                                                                     121

<210> SEQ ID NO 40
<211> LENGTH: 121
<212> TYPE: DNA
<213> ORGANISM: Artificial sequence
<220> FEATURE:
<223> OTHER INFORMATION: Marker sequence

<400> SEQUENCE: 40
ataaattggg atcagccaga aaatgctgaa acacacctat caacaattta taccagaatc      60
rctatttaca gccaacatgc tagaggcact tcaataaaat gtttagacag atcagtcatt     120
t                                                                     121

<210> SEQ ID NO 41
<211> LENGTH: 121
<212> TYPE: DNA
<213> ORGANISM: Artificial sequence
<220> FEATURE:
<223> OTHER INFORMATION: Marker sequence

<400> SEQUENCE: 41
aagaattcac ttgttgatag cttcattgtc ttgctggttt tcaactaatc tcatattcta      60
rgttgccctg aaattaaatg taaatgggaa aaatgtgaaa aggcaggtta gaatcttata     120
c                                                                     121

<210> SEQ ID NO 42
<211> LENGTH: 121
<212> TYPE: DNA
<213> ORGANISM: Artificial sequence
<220> FEATURE:
<223> OTHER INFORMATION: Marker sequence

<400> SEQUENCE: 42
ctcaataggc tttcttggtg aggcagagta atcggcatgt cttcttggtg aagcagagtg      60
rtcagtttgc cttcttggtg caggagagta cgaccttgat gtatggcgag ctcttgaaga     120
t                                                                     121

<210> SEQ ID NO 43
<211> LENGTH: 121
<212> TYPE: DNA
<213> ORGANISM: Artificial sequence
<220> FEATURE:
<223> OTHER INFORMATION: Marker sequence
<220> FEATURE:
<221> NAME/KEY: misc_feature
<222> LOCATION: (10)..(10)
<223> OTHER INFORMATION: n is a, c, g, or t

<400> SEQUENCE: 43
taggtaaaan ttaaagagaa aagcatcgta aataattaag tcacaaagca gcaggtgtgt      60
mgagtctaca ctaaaccaat cctttaagaa gtgtaccact tatatacgat taaatgtatt     120
a                                                                     121

<210> SEQ ID NO 44
<211> LENGTH: 121
<212> TYPE: DNA
<213> ORGANISM: Artificial sequence
<220> FEATURE:
<223> OTHER INFORMATION: Marker sequence

<400> SEQUENCE: 44

```
cctaattttt ctcctcaaat atcccatttg tttctaacta aatctcaaag gaaaagcttt    60
yattgcacga taacggttaa tttaatcatt cttcaagcta cacaatcagt caatcagtcg   120
t                                                                  121
```

<210> SEQ ID NO 45
<211> LENGTH: 121
<212> TYPE: DNA
<213> ORGANISM: Artificial sequence
<220> FEATURE:
<223> OTHER INFORMATION: Marker sequence
<220> FEATURE:
<221> NAME/KEY: misc_feature
<222> LOCATION: (34)..(34)
<223> OTHER INFORMATION: n is a, c, g, or t

<400> SEQUENCE: 45

```
aatttcgcga tgcatttgag attgttgtgg aaantatggt gcgtatggtc accaaatgag    60
rtatacacga ttcctttgta acgataaatg tttggatgac attcaattgt agaaccactg   120
a                                                                  121
```

<210> SEQ ID NO 46
<211> LENGTH: 121
<212> TYPE: DNA
<213> ORGANISM: Artificial sequence
<220> FEATURE:
<223> OTHER INFORMATION: Marker sequence
<220> FEATURE:
<221> NAME/KEY: misc_feature
<222> LOCATION: (118)..(118)
<223> OTHER INFORMATION: n is a, c, g, or t

<400> SEQUENCE: 46

```
aatcttccaa atggtctaag ttatacaacc ttaaagagca gccatatgat tcatgtatat    60
ygactgagat aaaatggaaa ggtgcaagtg gtggtggaaa ttataaacat tgcaaccntc   120
a                                                                  121
```

<210> SEQ ID NO 47
<211> LENGTH: 121
<212> TYPE: DNA
<213> ORGANISM: Artificial sequence
<220> FEATURE:
<223> OTHER INFORMATION: Marker sequence

<400> SEQUENCE: 47

```
ttctattatt aataaaaaga atactattat ccttaaatca acaatcttgg aatcctttag    60
ygaggcaaag ttaccgagtt tcgtttctct tgaacttgtt acaataatta caaaaccata   120
c                                                                  121
```

<210> SEQ ID NO 48
<211> LENGTH: 121
<212> TYPE: DNA
<213> ORGANISM: Artificial sequence
<220> FEATURE:
<223> OTHER INFORMATION: Marker sequence

<400> SEQUENCE: 48

```
catttttaaa tattggtaat atgcaaacat attttaagaa aatgccaagt agatgagcca    60
yagaagatac attcaatgtc tccaatgtag atttatttat ttttttttaaa acaagagaat   120 a                                                                  121
```

<210> SEQ ID NO 49
<211> LENGTH: 121
<212> TYPE: DNA
<213> ORGANISM: Artificial sequence
<220> FEATURE:
<223> OTHER INFORMATION: Marker sequence

<400> SEQUENCE: 49
atgtgttgtt agatctgctt tctaattctc aggatcgaaa gtccaatttc ttgctacctt     60
wtaaaagagc taccaacgac agcattcaag ctgttaatga agaagatgac acatcacgtc    120
c                                                                    121

<210> SEQ ID NO 50
<211> LENGTH: 121
<212> TYPE: DNA
<213> ORGANISM: Artificial sequence
<220> FEATURE:
<223> OTHER INFORMATION: Marker sequence

<400> SEQUENCE: 50
gtctctgtat aaccagcctg gtgccgctgg agctcctggt ggggctgact cagctggacc     60
kgtgcctggt tcggaacctt ctggaacttc gggtggtaag gggctgaaga tggtgatgtt    120
a                                                                    121

<210> SEQ ID NO 51
<211> LENGTH: 121
<212> TYPE: DNA
<213> ORGANISM: Artificial sequence
<220> FEATURE:
<223> OTHER INFORMATION: Marker sequence

<400> SEQUENCE: 51
aggagttttg ggcgacggga gtgagattgc cgtgaagaaa gtactggaat cagatctcca     60
ygatgatgaa ttcaagaatg aggttgagat aatcagcaag ttaaggcata gaaatcttgt    120
t                                                                    121

<210> SEQ ID NO 52
<211> LENGTH: 121
<212> TYPE: DNA
<213> ORGANISM: Artificial sequence
<220> FEATURE:
<223> OTHER INFORMATION: Marker sequence
<220> FEATURE:
<221> NAME/KEY: misc_feature
<222> LOCATION: (24)..(24)
<223> OTHER INFORMATION: n is a, c, g, or t

<400> SEQUENCE: 52
agccacaaca atagaccaaa atgnatttgc ttcttttgca tgacaatata aagatgatgc     60
wtgcttcttc aaccaggcag cacaaggatg acctgttcca tcgaagttat ttttaccact    120
t                                                                    121

<210> SEQ ID NO 53
<211> LENGTH: 121
<212> TYPE: DNA
<213> ORGANISM: Artificial sequence
<220> FEATURE:
<223> OTHER INFORMATION: Marker sequence

<400> SEQUENCE: 53
ttcattcagg tatttatcat ctctgtggag tgctagcgca tgaccgataa agtcaattgt     60

```
rttgtcatcc aatccatatt ttgatatgag ctctttagta gtcaccttg taaggtccaa    120 t                                                                  121

<210> SEQ ID NO 54
<211> LENGTH: 121
<212> TYPE: DNA
<213> ORGANISM: Artificial sequence
<220> FEATURE:
<223> OTHER INFORMATION: Marker sequence

<400> SEQUENCE: 54
cctctgaaat taagatactt tctggagtag aaacaagtga agctgctact gtttcaggta    60
ytggcagcga ttcttcttcg tcagaactat taccttcgga ttcttcttct attgggtttt   120
c                                                                  121

<210> SEQ ID NO 55
<211> LENGTH: 121
<212> TYPE: DNA
<213> ORGANISM: Artificial sequence
<220> FEATURE:
<223> OTHER INFORMATION: Marker sequence

<400> SEQUENCE: 55
gaaaaagacg acgaatctgc attttcgtcc tgaaagttaa cgatcgccag ccgcctatca    60
ycctcagctt cttcgacgtc gccaagggaa ggtgaagaat cgaactcgac gtcggagtct   120
g                                                                  121

<210> SEQ ID NO 56
<211> LENGTH: 121
<212> TYPE: DNA
<213> ORGANISM: Artificial sequence
<220> FEATURE:
<223> OTHER INFORMATION: Marker sequence
<220> FEATURE:
<221> NAME/KEY: misc_feature
<222> LOCATION: (12)..(12)
<223> OTHER INFORMATION: n is a, c, g, or t

<400> SEQUENCE: 56
tattggtaaa antaagtaca aaatataaga agattaagtt taataatcct ggttccttta    60
wattgtccag actctcccaa gcaaaacaag tgagaaatta gcattggctt caaagttcaa   120
a                                                                  121

<210> SEQ ID NO 57
<211> LENGTH: 121
<212> TYPE: DNA
<213> ORGANISM: Artificial sequence
<220> FEATURE:
<223> OTHER INFORMATION: Marker sequence
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t
<220> FEATURE:
<221> NAME/KEY: misc_feature
<222> LOCATION: (84)..(84)
<223> OTHER INFORMATION: n is a, c, g, or t

<400> SEQUENCE: 57
```

-continued

```
gattagattt cgagaatgga gaaaanggga gtgttggaag aaacagtaaa anggaataag    60
ygtaggtgac cgttggagat tttngtttat aaaatgctga tttacgatta agctttagcc   120
a                                                                  121
```

<210> SEQ ID NO 58
<211> LENGTH: 121
<212> TYPE: DNA
<213> ORGANISM: Artificial sequence
<220> FEATURE:
<223> OTHER INFORMATION: Marker sequence

<400> SEQUENCE: 58

```
tggtatacaa atacagctcg atattggtta ctaattgctt gatattggta tggtaatacc    60
rtaatagccc taactagctc taggtctaaa atttatcttt tcatggaaaa tgacatagtt   120
t                                                                  121
```

<210> SEQ ID NO 59
<211> LENGTH: 121
<212> TYPE: DNA
<213> ORGANISM: Artificial sequence
<220> FEATURE:
<223> OTHER INFORMATION: Marker sequence

<400> SEQUENCE: 59

```
agattgtgtg tttcctagga ttcctcagtt agcagttatt ggttttcgg gtagtcttgc     60 kaatctttac acgtttgaga taaggtcaat gtgggtggct cattttcttg atggagggtt   120
t                                                                  121
```

<210> SEQ ID NO 60
<211> LENGTH: 121
<212> TYPE: DNA
<213> ORGANISM: Artificial sequence
<220> FEATURE:
<223> OTHER INFORMATION: Marker sequence
<220> FEATURE:
<221> NAME/KEY: misc_feature
<222> LOCATION: (87)..(87)
<223> OTHER INFORMATION: n is a, c, g, or t
<220> FEATURE:
<221> NAME/KEY: misc_feature
<222> LOCATION: (90)..(90)
<223> OTHER INFORMATION: n is a, c, g, or t

<400> SEQUENCE: 60

```
gccctgctcc agagcttatt ctcacgactg gacggagtgc cctttcgtgc atccaggcga    60
raacgcgcgt cgaagagact tgaaaangtn cgtctacagc tgcgttccgt gtcctgagtt   120
c                                                                  121
```

<210> SEQ ID NO 61
<211> LENGTH: 121
<212> TYPE: DNA
<213> ORGANISM: Artificial sequence
<220> FEATURE:
<223> OTHER INFORMATION: Marker sequence
<220> FEATURE:
<221> NAME/KEY: misc_feature
<222> LOCATION: (12)..(12)
<223> OTHER INFORMATION: n is a, c, g, or t

<400> SEQUENCE: 61

```
tattaaagtt tngtccaaaa gaaggcgata gtggatcaac tgaatatcca acaagtccat    60
rgttattgtt gttattacga taattggatg gagagcttcc acctggactg ccaattaaag   120
```

```
<210> SEQ ID NO 62
<211> LENGTH: 121
<212> TYPE: DNA
<213> ORGANISM: Artificial sequence
<220> FEATURE:
<223> OTHER INFORMATION: Marker sequence

<400> SEQUENCE: 62
tgccttccag cataaacacc cctgcacaaa atgctacatt tgttaggacg tgtcttgcta     60
ytgagcaaaa atacccaaat tggttgactc agttgcctcc aaatgataat aataataaaa   120
c                                                                   121

<210> SEQ ID NO 63
<211> LENGTH: 121
<212> TYPE: DNA
<213> ORGANISM: Artificial sequence
<220> FEATURE:
<223> OTHER INFORMATION: Marker sequence

<400> SEQUENCE: 63
aactgtagta cagaaataaa ctagtctgaa cccatgcttc gcacatggaa tcgcacaaca     60
ygattaaata aaatttgcat agtacatttc aggtttgcga tgtttgacaa atacatcaga   120
t                                                                   121

<210> SEQ ID NO 64
<211> LENGTH: 116
<212> TYPE: DNA
<213> ORGANISM: Artificial sequence
<220> FEATURE:
<223> OTHER INFORMATION: Marker sequence
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (75)..(75)
<223> OTHER INFORMATION: n is a, c, g, or t

<400> SEQUENCE: 64
ctatagtgca gagcttgaac ttgaaccaaa gcagtatcat gtaattgcat ttgaarntcc     60
agcagattct aaaantttct gttatattgt gcaagcacat atggagatgt taggaa       116

<210> SEQ ID NO 65
<211> LENGTH: 121
<212> TYPE: DNA
<213> ORGANISM: Artificial sequence
<220> FEATURE:
<223> OTHER INFORMATION: Marker sequence

<400> SEQUENCE: 65
tcaggttgga gcggacccgg aaagtgcagc cgcctacaat ggaggtttgg ttaggaagtt     60
yaatggtgga ggagggacgc cgttgatgcc gaagaggaag tttgagacgt acattttgc   120 g                                                                   121

<210> SEQ ID NO 66
<211> LENGTH: 121
<212> TYPE: DNA
<213> ORGANISM: Artificial sequence
<220> FEATURE:
```

<223> OTHER INFORMATION: Marker sequence

<400> SEQUENCE: 66

```
caatgagaca tagccaattg gcatttcgca gcactgacct aaaatggatt cataatcaaa    60
yccttctaaa ggcaaaccat tcaaacttct attagtgatt ctctttacgg cctcacgtcg   120
a                                                                    121
```

<210> SEQ ID NO 67
<211> LENGTH: 121
<212> TYPE: DNA
<213> ORGANISM: Artificial sequence
<220> FEATURE:
<223> OTHER INFORMATION: Marker sequence
<220> FEATURE:
<221> NAME/KEY: misc_feature
<222> LOCATION: (26)..(26)
<223> OTHER INFORMATION: n is a, c, g, or t

<400> SEQUENCE: 67

```
acaattgcta tcttcgtttt tacatnaccg tttggtggtc gataacatag atgaatgaaa    60
ygaggaggat ttgatgaagc agcagcaaca cctaaatatg aacccatctt caattccgtg   120
c                                                                    121
```

<210> SEQ ID NO 68
<211> LENGTH: 235
<212> TYPE: DNA
<213> ORGANISM: Artificial sequence
<220> FEATURE:
<223> OTHER INFORMATION: Marker sequence

<400> SEQUENCE: 68

```
tgtggattag ctactaaaaa ttatacatga tttcaggaaa tgaagcacat tattcaatca    60
taaagcaagc tcagctggtt cacctggatk asgtkystgt saarmwymmm twmwscyryt   120
kaaccmtmcy mwmkyrrmmk krykwtasay akgcykkkcy ywykmygwrw ymwttymykm   180
kmwrscyrww wwrmytmkkm mkmwyyaymc kmmmyrttwm aykyykywrc gactc        235
```

<210> SEQ ID NO 69
<211> LENGTH: 121
<212> TYPE: DNA
<213> ORGANISM: Artificial sequence
<220> FEATURE:
<223> OTHER INFORMATION: Marker sequence
<220> FEATURE:
<221> NAME/KEY: misc_feature
<222> LOCATION: (97)..(97)
<223> OTHER INFORMATION: n is a, c, g, or t

<400> SEQUENCE: 69

```
agatataact acttttggat tatgggctta tgatgctgct tttgccttag caatggctac    60
ygagtcagct cagccagctt ataactatag taatgangtt gctaacggta atttaatgaa   120
g                                                                    121
```

<210> SEQ ID NO 70
<211> LENGTH: 121
<212> TYPE: DNA
<213> ORGANISM: Artificial sequence
<220> FEATURE:
<223> OTHER INFORMATION: Marker sequence
<220> FEATURE:
<221> NAME/KEY: misc_feature
<222> LOCATION: (92)..(92)
<223> OTHER INFORMATION: n is a, c, g, or t
```

<400> SEQUENCE: 70
agaaattaca gttgataaag tagccgatga aggcaatctt acactagcac aaagttttag    60
ygataaccac agtgataggg attcaagaaa ancactggct cacttaacaa tgagcaaatc   120
t                                                                   121

<210> SEQ ID NO 71
<211> LENGTH: 141
<212> TYPE: DNA
<213> ORGANISM: Artificial sequence
<220> FEATURE:
<223> OTHER INFORMATION: Marker sequence
<220> FEATURE:
<221> NAME/KEY: misc_feature
<222> LOCATION: (55)..(55)
<223> OTHER INFORMATION: n is a, c, g, or t

<400> SEQUENCE: 71
gcattccata accaccattc aacatgcact ccactggcat gcaatatgtt attanatttt    60
atgatcaagy actttcatca gctgttacaa gttgtgactg ttcgctgcta ataacttaat   120
aattctgtca ctacaacaaa t                                             141

<210> SEQ ID NO 72
<211> LENGTH: 121
<212> TYPE: DNA
<213> ORGANISM: Artificial sequence
<220> FEATURE:
<223> OTHER INFORMATION: Marker sequence
<220> FEATURE:
<221> NAME/KEY: misc_feature
<222> LOCATION: (50)..(50)
<223> OTHER INFORMATION: n is a, c, g, or t
<220> FEATURE:
<221> NAME/KEY: misc_feature
<222> LOCATION: (93)..(93)
<223> OTHER INFORMATION: n is a, c, g, or t

<400> SEQUENCE: 72
tggtgtttct ggagctgaag catttggaga agtattcaca ttgaaggaan taggcatttg    60
macagtgcca tagcaatttg gctcagaacc agncgcacag atcaaaggat ttcctacaat   120
g                                                                   121

<210> SEQ ID NO 73
<211> LENGTH: 121
<212> TYPE: DNA
<213> ORGANISM: Artificial sequence
<220> FEATURE:
<223> OTHER INFORMATION: Marker sequence

<400> SEQUENCE: 73
tgactctata ctagatgatg agttctcctt ctccaacctc aacttatcac atctgctatt    60
ytgactaaca ttcattgcat cacttctgct tctttgaact ctttgttgca atccaacatt   120
c                                                                   121

<210> SEQ ID NO 74
<211> LENGTH: 121
<212> TYPE: DNA
<213> ORGANISM: Artificial sequence
<220> FEATURE:
<223> OTHER INFORMATION: Marker sequence
<220> FEATURE:
<221> NAME/KEY: misc_feature
<222> LOCATION: (11)..(11)

```
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 74
atggcttgaa nggtcgctca tcanccccca gcggtccgac cactctatat ccaatctcct    60
scgcctcgat tatcttctcc tctttactct tcccactcac tttaaacttc ctcacggatc   120
c                                                                   121

<210> SEQ ID NO 75
<211> LENGTH: 20
<212> TYPE: DNA
<213> ORGANISM: Artificial sequence
<220> FEATURE:
<223> OTHER INFORMATION: VIC-labeled probe

<400> SEQUENCE: 75
agctctactc ttccagcaaa                                                 20

<210> SEQ ID NO 76
<211> LENGTH: 20
<212> TYPE: DNA
<213> ORGANISM: Artificial sequence
<220> FEATURE:
<223> OTHER INFORMATION: VIC-labeled probe

<400> SEQUENCE: 76
atgatccaat gcttttccat                                                 20

<210> SEQ ID NO 77
<211> LENGTH: 18
<212> TYPE: DNA
<213> ORGANISM: Artificial sequence
<220> FEATURE:
<223> OTHER INFORMATION: VIC-labeled probe

<400> SEQUENCE: 77
tcacttctga taaagctt                                                   18

<210> SEQ ID NO 78
<211> LENGTH: 17
<212> TYPE: DNA
<213> ORGANISM: Artificial sequence
<220> FEATURE:
<223> OTHER INFORMATION: VIC-labeled probe

<400> SEQUENCE: 78
ccttggagag tgttgtc                                                    17

<210> SEQ ID NO 79
<211> LENGTH: 19
<212> TYPE: DNA
<213> ORGANISM: Artificial sequence
<220> FEATURE:
<223> OTHER INFORMATION: VIC-labeled probe

<400> SEQUENCE: 79
atcattggga aataatcat                                                  19

<210> SEQ ID NO 80
<211> LENGTH: 19
<212> TYPE: DNA
<213> ORGANISM: Artificial sequence
```

```
<220> FEATURE:
<223> OTHER INFORMATION: VIC-labeled probe

<400> SEQUENCE: 80
ctggtcattt gctttagct                                                19

<210> SEQ ID NO 81
<211> LENGTH: 18
<212> TYPE: DNA
<213> ORGANISM: Artificial sequence
<220> FEATURE:
<223> OTHER INFORMATION: VIC-labeled probe

<400> SEQUENCE: 81
atacgaaatg aaatcatc                                                 18

<210> SEQ ID NO 82
<211> LENGTH: 19
<212> TYPE: DNA
<213> ORGANISM: Artificial sequence
<220> FEATURE:
<223> OTHER INFORMATION: VIC-labeled probe

<400> SEQUENCE: 82
ttggtcacct agaatggta                                                19

<210> SEQ ID NO 83
<211> LENGTH: 17
<212> TYPE: DNA
<213> ORGANISM: Artificial sequence
<220> FEATURE:
<223> OTHER INFORMATION: VIC-labeled probe

<400> SEQUENCE: 83
ctagctttga gaatcgt                                                  17

<210> SEQ ID NO 84
<211> LENGTH: 16
<212> TYPE: DNA
<213> ORGANISM: Artificial sequence
<220> FEATURE:
<223> OTHER INFORMATION: VIC-labeled probe

<400> SEQUENCE: 84
atggactcca tatttg                                                   16

<210> SEQ ID NO 85
<211> LENGTH: 15
<212> TYPE: DNA
<213> ORGANISM: Artificial sequence
<220> FEATURE:
<223> OTHER INFORMATION: VIC-labeled probe

<400> SEQUENCE: 85
tccagcacat gcatg                                                    15

<210> SEQ ID NO 86
<211> LENGTH: 19
<212> TYPE: DNA
<213> ORGANISM: Artificial sequence
<220> FEATURE:
<223> OTHER INFORMATION: VIC-labeled probe

<400> SEQUENCE: 86
ccacctacaa taacaacac                                                19
```

<210> SEQ ID NO 87
<211> LENGTH: 19
<212> TYPE: DNA
<213> ORGANISM: Artificial sequence
<220> FEATURE:
<223> OTHER INFORMATION: VIC-labeled probe

<400> SEQUENCE: 87
actttctgtt gttatcttc                                                19

<210> SEQ ID NO 88
<211> LENGTH: 20
<212> TYPE: DNA
<213> ORGANISM: Artificial sequence
<220> FEATURE:
<223> OTHER INFORMATION: VIC-labeled probe

<400> SEQUENCE: 88
acaattcttc atactaatcc                                               20

<210> SEQ ID NO 89
<211> LENGTH: 17
<212> TYPE: DNA
<213> ORGANISM: Artificial sequence
<220> FEATURE:
<223> OTHER INFORMATION: VIC-labeled probe

<400> SEQUENCE: 89
cttctcagtc gaaacag                                                  17

<210> SEQ ID NO 90
<211> LENGTH: 19
<212> TYPE: DNA
<213> ORGANISM: Artificial sequence
<220> FEATURE:
<223> OTHER INFORMATION: VIC-labeled probe

<400> SEQUENCE: 90
ccctatagtt ccgattact                                                19

<210> SEQ ID NO 91
<211> LENGTH: 17
<212> TYPE: DNA
<213> ORGANISM: Artificial sequence
<220> FEATURE:
<223> OTHER INFORMATION: VIC-labeled probe

<400> SEQUENCE: 91
cttctcagtc gaaacag                                                  17

<210> SEQ ID NO 92
<211> LENGTH: 15
<212> TYPE: DNA
<213> ORGANISM: Artificial sequence
<220> FEATURE:
<223> OTHER INFORMATION: VIC-labeled probe

<400> SEQUENCE: 92
ccgaacccca caaac                                                    15

<210> SEQ ID NO 93
<211> LENGTH: 16
<212> TYPE: DNA
<213> ORGANISM: Artificial sequence
<220> FEATURE:
<223> OTHER INFORMATION: VIC-labeled probe

```
<400> SEQUENCE: 93
acagccctaa attcta                                                      16

<210> SEQ ID NO 94
<211> LENGTH: 18
<212> TYPE: DNA
<213> ORGANISM: Artificial sequence
<220> FEATURE:
<223> OTHER INFORMATION: VIC-labeled probe

<400> SEQUENCE: 94
accgctaata ctaaatat                                                    18

<210> SEQ ID NO 95
<211> LENGTH: 17
<212> TYPE: DNA
<213> ORGANISM: Artificial sequence
<220> FEATURE:
<223> OTHER INFORMATION: VIC-labeled probe

<400> SEQUENCE: 95
catcgtcatc atcatct                                                     17

<210> SEQ ID NO 96
<211> LENGTH: 18
<212> TYPE: DNA
<213> ORGANISM: Artificial sequence
<220> FEATURE:
<223> OTHER INFORMATION: VIC-labeled probe

<400> SEQUENCE: 96
cggatgcagt aattaaga                                                    18

<210> SEQ ID NO 97
<211> LENGTH: 21
<212> TYPE: DNA
<213> ORGANISM: Artificial sequence
<220> FEATURE:
<223> OTHER INFORMATION: VIC-labeled probe

<400> SEQUENCE: 97
tgttaatggg ttttgattta g                                                21

<210> SEQ ID NO 98
<211> LENGTH: 20
<212> TYPE: DNA
<213> ORGANISM: Artificial sequence
<220> FEATURE:
<223> OTHER INFORMATION: VIC-labeled probe

<400> SEQUENCE: 98
agcatagaag gttataactg                                                  20

<210> SEQ ID NO 99
<211> LENGTH: 20
<212> TYPE: DNA
<213> ORGANISM: Artificial sequence
<220> FEATURE:
<223> OTHER INFORMATION: VIC-labeled probe

<400> SEQUENCE: 99
atttcagggc aacttagaat                                                  20

<210> SEQ ID NO 100
```

<210> SEQ ID NO 100
<211> LENGTH: 19
<212> TYPE: DNA
<213> ORGANISM: Artificial sequence
<220> FEATURE:
<223> OTHER INFORMATION: VIC-labeled probe

<400> SEQUENCE: 100
tgaagcagag tgatcagtt                                                  19

<210> SEQ ID NO 101
<211> LENGTH: 15
<212> TYPE: DNA
<213> ORGANISM: Artificial sequence
<220> FEATURE:
<223> OTHER INFORMATION: VIC-labeled probe

<400> SEQUENCE: 101
tcgtgcaata aaagc                                                      15

<210> SEQ ID NO 102
<211> LENGTH: 19
<212> TYPE: DNA
<213> ORGANISM: Artificial sequence
<220> FEATURE:
<223> OTHER INFORMATION: VIC-labeled probe

<400> SEQUENCE: 102
caccaaatga gatatacac                                                  19

<210> SEQ ID NO 103
<211> LENGTH: 17
<212> TYPE: DNA
<213> ORGANISM: Artificial sequence
<220> FEATURE:
<223> OTHER INFORMATION: VIC-labeled probe

<400> SEQUENCE: 103
ctttgcctca ctaaagg                                                    17

<210> SEQ ID NO 104
<211> LENGTH: 15
<212> TYPE: DNA
<213> ORGANISM: Artificial sequence
<220> FEATURE:
<223> OTHER INFORMATION: VIC-labeled probe

<400> SEQUENCE: 104
caggcacagg tccag                                                      15

<210> SEQ ID NO 105
<211> LENGTH: 19
<212> TYPE: DNA
<213> ORGANISM: Artificial sequence
<220> FEATURE:
<223> OTHER INFORMATION: VIC-labeled probe

<400> SEQUENCE: 105
tcagatctcc atgatgatg                                                  19

<210> SEQ ID NO 106
<211> LENGTH: 17
<212> TYPE: DNA
<213> ORGANISM: Artificial sequence
<220> FEATURE:
<223> OTHER INFORMATION: VIC-labeled probe

<400> SEQUENCE: 106
aagatgatgc atgcttc                                                17

<210> SEQ ID NO 107
<211> LENGTH: 17
<212> TYPE: DNA
<213> ORGANISM: Artificial sequence
<220> FEATURE:
<223> OTHER INFORMATION: VIC-labeled probe

<400> SEQUENCE: 107
tcgctgccaa tacctga                                                17

<210> SEQ ID NO 108
<211> LENGTH: 20
<212> TYPE: DNA
<213> ORGANISM: Artificial sequence
<220> FEATURE:
<223> OTHER INFORMATION: VIC-labeled probe

<400> SEQUENCE: 108
caagaaatga gcagtaatat                                             20

<210> SEQ ID NO 109
<211> LENGTH: 15
<212> TYPE: DNA
<213> ORGANISM: Artificial sequence
<220> FEATURE:
<223> OTHER INFORMATION: VIC-labeled probe

<400> SEQUENCE: 109
ccgccatagc tctaa                                                  15

<210> SEQ ID NO 110
<211> LENGTH: 20
<212> TYPE: DNA
<213> ORGANISM: Artificial sequence
<220> FEATURE:
<223> OTHER INFORMATION: VIC-labeled probe

<400> SEQUENCE: 110
tgaaagtgtg tcatcaatta                                             20

<210> SEQ ID NO 111
<211> LENGTH: 15
<212> TYPE: DNA
<213> ORGANISM: Artificial sequence
<220> FEATURE:
<223> OTHER INFORMATION: VIC-labeled probe

<400> SEQUENCE: 111
cctggattag gcctg                                                  15

<210> SEQ ID NO 112
<211> LENGTH: 18
<212> TYPE: DNA
<213> ORGANISM: Artificial sequence
<220> FEATURE:
<223> OTHER INFORMATION: VIC-labeled probe

<400> SEQUENCE: 112
caatggctac tgagtcag                                               18

<210> SEQ ID NO 113
<211> LENGTH: 19
<212> TYPE: DNA

```
<213> ORGANISM: Artificial sequence
<220> FEATURE:
<223> OTHER INFORMATION: VIC-labeled probe

<400> SEQUENCE: 113
actgtggtta tcactaaaa                                                19

<210> SEQ ID NO 114
<211> LENGTH: 19
<212> TYPE: DNA
<213> ORGANISM: Artificial sequence
<220> FEATURE:
<223> OTHER INFORMATION: VIC-labeled probe

<400> SEQUENCE: 114
ctgatgaaag tgcttgatc                                                19

<210> SEQ ID NO 115
<211> LENGTH: 16
<212> TYPE: DNA
<213> ORGANISM: Artificial sequence
<220> FEATURE:
<223> OTHER INFORMATION: VIC-labeled probe

<400> SEQUENCE: 115
gagttacctc ttagct                                                   16

<210> SEQ ID NO 116
<211> LENGTH: 18
<212> TYPE: DNA
<213> ORGANISM: Artificial sequence
<220> FEATURE:
<223> OTHER INFORMATION: FAM-labeled probe

<400> SEQUENCE: 116
ctctactctt gcagcaaa                                                 18

<210> SEQ ID NO 117
<211> LENGTH: 19
<212> TYPE: DNA
<213> ORGANISM: Artificial sequence
<220> FEATURE:
<223> OTHER INFORMATION: FAM-labeled probe

<400> SEQUENCE: 117
tgatccaatg ctcttccat                                                19

<210> SEQ ID NO 118
<211> LENGTH: 16
<212> TYPE: DNA
<213> ORGANISM: Artificial sequence
<220> FEATURE:
<223> OTHER INFORMATION: FAM-labeled probe

<400> SEQUENCE: 118
acttctgatg aagctt                                                   16

<210> SEQ ID NO 119
<211> LENGTH: 15
<212> TYPE: DNA
<213> ORGANISM: Artificial sequence
<220> FEATURE:
<223> OTHER INFORMATION: FAM-labeled probe

<400> SEQUENCE: 119
ttggagagcg ttgtc                                                    15
```

```
<210> SEQ ID NO 120
<211> LENGTH: 17
<212> TYPE: DNA
<213> ORGANISM: Artificial sequence
<220> FEATURE:
<223> OTHER INFORMATION: FAM-labeled probe

<400> SEQUENCE: 120
cattgggaag taatcat                                                    17

<210> SEQ ID NO 121
<211> LENGTH: 18
<212> TYPE: DNA
<213> ORGANISM: Artificial sequence
<220> FEATURE:
<223> OTHER INFORMATION: FAM-labeled probe

<400> SEQUENCE: 121
tggtcatttg cgttagct                                                   18

<210> SEQ ID NO 122
<211> LENGTH: 18
<212> TYPE: DNA
<213> ORGANISM: Artificial sequence
<220> FEATURE:
<223> OTHER INFORMATION: FAM-labeled probe

<400> SEQUENCE: 122
atacgaaatg taatcatc                                                   18

<210> SEQ ID NO 123
<211> LENGTH: 18
<212> TYPE: DNA
<213> ORGANISM: Artificial sequence
<220> FEATURE:
<223> OTHER INFORMATION: FAM-labeled probe

<400> SEQUENCE: 123
tggtcaccta ggatggta                                                   18

<210> SEQ ID NO 124
<211> LENGTH: 17
<212> TYPE: DNA
<213> ORGANISM: Artificial sequence
<220> FEATURE:
<223> OTHER INFORMATION: FAM-labeled probe

<400> SEQUENCE: 124
ctagctttga caatcgt                                                    17

<210> SEQ ID NO 125
<211> LENGTH: 16
<212> TYPE: DNA
<213> ORGANISM: Artificial sequence
<220> FEATURE:
<223> OTHER INFORMATION: FAM-labeled probe

<400> SEQUENCE: 125
atggactccg tatttg                                                     16

<210> SEQ ID NO 126
<211> LENGTH: 13
<212> TYPE: DNA
<213> ORGANISM: Artificial sequence
<220> FEATURE:
```

```
<223> OTHER INFORMATION: FAM-labeled probe

<400> SEQUENCE: 126
cagcgcatgc atg                                                    13

<210> SEQ ID NO 127
<211> LENGTH: 18
<212> TYPE: DNA
<213> ORGANISM: Artificial sequence
<220> FEATURE:
<223> OTHER INFORMATION: FAM-labeled probe

<400> SEQUENCE: 127
cacctacaat agcaacac                                               18

<210> SEQ ID NO 128
<211> LENGTH: 16
<212> TYPE: DNA
<213> ORGANISM: Artificial sequence
<220> FEATURE:
<223> OTHER INFORMATION: FAM-labeled probe

<400> SEQUENCE: 128
ttctgtcgtt atcttc                                                 16

<210> SEQ ID NO 129
<211> LENGTH: 18
<212> TYPE: DNA
<213> ORGANISM: Artificial sequence
<220> FEATURE:
<223> OTHER INFORMATION: FAM-labeled probe

<400> SEQUENCE: 129
aattcttcat gctaatcc                                               18

<210> SEQ ID NO 130
<211> LENGTH: 16
<212> TYPE: DNA
<213> ORGANISM: Artificial sequence
<220> FEATURE:
<223> OTHER INFORMATION: FAM-labeled probe

<400> SEQUENCE: 130
ttctcagtgg aaacag                                                 16

<210> SEQ ID NO 131
<211> LENGTH: 18
<212> TYPE: DNA
<213> ORGANISM: Artificial sequence
<220> FEATURE:
<223> OTHER INFORMATION: FAM-labeled probe

<400> SEQUENCE: 131
cctatagttc ggattact                                               18

<210> SEQ ID NO 132
<211> LENGTH: 16
<212> TYPE: DNA
<213> ORGANISM: Artificial sequence
<220> FEATURE:
<223> OTHER INFORMATION: FAM-labeled probe

<400> SEQUENCE: 132
ttctcagtgg aaacag                                                 16
```

```
<210> SEQ ID NO 133
<211> LENGTH: 14
<212> TYPE: DNA
<213> ORGANISM: Artificial sequence
<220> FEATURE:
<223> OTHER INFORMATION: FAM-labeled probe

<400> SEQUENCE: 133
cgaaccgcac aaac                                                     14

<210> SEQ ID NO 134
<211> LENGTH: 14
<212> TYPE: DNA
<213> ORGANISM: Artificial sequence
<220> FEATURE:
<223> OTHER INFORMATION: FAM-labeled probe

<400> SEQUENCE: 134
agccctgaat tcta                                                     14

<210> SEQ ID NO 135
<211> LENGTH: 16
<212> TYPE: DNA
<213> ORGANISM: Artificial sequence
<220> FEATURE:
<223> OTHER INFORMATION: FAM-labeled probe

<400> SEQUENCE: 135
cgctaatgct aaatat                                                   16

<210> SEQ ID NO 136
<211> LENGTH: 17
<212> TYPE: DNA
<213> ORGANISM: Artificial sequence
<220> FEATURE:
<223> OTHER INFORMATION: FAM-labeled probe

<400> SEQUENCE: 136
catcgtcatc gtcatct                                                  17

<210> SEQ ID NO 137
<211> LENGTH: 18
<212> TYPE: DNA
<213> ORGANISM: Artificial sequence
<220> FEATURE:
<223> OTHER INFORMATION: FAM-labeled probe

<400> SEQUENCE: 137
cggatgcagt agttaaga                                                 18

<210> SEQ ID NO 138
<211> LENGTH: 17
<212> TYPE: DNA
<213> ORGANISM: Artificial sequence
<220> FEATURE:
<223> OTHER INFORMATION: FAM-labeled probe

<400> SEQUENCE: 138
aatgggtttc gatttag                                                  17

<210> SEQ ID NO 139
<211> LENGTH: 18
<212> TYPE: DNA
<213> ORGANISM: Artificial sequence
<220> FEATURE:
<223> OTHER INFORMATION: FAM-labeled probe
```

<400> SEQUENCE: 139
catagaaggc tataactg					18

<210> SEQ ID NO 140
<211> LENGTH: 17
<212> TYPE: DNA
<213> ORGANISM: Artificial sequence
<220> FEATURE:
<223> OTHER INFORMATION: FAM-labeled probe

<400> SEQUENCE: 140
tcagggcaac ctagaat					17

<210> SEQ ID NO 141
<211> LENGTH: 17
<212> TYPE: DNA
<213> ORGANISM: Artificial sequence
<220> FEATURE:
<223> OTHER INFORMATION: FAM-labeled probe

<400> SEQUENCE: 141
aagcagagtg gtcagtt					17

<210> SEQ ID NO 142
<211> LENGTH: 15
<212> TYPE: DNA
<213> ORGANISM: Artificial sequence
<220> FEATURE:
<223> OTHER INFORMATION: FAM-labeled probe

<400> SEQUENCE: 142
tcgtgcaatg aaagc					15

<210> SEQ ID NO 143
<211> LENGTH: 19
<212> TYPE: DNA
<213> ORGANISM: Artificial sequence
<220> FEATURE:
<223> OTHER INFORMATION: FAM-labeled probe

<400> SEQUENCE: 143
caccaaatga ggtatacac					19

<210> SEQ ID NO 144
<211> LENGTH: 16
<212> TYPE: DNA
<213> ORGANISM: Artificial sequence
<220> FEATURE:
<223> OTHER INFORMATION: FAM-labeled probe

<400> SEQUENCE: 144
tttgcctcgc taaagg					16

<210> SEQ ID NO 145
<211> LENGTH: 14
<212> TYPE: DNA
<213> ORGANISM: Artificial sequence
<220> FEATURE:
<223> OTHER INFORMATION: FAM-labeled probe

<400> SEQUENCE: 145
aggcaccggt ccag					14

<210> SEQ ID NO 146
<211> LENGTH: 17

```
<212> TYPE: DNA
<213> ORGANISM: Artificial sequence
<220> FEATURE:
<223> OTHER INFORMATION: FAM-labeled probe

<400> SEQUENCE: 146
agatctccac gatgatg                                                    17

<210> SEQ ID NO 147
<211> LENGTH: 18
<212> TYPE: DNA
<213> ORGANISM: Artificial sequence
<220> FEATURE:
<223> OTHER INFORMATION: FAM-labeled probe

<400> SEQUENCE: 147
aaagatgatg cttgcttc                                                   18

<210> SEQ ID NO 148
<211> LENGTH: 16
<212> TYPE: DNA
<213> ORGANISM: Artificial sequence
<220> FEATURE:
<223> OTHER INFORMATION: FAM-labeled probe

<400> SEQUENCE: 148
cgctgccagt acctga                                                     16

<210> SEQ ID NO 149
<211> LENGTH: 19
<212> TYPE: DNA
<213> ORGANISM: Artificial sequence
<220> FEATURE:
<223> OTHER INFORMATION: FAM-labeled probe

<400> SEQUENCE: 149
aagaaatgag cggtaatat                                                  19

<210> SEQ ID NO 150
<211> LENGTH: 14
<212> TYPE: DNA
<213> ORGANISM: Artificial sequence
<220> FEATURE:
<223> OTHER INFORMATION: FAM-labeled probe

<400> SEQUENCE: 150
cgccatggct ctaa                                                       14

<210> SEQ ID NO 151
<211> LENGTH: 18
<212> TYPE: DNA
<213> ORGANISM: Artificial sequence
<220> FEATURE:
<223> OTHER INFORMATION: FAM-labeled probe

<400> SEQUENCE: 151
aaagtgtgtc gtcaatta                                                   18

<210> SEQ ID NO 152
<211> LENGTH: 16
<212> TYPE: DNA
<213> ORGANISM: Artificial sequence
<220> FEATURE:
<223> OTHER INFORMATION: FAM-labeled probe

<400> SEQUENCE: 152
```

```
cctggatgac ttgtgt                                                    16

<210> SEQ ID NO 153
<211> LENGTH: 17
<212> TYPE: DNA
<213> ORGANISM: Artificial sequence
<220> FEATURE:
<223> OTHER INFORMATION: FAM-labeled probe

<400> SEQUENCE: 153
aatggctacc gagtcag                                                   17

<210> SEQ ID NO 154
<211> LENGTH: 18
<212> TYPE: DNA
<213> ORGANISM: Artificial sequence
<220> FEATURE:
<223> OTHER INFORMATION: FAM-labeled probe

<400> SEQUENCE: 154
ctgtggttat cgctaaaa                                                  18

<210> SEQ ID NO 155
<211> LENGTH: 19
<212> TYPE: DNA
<213> ORGANISM: Artificial sequence
<220> FEATURE:
<223> OTHER INFORMATION: FAM-labeled probe

<400> SEQUENCE: 155
ctgatgaaag tacttgatc                                                 19

<210> SEQ ID NO 156
<211> LENGTH: 15
<212> TYPE: DNA
<213> ORGANISM: Artificial sequence
<220> FEATURE:
<223> OTHER INFORMATION: FAM-labeled probe

<400> SEQUENCE: 156
ttggagcata cccta                                                     15

<210> SEQ ID NO 157
<211> LENGTH: 29
<212> TYPE: DNA
<213> ORGANISM: Artificial sequence
<220> FEATURE:
<223> OTHER INFORMATION: Taqman forward primer

<400> SEQUENCE: 157
tttgtaacca aactctgacc ttagatgtt                                      29

<210> SEQ ID NO 158
<211> LENGTH: 22
<212> TYPE: DNA
<213> ORGANISM: Artificial sequence
<220> FEATURE:
<223> OTHER INFORMATION: Taqman forward primer

<400> SEQUENCE: 158
gacgaaggtg atgatgcttt gc                                             22

<210> SEQ ID NO 159
<211> LENGTH: 18
<212> TYPE: DNA
<213> ORGANISM: Artificial sequence
```

```
<220> FEATURE:
<223> OTHER INFORMATION: Taqman forward primer

<400> SEQUENCE: 159
cggaaggtcg cgatcctc                                                 18

<210> SEQ ID NO 160
<211> LENGTH: 25
<212> TYPE: DNA
<213> ORGANISM: Artificial sequence
<220> FEATURE:
<223> OTHER INFORMATION: Taqman forward primer

<400> SEQUENCE: 160
ggacgatgcg atcaagacta caaat                                         25

<210> SEQ ID NO 161
<211> LENGTH: 24
<212> TYPE: DNA
<213> ORGANISM: Artificial sequence
<220> FEATURE:
<223> OTHER INFORMATION: Taqman forward primer

<400> SEQUENCE: 161
gtcctctagc tcttttcggt gtag                                          24

<210> SEQ ID NO 162
<211> LENGTH: 25
<212> TYPE: DNA
<213> ORGANISM: Artificial sequence
<220> FEATURE:
<223> OTHER INFORMATION: Taqman forward primer

<400> SEQUENCE: 162
gaatcccatg atgtcaaatc cgttt                                         25

<210> SEQ ID NO 163
<211> LENGTH: 24
<212> TYPE: DNA
<213> ORGANISM: Artificial sequence
<220> FEATURE:
<223> OTHER INFORMATION: Taqman forward primer

<400> SEQUENCE: 163
tgtgcaattt gtatccctgg cata                                          24

<210> SEQ ID NO 164
<211> LENGTH: 25
<212> TYPE: DNA
<213> ORGANISM: Artificial sequence
<220> FEATURE:
<223> OTHER INFORMATION: Taqman forward primer

<400> SEQUENCE: 164 cttttcctc aagctggttg tcaat                                          25

<210> SEQ ID NO 165
<211> LENGTH: 25
<212> TYPE: DNA
<213> ORGANISM: Artificial sequence
<220> FEATURE:
<223> OTHER INFORMATION: Taqman forward primer

<400> SEQUENCE: 165
tccatttctt cagccctact ttgtc                                         25
```

<210> SEQ ID NO 166
<211> LENGTH: 17
<212> TYPE: DNA
<213> ORGANISM: Artificial sequence
<220> FEATURE:
<223> OTHER INFORMATION: Taqman forward primer

<400> SEQUENCE: 166
gagcctgcgg catcatg                                                   17

<210> SEQ ID NO 167
<211> LENGTH: 26
<212> TYPE: DNA
<213> ORGANISM: Artificial sequence
<220> FEATURE:
<223> OTHER INFORMATION: Taqman forward primer

<400> SEQUENCE: 167
agaaatgtct gaattcagag ctctgg                                         26

<210> SEQ ID NO 168
<211> LENGTH: 36
<212> TYPE: DNA
<213> ORGANISM: Artificial sequence
<220> FEATURE:
<223> OTHER INFORMATION: Taqman forward primer

<400> SEQUENCE: 168
attgatgtat gttgtatgta aacaataaca gtaagt                              36

<210> SEQ ID NO 169
<211> LENGTH: 24
<212> TYPE: DNA
<213> ORGANISM: Artificial sequence
<220> FEATURE:
<223> OTHER INFORMATION: Taqman forward primer

<400> SEQUENCE: 169
acatttccac acgttgcatt ttgt                                           24

<210> SEQ ID NO 170
<211> LENGTH: 23
<212> TYPE: DNA
<213> ORGANISM: Artificial sequence
<220> FEATURE:
<223> OTHER INFORMATION: Taqman forward primer

<400> SEQUENCE: 170
gaacagatgg gatgatgcag aga                                            23

<210> SEQ ID NO 171
<211> LENGTH: 20
<212> TYPE: DNA
<213> ORGANISM: Artificial sequence
<220> FEATURE:
<223> OTHER INFORMATION: Taqman forward primer

<400> SEQUENCE: 171
gggtcgctgg caattttgaa                                                20

<210> SEQ ID NO 172
<211> LENGTH: 20
<212> TYPE: DNA
<213> ORGANISM: Artificial sequence
<220> FEATURE:
<223> OTHER INFORMATION: Taqman forward primer

<400> SEQUENCE: 172
ctgcatcatc accccctctt                                           20

<210> SEQ ID NO 173
<211> LENGTH: 22
<212> TYPE: DNA
<213> ORGANISM: Artificial sequence
<220> FEATURE:
<223> OTHER INFORMATION: Taqman forward primer

<400> SEQUENCE: 173
cttatgacca ggcagctttt gc                                        22

<210> SEQ ID NO 174
<211> LENGTH: 25
<212> TYPE: DNA
<213> ORGANISM: Artificial sequence
<220> FEATURE:
<223> OTHER INFORMATION: Taqman forward primer

<400> SEQUENCE: 174
cccctacctc ttatcagaac atcga                                     25

<210> SEQ ID NO 175
<211> LENGTH: 27
<212> TYPE: DNA
<213> ORGANISM: Artificial sequence
<220> FEATURE:
<223> OTHER INFORMATION: Taqman forward primer

<400> SEQUENCE: 175
tcacagacat tagtatgaaa gcaagca                                   27

<210> SEQ ID NO 176
<211> LENGTH: 23
<212> TYPE: DNA
<213> ORGANISM: Artificial sequence
<220> FEATURE:
<223> OTHER INFORMATION: Taqman forward primer

<400> SEQUENCE: 176 cccctttcaag agcaagattc tca                                      23

<210> SEQ ID NO 177
<211> LENGTH: 30
<212> TYPE: DNA
<213> ORGANISM: Artificial sequence
<220> FEATURE:
<223> OTHER INFORMATION: Taqman forward primer

<400> SEQUENCE: 177
gaggattcat tcattcatgt taaagtgcat                                30

<210> SEQ ID NO 178
<211> LENGTH: 28
<212> TYPE: DNA
<213> ORGANISM: Artificial sequence
<220> FEATURE:
<223> OTHER INFORMATION: Taqman forward primer

<400> SEQUENCE: 178 catgccccctt atcttgctat ttatctca                                 28

<210> SEQ ID NO 179

```
<211> LENGTH: 31
<212> TYPE: DNA
<213> ORGANISM: Artificial sequence
<220> FEATURE:
<223> OTHER INFORMATION: Taqman forward primer

<400> SEQUENCE: 179
gatattcttc tctgtaaata gcctcgagat t                              31

<210> SEQ ID NO 180
<211> LENGTH: 25
<212> TYPE: DNA
<213> ORGANISM: Artificial sequence
<220> FEATURE:
<223> OTHER INFORMATION: Taqman forward primer

<400> SEQUENCE: 180
ctgcaggaag caatagaaaa agcaa                                     25

<210> SEQ ID NO 181
<211> LENGTH: 25
<212> TYPE: DNA
<213> ORGANISM: Artificial sequence
<220> FEATURE:
<223> OTHER INFORMATION: Taqman forward primer

<400> SEQUENCE: 181
gcttcattgt cttgctggtt ttcaa                                     25

<210> SEQ ID NO 182
<211> LENGTH: 24
<212> TYPE: DNA
<213> ORGANISM: Artificial sequence
<220> FEATURE:
<223> OTHER INFORMATION: Taqman forward primer

<400> SEQUENCE: 182
gcagagtaat cggcatgtct tctt                                      24

<210> SEQ ID NO 183
<211> LENGTH: 33
<212> TYPE: DNA
<213> ORGANISM: Artificial sequence
<220> FEATURE:
<223> OTHER INFORMATION: Taqman forward primer

<400> SEQUENCE: 183
cccatttgtt tctaactaaa tctcaaagga aaa                            33

<210> SEQ ID NO 184
<211> LENGTH: 25
<212> TYPE: DNA
<213> ORGANISM: Artificial sequence
<220> FEATURE:
<223> OTHER INFORMATION: Taqman forward primer

<400> SEQUENCE: 184
cgatgcattt gagattgttg tggaa                                     25

<210> SEQ ID NO 185
<211> LENGTH: 35
<212> TYPE: DNA
<213> ORGANISM: Artificial sequence
<220> FEATURE:
<223> OTHER INFORMATION: Taqman forward primer

<400> SEQUENCE: 185
```

-continued taaaaagaat actattatcc ttaaatcaac aatct                           35

<210> SEQ ID NO 186
<211> LENGTH: 17
<212> TYPE: DNA
<213> ORGANISM: Artificial sequence
<220> FEATURE:
<223> OTHER INFORMATION: Taqman forward primer

<400> SEQUENCE: 186
cgctggagct cctggtg                                              17

<210> SEQ ID NO 187
<211> LENGTH: 24
<212> TYPE: DNA
<213> ORGANISM: Artificial sequence
<220> FEATURE:
<223> OTHER INFORMATION: Taqman forward primer

<400> SEQUENCE: 187
attgccgtga agaaagtact ggaa                                      24

<210> SEQ ID NO 188
<211> LENGTH: 23
<212> TYPE: DNA
<213> ORGANISM: Artificial sequence
<220> FEATURE:
<223> OTHER INFORMATION: Taqman forward primer

<400> SEQUENCE: 188
agccacaaca atagaccaaa atg                                       23

<210> SEQ ID NO 189
<211> LENGTH: 25
<212> TYPE: DNA
<213> ORGANISM: Artificial sequence
<220> FEATURE:
<223> OTHER INFORMATION: Taqman forward primer

<400> SEQUENCE: 189
ggagtagaaa caagtgaagc tgcta                                     25

<210> SEQ ID NO 190
<211> LENGTH: 25
<212> TYPE: DNA
<213> ORGANISM: Artificial sequence
<220> FEATURE:
<223> OTHER INFORMATION: Taqman forward primer

<400> SEQUENCE: 190
aggaagttga aaaggccatt aacga                                     25

<210> SEQ ID NO 191
<211> LENGTH: 23
<212> TYPE: DNA
<213> ORGANISM: Artificial sequence
<220> FEATURE:
<223> OTHER INFORMATION: Taqman forward primer

<400> SEQUENCE: 191
cgagtgctcc ctcatgtatt tgg                                       23

<210> SEQ ID NO 192
<211> LENGTH: 25
<212> TYPE: DNA

<213> ORGANISM: Artificial sequence
<220> FEATURE:
<223> OTHER INFORMATION: Taqman forward primer

<400> SEQUENCE: 192
ccttgagtac ctaggtgact atcgt                                25

<210> SEQ ID NO 193
<211> LENGTH: 25
<212> TYPE: DNA
<213> ORGANISM: Artificial sequence
<220> FEATURE:
<223> OTHER INFORMATION: Taqman forward primer

<400> SEQUENCE: 193
aagagtaaga ggttaaacgg gttgc                                25

<210> SEQ ID NO 194
<211> LENGTH: 25
<212> TYPE: DNA
<213> ORGANISM: Artificial sequence
<220> FEATURE:
<223> OTHER INFORMATION: Taqman forward primer

<400> SEQUENCE: 194
gcttatgatg ctgcttttgc cttag                                25

<210> SEQ ID NO 195
<211> LENGTH: 25
<212> TYPE: DNA
<213> ORGANISM: Artificial sequence
<220> FEATURE:
<223> OTHER INFORMATION: Taqman forward primer

<400> SEQUENCE: 195
cgatgaaggc aatcttacac tagca                                25

<210> SEQ ID NO 196
<211> LENGTH: 25
<212> TYPE: DNA
<213> ORGANISM: Artificial sequence
<220> FEATURE:
<223> OTHER INFORMATION: Taqman forward primer

<400> SEQUENCE: 196
actccactgg catgcaatat gttat                                25

<210> SEQ ID NO 197
<211> LENGTH: 29
<212> TYPE: DNA
<213> ORGANISM: Artificial sequence
<220> FEATURE:
<223> OTHER INFORMATION: Taqman forward primer

<400> SEQUENCE: 197
agtagaaata agtgaagaat attgatgtg                            29

<210> SEQ ID NO 198
<211> LENGTH: 23
<212> TYPE: DNA
<213> ORGANISM: Artificial sequence
<220> FEATURE:
<223> OTHER INFORMATION: Taqman reverse primer

<400> SEQUENCE: 198
ggttggagat ccaaattgct atc                                  23

<210> SEQ ID NO 199
<211> LENGTH: 24
<212> TYPE: DNA
<213> ORGANISM: Artificial sequence
<220> FEATURE:
<223> OTHER INFORMATION: Taqman reverse primer

<400> SEQUENCE: 199
gctaggctgg taggttcttt tagt                                    24

<210> SEQ ID NO 200
<211> LENGTH: 25
<212> TYPE: DNA
<213> ORGANISM: Artificial sequence
<220> FEATURE:
<223> OTHER INFORMATION: Taqman reverse primer

<400> SEQUENCE: 200
gagctagctt ggtaacaaga ggatt                                   25

<210> SEQ ID NO 201
<211> LENGTH: 25
<212> TYPE: DNA
<213> ORGANISM: Artificial sequence
<220> FEATURE:
<223> OTHER INFORMATION: Taqman reverse primer

<400> SEQUENCE: 201
ggtaatggta ttctccaacc ttggt                                   25

<210> SEQ ID NO 202
<211> LENGTH: 26
<212> TYPE: DNA
<213> ORGANISM: Artificial sequence
<220> FEATURE:
<223> OTHER INFORMATION: Taqman reverse primer

<400> SEQUENCE: 202
cactatagtg cagtcaaagt ctgagt                                  26

<210> SEQ ID NO 203
<211> LENGTH: 23
<212> TYPE: DNA
<213> ORGANISM: Artificial sequence
<220> FEATURE:
<223> OTHER INFORMATION: Taqman reverse primer

<400> SEQUENCE: 203
gcacttggac agcaacattt tga                                     23

<210> SEQ ID NO 204
<211> LENGTH: 30
<212> TYPE: DNA
<213> ORGANISM: Artificial sequence
<220> FEATURE:
<223> OTHER INFORMATION: Taqman reverse primer

<400> SEQUENCE: 204
ttagattttc tacctatgtc ctaccaggtt                              30

<210> SEQ ID NO 205
<211> LENGTH: 19
<212> TYPE: DNA
<213> ORGANISM: Artificial sequence
<220> FEATURE:

<223> OTHER INFORMATION: Taqman reverse primer

<400> SEQUENCE: 205
accttctctc aattgtgca                                                19

<210> SEQ ID NO 206
<211> LENGTH: 39
<212> TYPE: DNA
<213> ORGANISM: Artificial sequence
<220> FEATURE:
<223> OTHER INFORMATION: Taqman reverse primer

<400> SEQUENCE: 206
aaatcataag aattaagaat tcaaaatcga attcaaaag                          39

<210> SEQ ID NO 207
<211> LENGTH: 31
<212> TYPE: DNA
<213> ORGANISM: Artificial sequence
<220> FEATURE:
<223> OTHER INFORMATION: Taqman reverse primer

<400> SEQUENCE: 207
tttaccaaag taattctaaa taaggattgt t                                  31

<210> SEQ ID NO 208
<211> LENGTH: 21
<212> TYPE: DNA
<213> ORGANISM: Artificial sequence
<220> FEATURE:
<223> OTHER INFORMATION: Taqman reverse primer

<400> SEQUENCE: 208
gagtcccgat tgttggcaaa c                                             21

<210> SEQ ID NO 209
<211> LENGTH: 24
<212> TYPE: DNA
<213> ORGANISM: Artificial sequence
<220> FEATURE:
<223> OTHER INFORMATION: Taqman reverse primer

<400> SEQUENCE: 209
caaagcaact cccagttctt caac                                          24

<210> SEQ ID NO 210
<211> LENGTH: 30
<212> TYPE: DNA
<213> ORGANISM: Artificial sequence
<220> FEATURE:
<223> OTHER INFORMATION: Taqman reverse primer

<400> SEQUENCE: 210
ttttaccaaa agcactttta tattattgtt                                    30

<210> SEQ ID NO 211
<211> LENGTH: 25
<212> TYPE: DNA
<213> ORGANISM: Artificial sequence
<220> FEATURE:
<223> OTHER INFORMATION: Taqman reverse primer

<400> SEQUENCE: 211
ctctatacaa ctccatccag gcaat                                         25

```
<210> SEQ ID NO 212
<211> LENGTH: 25
<212> TYPE: DNA
<213> ORGANISM: Artificial sequence
<220> FEATURE:
<223> OTHER INFORMATION: Taqman reverse primer

<400> SEQUENCE: 212
gcttttaggc acttgacttc tctca                                             25

<210> SEQ ID NO 213
<211> LENGTH: 23
<212> TYPE: DNA
<213> ORGANISM: Artificial sequence
<220> FEATURE:
<223> OTHER INFORMATION: Taqman reverse primer

<400> SEQUENCE: 213
cggaaattgt acggcgggaa tat                                               23

<210> SEQ ID NO 214
<211> LENGTH: 25
<212> TYPE: DNA
<213> ORGANISM: Artificial sequence
<220> FEATURE:
<223> OTHER INFORMATION: Taqman reverse primer

<400> SEQUENCE: 214
gcttttaggc acttgacttc tctca                                             25

<210> SEQ ID NO 215
<211> LENGTH: 25
<212> TYPE: DNA
<213> ORGANISM: Artificial sequence
<220> FEATURE:
<223> OTHER INFORMATION: Taqman reverse primer

<400> SEQUENCE: 215
ggcaattttt gatgaggcaa tggaa                                             25

<210> SEQ ID NO 216
<211> LENGTH: 28
<212> TYPE: DNA
<213> ORGANISM: Artificial sequence
<220> FEATURE:
<223> OTHER INFORMATION: Taqman reverse primer

<400> SEQUENCE: 216
gcaagatgca aaactcaaat ttctagca                                          28

<210> SEQ ID NO 217
<211> LENGTH: 24
<212> TYPE: DNA
<213> ORGANISM: Artificial sequence
<220> FEATURE:
<223> OTHER INFORMATION: Taqman reverse primer

<400> SEQUENCE: 217
gccctgatct tgagtgtagt ttgg                                              24

<210> SEQ ID NO 218
<211> LENGTH: 25
<212> TYPE: DNA
<213> ORGANISM: Artificial sequence
<220> FEATURE:
<223> OTHER INFORMATION: Taqman reverse primer
```

<400> SEQUENCE: 218
gcaagggtaa gaaaatcgaa aacca                                          25

<210> SEQ ID NO 219
<211> LENGTH: 25
<212> TYPE: DNA
<213> ORGANISM: Artificial sequence
<220> FEATURE:
<223> OTHER INFORMATION: Taqman reverse primer

<400> SEQUENCE: 219
cagttaagaa gggattcctc tgcat                                          25

<210> SEQ ID NO 220
<211> LENGTH: 24
<212> TYPE: DNA
<213> ORGANISM: Artificial sequence
<220> FEATURE:
<223> OTHER INFORMATION: Taqman reverse primer

<400> SEQUENCE: 220
tgggtcctac tttgtttgtt ggat                                           24

<210> SEQ ID NO 221
<211> LENGTH: 35
<212> TYPE: DNA
<213> ORGANISM: Artificial sequence
<220> FEATURE:
<223> OTHER INFORMATION: Taqman reverse primer

<400> SEQUENCE: 221
aacataatta ataaataagt gtaactttgc atgaa                               35

<210> SEQ ID NO 222
<211> LENGTH: 25
<212> TYPE: DNA
<213> ORGANISM: Artificial sequence
<220> FEATURE:
<223> OTHER INFORMATION: Taqman reverse primer

<400> SEQUENCE: 222
cctgcctttt cacatttttc ccatt                                          25

<210> SEQ ID NO 223
<211> LENGTH: 20
<212> TYPE: DNA
<213> ORGANISM: Artificial sequence
<220> FEATURE:
<223> OTHER INFORMATION: Taqman reverse primer

<400> SEQUENCE: 223
gtcgtactct cctgcaccaa                                                20

<210> SEQ ID NO 224
<211> LENGTH: 27
<212> TYPE: DNA
<213> ORGANISM: Artificial sequence
<220> FEATURE:
<223> OTHER INFORMATION: Taqman reverse primer

<400> SEQUENCE: 224
tgattgactg attgtgtagc ttgaaga                                        27

<210> SEQ ID NO 225
<211> LENGTH: 30

```
<212> TYPE: DNA
<213> ORGANISM: Artificial sequence
<220> FEATURE:
<223> OTHER INFORMATION: Taqman reverse primer

<400> SEQUENCE: 225
gtcatccaaa catttatcgt tacaaaggaa                                    30

<210> SEQ ID NO 226
<211> LENGTH: 26
<212> TYPE: DNA
<213> ORGANISM: Artificial sequence
<220> FEATURE:
<223> OTHER INFORMATION: Taqman reverse primer

<400> SEQUENCE: 226
agttcaagag aaacgaaact cggtaa                                        26

<210> SEQ ID NO 227
<211> LENGTH: 21
<212> TYPE: DNA
<213> ORGANISM: Artificial sequence
<220> FEATURE:
<223> OTHER INFORMATION: Taqman reverse primer

<400> SEQUENCE: 227
cacccgaagt tccagaaggt t                                             21

<210> SEQ ID NO 228
<211> LENGTH: 27
<212> TYPE: DNA
<213> ORGANISM: Artificial sequence
<220> FEATURE:
<223> OTHER INFORMATION: Taqman reverse primer

<400> SEQUENCE: 228
gccttaactt gctgattatc tcaacct                                       27

<210> SEQ ID NO 229
<211> LENGTH: 19
<212> TYPE: DNA
<213> ORGANISM: Artificial sequence
<220> FEATURE:
<223> OTHER INFORMATION: Taqman reverse primer

<400> SEQUENCE: 229
ccttgtgctg cctggttga                                                19

<210> SEQ ID NO 230
<211> LENGTH: 26
<212> TYPE: DNA
<213> ORGANISM: Artificial sequence
<220> FEATURE:
<223> OTHER INFORMATION: Taqman reverse primer

<400> SEQUENCE: 230
tccgaaggta atagttctga cgaaga                                        26

<210> SEQ ID NO 231
<211> LENGTH: 29
<212> TYPE: DNA
<213> ORGANISM: Artificial sequence
<220> FEATURE:
<223> OTHER INFORMATION: Taqman reverse primer

<400> SEQUENCE: 231
```

```
cttttttgaac catttctttt ctcctgtct                                      29
```

<210> SEQ ID NO 232
<211> LENGTH: 25
<212> TYPE: DNA
<213> ORGANISM: Artificial sequence
<220> FEATURE:
<223> OTHER INFORMATION: Taqman reverse primer

<400> SEQUENCE: 232

```
cctaccaaaa cgccaaagaa ttaca                                           25
```

<210> SEQ ID NO 233
<211> LENGTH: 33
<212> TYPE: DNA
<213> ORGANISM: Artificial sequence
<220> FEATURE:
<223> OTHER INFORMATION: Taqman reverse primer

<400> SEQUENCE: 233

```
tcttgaatct ctctgttaat agttcaaatc gtg                                  33
```

<210> SEQ ID NO 234
<211> LENGTH: 30
<212> TYPE: DNA
<213> ORGANISM: Artificial sequence
<220> FEATURE:
<223> OTHER INFORMATION: Taqman reverse primer

<400> SEQUENCE: 234

```
aattatacat gatttcagga aatgaagcac                                      30
```

<210> SEQ ID NO 235
<211> LENGTH: 28
<212> TYPE: DNA
<213> ORGANISM: Artificial sequence
<220> FEATURE:
<223> OTHER INFORMATION: Taqman reverse primer

<400> SEQUENCE: 235

```
tcattactat agttataagc tggctgag                                        28
```

<210> SEQ ID NO 236
<211> LENGTH: 23
<212> TYPE: DNA
<213> ORGANISM: Artificial sequence
<220> FEATURE:
<223> OTHER INFORMATION: Taqman reverse primer

<400> SEQUENCE: 236

```
gctcattgtt aagtgagcca gtg                                             23
```

<210> SEQ ID NO 237
<211> LENGTH: 24
<212> TYPE: DNA
<213> ORGANISM: Artificial sequence
<220> FEATURE:
<223> OTHER INFORMATION: Taqman reverse primer

<400> SEQUENCE: 237

```
agcgaacagt cacaacttgt aaca                                            24
```

<210> SEQ ID NO 238
<211> LENGTH: 24
<212> TYPE: DNA
<213> ORGANISM: Artificial sequence

```
<220> FEATURE:
<223> OTHER INFORMATION: Taqman reverse primer

<400> SEQUENCE: 238
tggtttgagc ttgttggttt ggag                                              24

<210> SEQ ID NO 239
<211> LENGTH: 28
<212> TYPE: DNA
<213> ORGANISM: Artificial sequence
<220> FEATURE:
<223> OTHER INFORMATION: Taqman forward primer

<400> SEQUENCE: 239
atcattttag ccatatcgta aattgtca                                          28

<210> SEQ ID NO 240
<211> LENGTH: 25
<212> TYPE: DNA
<213> ORGANISM: Artificial sequence
<220> FEATURE:
<223> OTHER INFORMATION: Taqman forward primer

<400> SEQUENCE: 240
tacaatatga tacagaaaat cagag                                             25
```